(12) United States Patent
Glusker et al.

(10) Patent No.: US 10,245,394 B2
(45) Date of Patent: Apr. 2, 2019

(54) POWDER DISPERSION APPARATUS, METHOD OF MAKING AND USING THE APPARATUS, AND COMPONENTS THAT CAN BE USED ON THE APPARATUS AND OTHER DEVICES

(71) Applicants: Mark Glusker, San Mateo, CA (US); George S Axford, Pacifica, CA (US); William W Alston, San Jose, CA (US); John Palmer-Felgate, Horsham (GB); Jonathan Wilkins, Cambridge (GB); Willard R Foss, Thousand Oaks, CA (US); Nagaraja Rao, San Leandro, CA (US); Mark Postich, Menlo, CA (US); Neeraj Pakala, Cupertino, CA (US); David S Maltz, San Francisco, CA (US); Keith Ung, Belmont, CA (US)

(72) Inventors: Mark Glusker, San Mateo, CA (US); George S Axford, Pacifica, CA (US); William W Alston, San Jose, CA (US); John Palmer-Felgate, Horsham (GB); Jonathan Wilkins, Cambridge (GB); Willard R Foss, Thousand Oaks, CA (US); Nagaraja Rao, San Leandro, CA (US); Mark Postich, Menlo, CA (US); Neeraj Pakala, Cupertino, CA (US); David S Maltz, San Francisco, CA (US); Keith Ung, Belmont, CA (US)

( * ) Notice: Subject to any disclaimer, the term of this patent is extended or adjusted under 35 U.S.C. 154(b) by 913 days.

(21) Appl. No.: 14/053,946

(22) Filed: Oct. 15, 2013

(65) Prior Publication Data

US 2014/0034052 A1     Feb. 6, 2014

Related U.S. Application Data

(62) Division of application No. 12/447,045, filed as application No. PCT/US2007/022830 on Oct. 25, 2007, now Pat. No. 8,573,197.

(Continued)

(51) Int. Cl.
| | | |
|---|---|---|
| A61M 15/00 | (2006.01) | |
| A61M 16/00 | (2006.01) | |
| A61M 11/00 | (2006.01) | |

(52) U.S. Cl.
CPC .... *A61M 15/0028* (2013.01); *A61M 15/0005* (2014.02); *A61M 15/0036* (2014.02);
(Continued)

(58) Field of Classification Search
CPC ............ A61M 15/0028; A61M 11/001; A61M 15/0016; A61M 15/0036; A61M 15/0041;
(Continued)

(56) References Cited

U.S. PATENT DOCUMENTS

| | | |
|---|---|---|
| 3,425,600 A | 2/1969 | Abplanalp |
| 3,888,253 A | 6/1975 | Watt et al. |

(Continued)

FOREIGN PATENT DOCUMENTS

| | | |
|---|---|---|
| CA | 2064860 C | 3/2002 |
| CN | 1411383 A | 4/2003 |

(Continued)

OTHER PUBLICATIONS

International Search Report, PCT/US2007/022830 (Sep. 30, 2008).
(Continued)

*Primary Examiner* — Theodore Stigell

(57) ABSTRACT

Methods and apparatuses for the pulmonary delivery of a composition, such as methods and apparatuses for dispersing dry powder medicaments for inhalation by a patient. Elements or aspects of the apparatuses, including receptacle puncturing, mechanisms, deoccluding devices, receptacle impacting devices, and receptacle lock devices or systems.

2 Claims, 65 Drawing Sheets

Related U.S. Application Data

(60) Provisional application No. 60/906,977, filed on Mar. 13, 2007, provisional application No. 60/854,601, filed on Oct. 25, 2006.

(52) U.S. Cl.
CPC .... *A61M 15/0041* (2014.02); *A61M 15/0048* (2014.02); *A61M 11/001* (2014.02); *A61M 15/0016* (2014.02); *A61M 15/0051* (2014.02); *A61M 15/0081* (2014.02); *A61M 15/0093* (2014.02); *A61M 15/0096* (2014.02); *A61M 2016/0015* (2013.01); *A61M 2202/064* (2013.01); *A61M 2205/43* (2013.01); *A61M 2205/581* (2013.01); *A61M 2205/582* (2013.01)

(58) Field of Classification Search
CPC .......... A61M 15/0048; A61M 15/0093; A61M 15/0005; A61M 2016/0015; A61M 2202/064; A61M 2205/43; A61M 2205/581; A61M 2205/582; A61M 15/0051
See application file for complete search history.

(56) References Cited

U.S. PATENT DOCUMENTS

| | | |
|---|---|---|
| 3,921,637 A | 11/1975 | Bennie et al. |
| 3,991,761 A | 11/1976 | Cocozza |
| 4,069,819 A | 1/1978 | Valentini et al. |
| 4,249,526 A | 2/1981 | Dean et al. |
| 4,338,931 A | 7/1982 | Cavazza |
| 4,446,862 A | 5/1984 | Baum et al. |
| 4,627,432 A | 12/1986 | Newell et al. |
| 4,668,862 A | 5/1987 | Waibel |
| 4,811,731 A | 3/1989 | Newell et al. |
| 4,825,913 A | 5/1989 | Stott |
| 4,884,565 A | 12/1989 | Cocozza |
| 4,889,114 A | 12/1989 | Kladders |
| 4,995,385 A | 2/1991 | Valentini et al. |
| 5,035,237 A | 7/1991 | Newell et al. |
| 5,048,514 A | 9/1991 | Ramella |
| 5,213,236 A | 5/1993 | Brown et al. |
| 5,377,877 A | 1/1995 | Brown et al. |
| 5,409,144 A | 4/1995 | Brown |
| 5,531,363 A | 7/1996 | Gross et al. |
| 5,589,275 A | 12/1996 | Breitler et al. |
| 5,590,645 A | 1/1997 | Davies et al. |
| 5,740,794 A * | 4/1998 | Smith ............... A61M 15/0045 128/203.15 |
| 5,833,071 A | 11/1998 | Ray |
| 5,839,614 A | 11/1998 | Brown |
| 5,922,675 A | 7/1999 | Baker et al. |
| 6,065,642 A | 5/2000 | Brown |
| 6,079,594 A | 6/2000 | Brown et al. |
| 6,109,261 A | 8/2000 | Clarke et al. |
| 6,257,233 B1 | 7/2001 | Burr et al. |
| 6,270,869 B1 | 8/2001 | Zeiter et al. |
| 6,273,296 B1 | 8/2001 | Brown |
| 6,360,744 B1 | 3/2002 | Myrman et al. |
| 6,405,901 B1 | 6/2002 | Schantz et al. |
| 6,422,236 B1 | 7/2002 | Nilsson et al. |
| 6,436,227 B1 | 8/2002 | Adler |
| 6,526,969 B2 | 3/2003 | Nilsson et al. |
| 6,606,992 B1 | 8/2003 | Schuler et al. |
| 6,622,723 B1 | 9/2003 | Nilsson et al. |
| 6,651,341 B1 | 11/2003 | Myrman et al. |
| 6,668,823 B1 | 12/2003 | Liu |
| 6,668,827 B2 | 12/2003 | Schuler et al. |
| 6,840,239 B2 | 1/2005 | Myrman |
| 6,868,853 B1 | 3/2005 | Nilsson et al. |
| 6,881,398 B2 | 4/2005 | Myrman et al. |
| 6,951,295 B1 | 10/2005 | Gaus et al. |
| 7,086,572 B2 | 8/2006 | Socier et al. |
| 7,185,651 B2 | 3/2007 | Alston et al. |
| 2001/0020472 A1 | 9/2001 | Horlin |
| 2005/0279356 A1 | 12/2005 | Friberg et al. |
| 2007/0068524 A1 | 3/2007 | Nilsson et al. |
| 2007/0295333 A1 | 12/2007 | Fourment et al. |

FOREIGN PATENT DOCUMENTS

| | | |
|---|---|---|
| EP | 0424790 A2 | 5/1991 |
| EP | 0467172 A1 | 1/1992 |
| EP | 0469814 A1 | 2/1992 |
| EP | 0634184 A1 | 1/1995 |
| EP | 1685866 A2 | 8/2006 |
| FR | 2516387 A1 | 5/1983 |
| JP | H03184563 | 8/1991 |
| JP | 2001517984 A | 10/2001 |
| WO | 9007351 A1 | 7/1990 |
| WO | 9102558 A1 | 3/1991 |
| WO | 9309832 A1 | 5/1993 |
| WO | 9408522 A1 | 4/1994 |
| WO | 9531479 A1 | 11/1995 |
| WO | 9609085 A1 | 3/1996 |
| WO | 9632096 A1 | 10/1996 |
| WO | 9632149 A1 | 10/1996 |
| WO | 9841264 A1 | 9/1998 |
| WO | 9939760 A1 | 8/1999 |
| WO | 0143802 A1 | 6/2001 |
| WO | 01/87393 A2 | 11/2001 |
| WO | 0185136 A2 | 11/2001 |
| WO | 0185137 A2 | 11/2001 |
| WO | 03086515 A1 | 10/2003 |
| WO | 03086516 A1 | 10/2003 |
| WO | 03086517 A1 | 10/2003 |
| WO | 2004082750 A1 | 9/2004 |
| WO | 2004110539 A1 | 12/2004 |
| WO | 2005025656 A1 | 3/2005 |
| WO | 2006054021 A2 | 5/2006 |

OTHER PUBLICATIONS

Written Opinion, PCT/US2007/022830 (Apr. 28, 2009).
International Search Report, PCT/US2009/001716 (Mar. 5, 2010).
Written Opinion, PCT/US2009/001716 (Sep. 21, 2010).

* cited by examiner

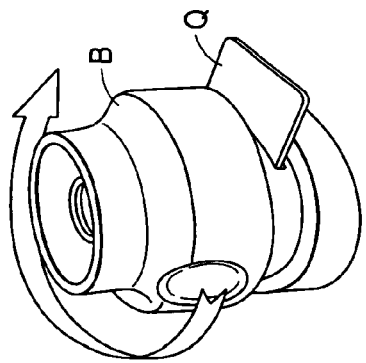
FIG. 3
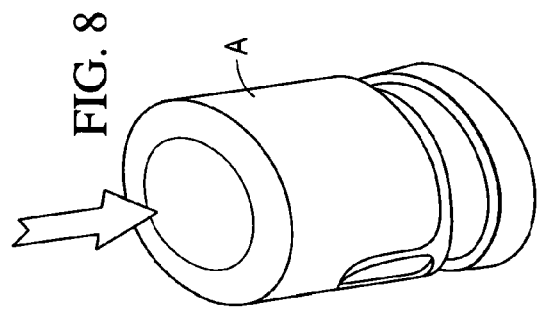
FIG. 4
FIG. 5
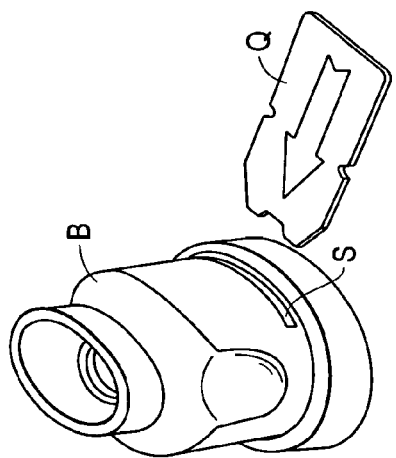
FIG. 6
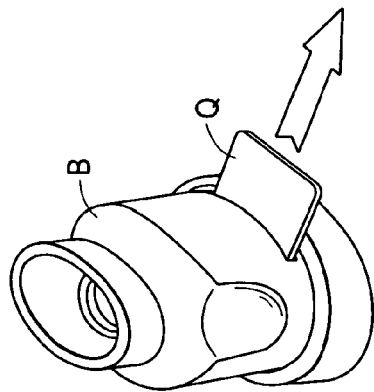
FIG. 7
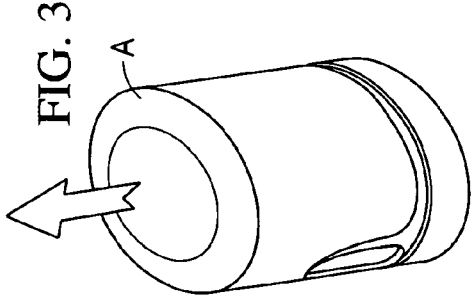
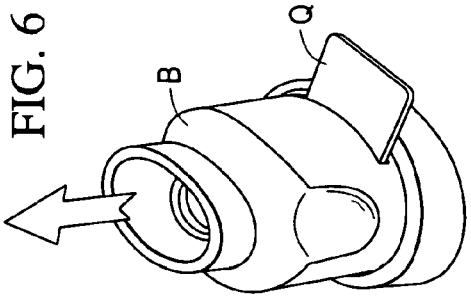
FIG. 8

FIG. 44
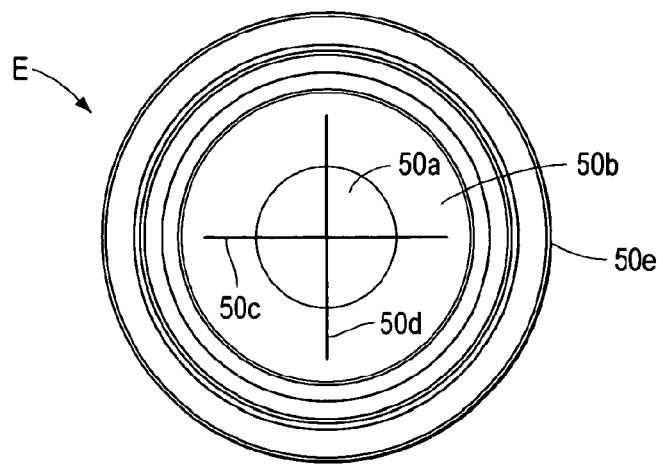
FIG. 45
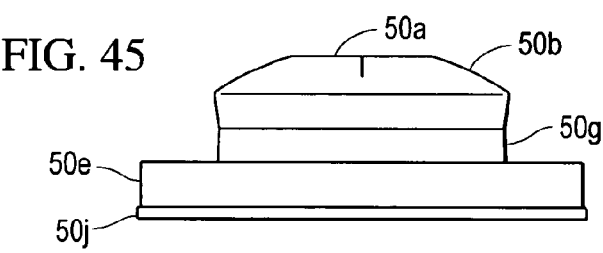
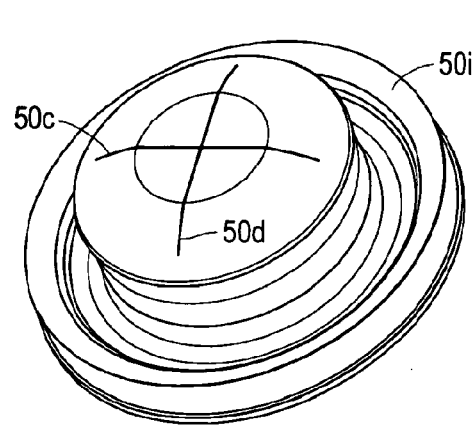
FIG. 46
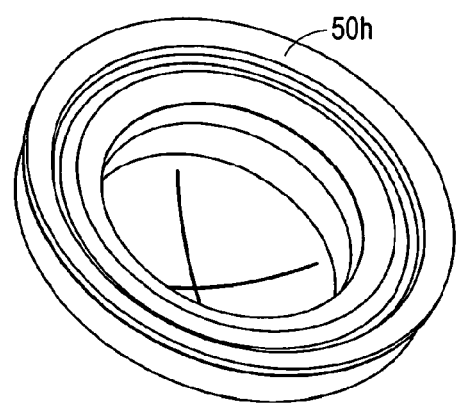
FIG. 47

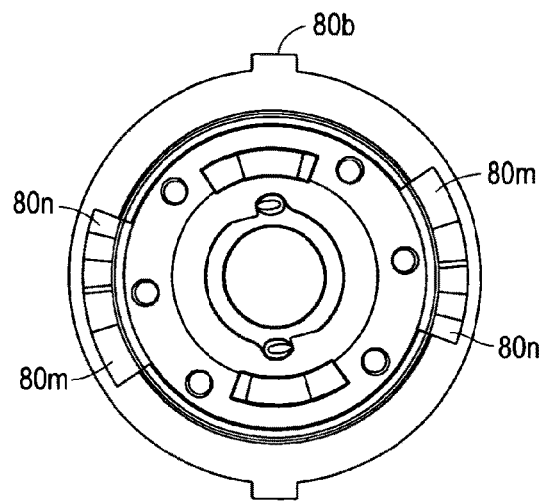
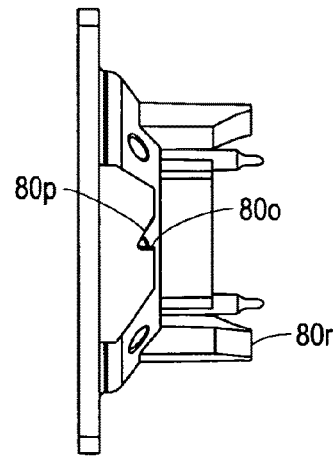
FIG. 56  FIG. 57
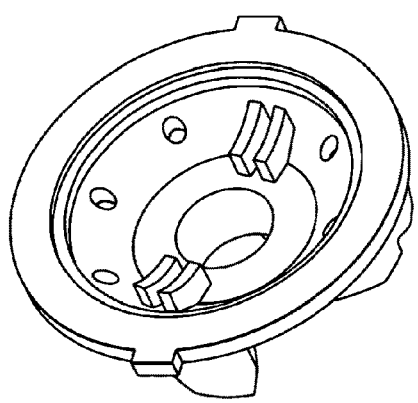
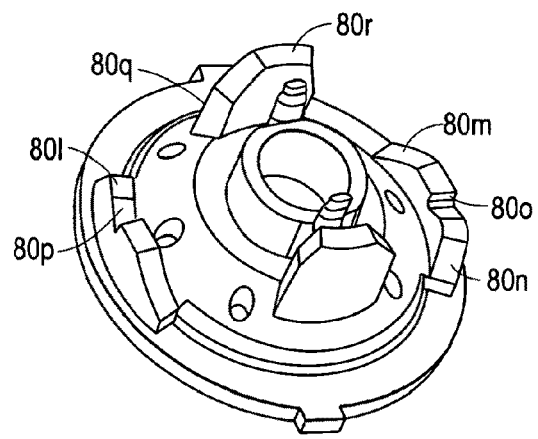
FIG. 58  FIG. 59

FIG. 69
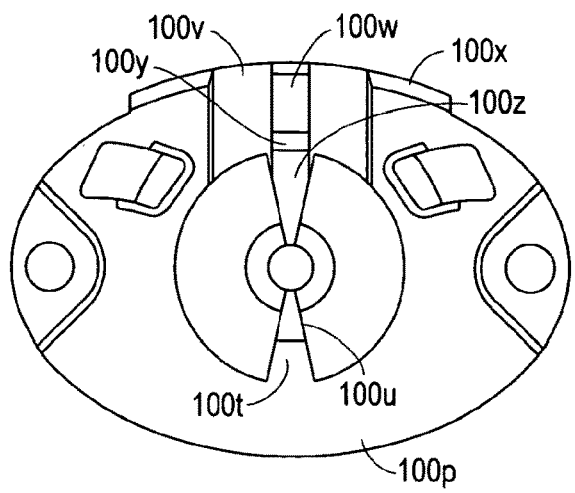
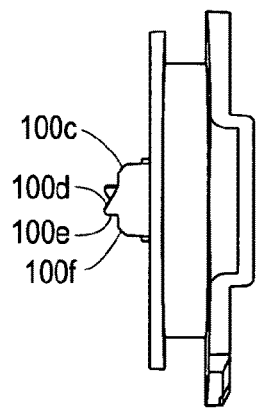
FIG. 70
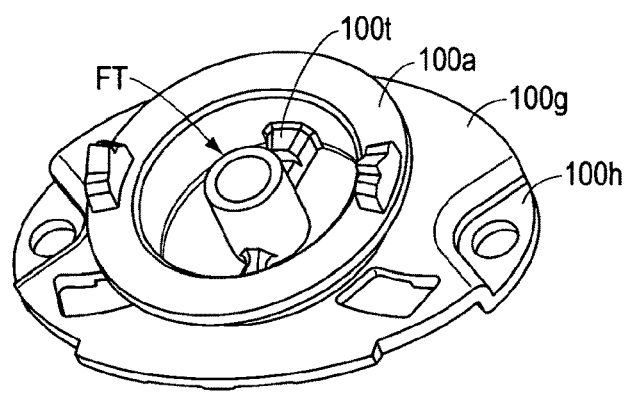
FIG. 71
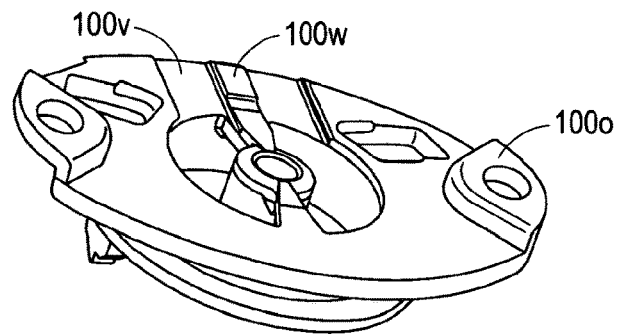
FIG. 72

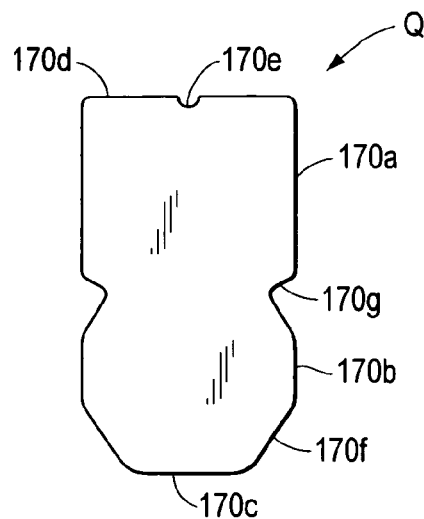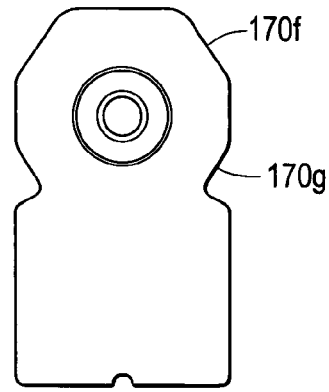
FIG 108  FIG 110
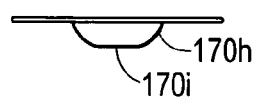
FIG 109
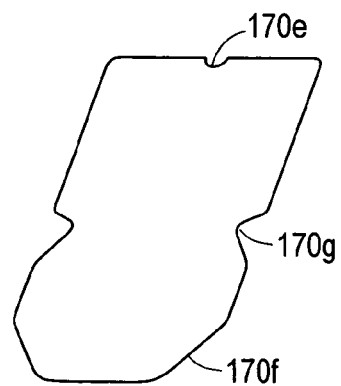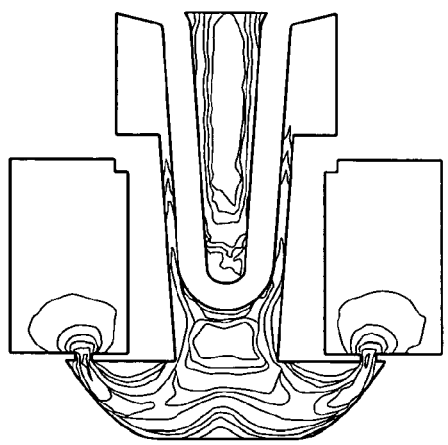
FIG 111  FIG 112

FIG 126
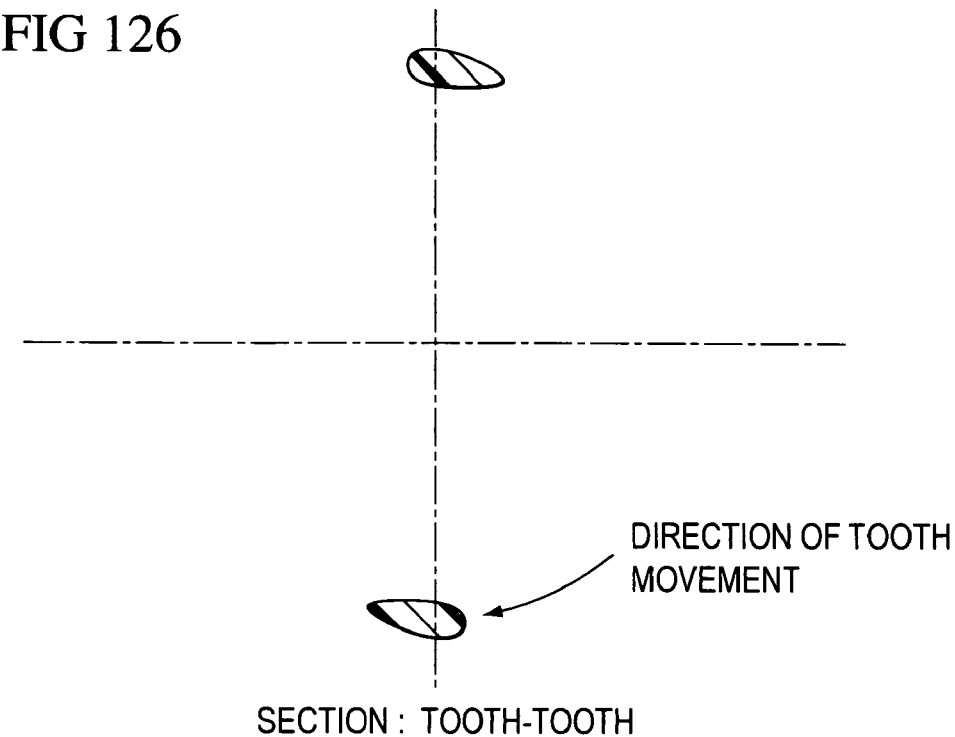
SECTION : TOOTH-TOOTH
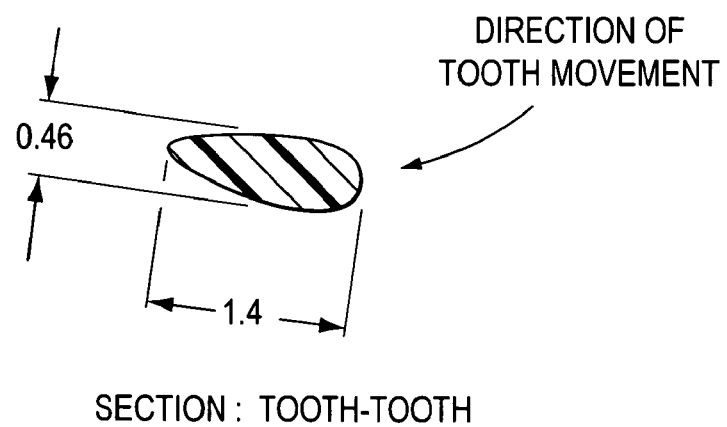
SECTION : TOOTH-TOOTH
FIG 127

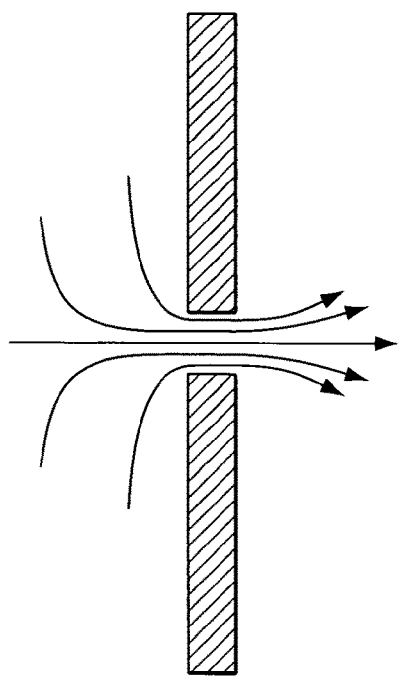
FIG 172
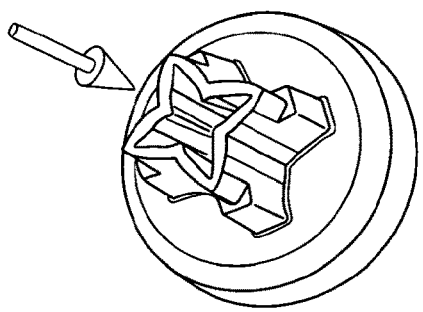 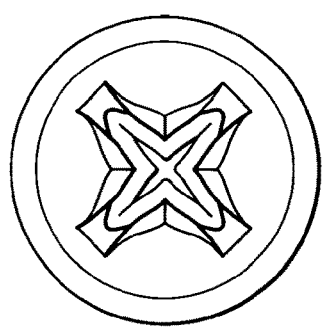
FIG 173  FIG 174

POWDER DISPERSION APPARATUS, METHOD OF MAKING AND USING THE APPARATUS, AND COMPONENTS THAT CAN BE USED ON THE APPARATUS AND OTHER DEVICES

CROSS-REFERENCE TO RELATED APPLICATIONS

The present application claims priority to and expressly incorporates by reference herein the entire disclosures of U.S. Application No. 60/854,601, filed Oct. 25, 2006, and U.S. Application No. 60/906,977, filed Mar. 13, 2007.

BACKGROUND OF THE INVENTION

1. Field of the Invention

The present invention relates generally to methods and apparatuses for the pulmonary delivery of a composition. In one aspect, the invention relates to methods and apparatuses for dispersing dry powder medicaments for inhalation by a patient. The invention is also directed to elements or aspects of the apparatuses as noted; such aspects include receptacle puncturing mechanisms, deocculsion devices, receptacle impacting devices, and receptacle lock devices or systems. Such elements or aspects can be used in apparatuses, including for example, apparatuses for pulmonary delivery of a composition.

2. Discussion of Background Information

Effective delivery to a patient is an important aspect of any successful drug therapy. Various routes of delivery exist, and each has its own advantages and disadvantages. Oral drug delivery of pills, capsules, elixirs, and the like, is perhaps the most convenient method, but many drugs are degraded in the digestive tract before they can be absorbed. Such degradation can be particularly problematic with protein drugs which can be rapidly degraded by proteolytic enzymes in the digestive tract. Subcutaneous injection is frequently an effective route for systemic drug delivery, including the delivery of proteins, but generally suffers from low patient acceptance. Since injection of drugs, such as insulin, one or more times a day can be a source of poor patient compliance, a variety of alternative routes of administration have also been developed, including transdermal, intranasal, intrarectal, intravaginal, and pulmonary delivery.

Of particular interest to the present invention, pulmonary drug delivery involves inhalation of a drug, such as in a dispersion or aerosol, by the patient so that active drug can reach the distal (alveolar) regions of the lung. It has been found that certain drugs are readily absorbed through the alveolar region directly into blood circulation. Pulmonary delivery is particularly promising for the delivery of proteins and polypeptides which are difficult to deliver by other routes of administration. Such pulmonary delivery is effective both for systemic delivery and for localized delivery to treat diseases of the lungs.

Pulmonary drug delivery (including both systemic and local) can itself be achieved by different approaches, including liquid nebulizers, pressurized metered dose inhalers (pMDI's), and dry powder dispersion devices. Dry powder dispersion devices are particularly promising for delivering protein and polypeptide drugs which may be readily formulated as dry powders. Many otherwise labile proteins and polypeptides may be stably stored as lyophilized or spray-dried powders by themselves or in combination with suitable powder carriers. The ability to deliver proteins and polypeptides as dry powders, however, can be difficult in certain respects. The dosage of some protein and polypeptide drugs is often important so dry powder delivery systems are ideally able to accurately, precisely, repeatedly, deliver the intended amount of drug. Moreover, many proteins and polypeptides are quite expensive, typically being many times more costly than conventional drugs on a per-dose basis. Thus, the ability to efficiently deliver the dry powders to the target region of the lung with a minimal loss of drug is important. It is further desirable that powder agglomerates present in the dry powder be sufficiently broken up prior to inhalation by the patient to increase the likelihood of effective systemic absorption or other pulmonary delivery.

A particularly promising approach for the pulmonary delivery of dry powder drugs utilizes a hand-held device with a pump or other source of pressurized gas. A selected amount of the pressurized gas is abruptly released through a powder dispersion device, such as a Venturi tube, and the dispersed powder made available for patient inhalation. Another typical characteristic for hand-held and other powder delivery devices is high dosage concentration. It is important that the concentration of drug in the bolus of gas be relatively high to reduce the number of breaths and/or volume of each breath required to achieve a total dosage. The ability to achieve both adequate dispersion and small dispersed volumes is a significant technical challenge.

Dry powder dispersion devices for medicaments are described in a number of patent documents. For example, U.S. Pat. No. 3,921,637 describes a manual pump with needles for piercing through a single capsule of powdered medicine. The use of multiple receptacle disks or strips of medication is described, for example, in EP 467172 (in which a reciprocatable piercing mechanism is used to pierce through opposed surfaces of a blister pack); WO91/02558; WO93/09832; WO94/08522; U.S. Pat. Nos. 4,627,432; 4,811,731; 5,035,237; 5,048,514; 4,446,862; and 3,425,600. Other patents, which show puncturing of single medication capsules, include U.S. Pat. Nos. 4,338,931; 3,991,761; 4,249,526; 4,069,819; 4,995,385; 4,889,114; and 4,884,565; and EP 469814. WO90/07351 describes a hand-held pump device with a loose powder reservoir. Other devices include those described in U.S. Pat. Nos. 6,109,261 and 6,606,992; and U.S. Published App. No. 2004/0000309. The entire disclosure of each of these documents is hereby expressly incorporated by reference.

U.S. Pat. No. 6,257,233, for example, describes various apparatuses and methods for aerosolizing a powdered medicament. In one exemplary embodiment, an apparatus includes a pressurization cylinder and a piston which is slidable within the cylinder to pressurize a gas. A handle is coupled to the piston and is movable between an extended position and a home position to pressurize the gas. An aerosolizing mechanism is included and is configured to aerosolize a powdered medicament that is held within a receptacle with pressurized gas from the cylinder. A carriage assembly is included to receive the receptacle and to couple the receptacle to the aerosolizing mechanism. A first and a second interlock are operably engageable with the carriage assembly to prevent coupling of the receptacle with the aerosolization mechanism. The first interlock is released to allow movement of the carriage upon movement of the handle to the extended position. The second interlock remains engaged if the receptacle is only partially inserted into the carriage assembly. With the release of Exubera™ inhaleable insulin, which utilizes a device similar to that described in U.S. Pat. No. 6,257,233, an alternative is available to injections for the first time.

Devices are also available which utilize a puncturing system wherein a blade mechanism descends into a foil, cuts openings in the foil, and then stays in place during evacuation. Such a device is disclosed in U.S. Pat. No. 6,668,827, the disclosure of which is hereby expressly incorporated by reference in its entirety. The cutters described in that patent create plural concentric arc-shaped cut openings in the blister foil and simultaneously rolling up a small strip of foil along the leading edge of the cutter tooth. They are designed to descend into the blister, rotate, and remain in the blister during blister evacuation. They are then reversed in rotation and retracted from the blister.

Other devices that use drug packages that are sealed with foil include the Diskhaler® and the Diskus®. The Diskhaler® drives a long plastic tooth through the entire drug package, retracting it before inhalation. This creates an additional step to retract the tooth, ends up creating a large and inconsistent hole through the drug package, and produces variable dose due to airflow variation and powder losses through the large hole. The Diskus® peels away the thin lidstock, revealing the entire tub containing the drug powder. The act of peeling back the lidstock creates vibrations in the drug package, which create a risk of vibrating powder out of the drug package and reducing the available dose.

The principle of puncturing the foil of a blister pack using a blunt member and then forming arc-shaped openings using a plowing effect is disclosed in U.S. Pat. No. 5,833,071, the disclosure of which is hereby expressly incorporated by reference in its entirety.

Commercially available passive dry powder inhalers (DPIs) often utilize large carrier particles, typically lactose particles, intermixed with fine powder medicament in order to facilitate aerosolization. Such lactose blends produce impaction of the large lactose particles in the user's upper respiratory tract (URT) and greatly limit the practical size of the deliverable dose. Further limitations of commercially available passive DPIs are their variability of emitted dose (ED) and fine particle dose (FPD), which are both highly dependent upon user's inhalation flow rate (Q) and flow increase rate (FIR) at the beginning of the inhalation maneuver.

There remains, however, a need for improved inhalers. For example, there is a need for consistent pulmonary delivery of a dry powder medicament. There is also a need for efficient aerosolization of dry powder medicament. Still another need is to control flow rate through inhalers in a manner that facilitates both aerosolization of dry powder medicament and consistent lung deposition. Yet another need is for improved passive dry powder inhaler (DPI) device having the ability to produce high emitted dose (ED) and fine particle dose (FPD) consistently across a highly variable user population. It would therefore be desirable to provide methods and systems for the dispersion of dry powder protein, polypeptide, and other drugs. Such methods and systems may have applications other than for use in an inhaler.

SUMMARY OF THE INVENTION

Accordingly, the present invention provides a variety of mechanisms and methods, which may be used in pulmonary delivery of substances, such as drugs, and in other applications. Other features and advantages of the present invention will be set forth in the description of invention that follows, and in part will be apparent from the description or may be learned by practice of the invention. The invention will be realized and attained by the mechanisms and methods particularly pointed out in the written description and claims hereof.

Thus, aspects of the invention relate generally to methods and apparatuses for the pulmonary delivery of a substance such as drugs. In embodiments, the present invention relates to methods and apparatuses for dispersing dry powder medicaments for inhalation by a patient.

Embodiments also include elements such as receptacle puncturing mechanisms, deoccluding elements, receptacle impacting elements, and receptacle lock elements. Such features or elements can be used alone or in combination with one or more other features or elements. Such features and elements can be used in apparatuses for the pulmonary delivery of drugs, or in any other apparatus, including those not intended for delivery of drugs.

In one aspect, the present invention involves an apparatus comprising a support for supporting a receptacle, an outlet, and a feed tube communicating with the outlet. The apparatus also includes a mechanism configured to create at least one opening in a wall of the receptacle, the mechanism comprising a blade having a leading edge, wherein the leading edge comprises an elliptical leading edge having a rho value from 0.1 to 0.5.

In another aspect, the present invention involves an apparatus comprising a support for supporting a receptacle, an outlet, and a feed tube communicating with the outlet. The apparatus also includes a deoccluding device permanently arranged within the feed tube.

In still another aspect, the present invention involves an apparatus comprising a support for supporting a receptacle, an outlet, and a feed tube communicating with the outlet. The apparatus also includes a receptacle impacting device that has a plurality of stable positions such that the receptacle impacting device is automatically cocking.

In yet another aspect, the present invention involves an apparatus comprising a support for supporting a receptacle having an outline comprising a first pair of sides and a second pair of sides that are shorter than the first pair of sides, the first pair of sides comprising notches. The apparatus also includes an outlet and a feed tube communicating with the outlet. Further, the apparatus includes a receptacle lock system that interacts with the notches of the receptacle.

In another aspect, the present invention involves a method of opening a receptacle using an apparatus. The method includes inserting a receptacle containing a powder into the apparatus. The method further includes creating, with a mechanism configured to create at least one opening in a wall of the receptacle, a puncture in the wall and then a tear in the wall, wherein the tearing bends torn edges of the wall inwardly into the receptacle.

In a further aspect, the present invention involves using an apparatus. The method includes inserting a receptacle containing a powder into the apparatus, puncturing the receptacle, and deoccluding a feed tube of the apparatus.

In yet another aspect, the present invention involves a method of using an apparatus. The method includes inserting a receptacle containing a powder into the apparatus and impacting the receptacle with a receptacle impacting device.

In another aspect, the present invention involves a mechanism configured to create at least one opening in a wall of a receptacle. The mechanism includes a support and at least one protruding member arranged on the support. The at least one protruding member comprising a blade having a leading edge, wherein the leading edge comprises an elliptical leading edge having a rho value from 0.1 to 0.5.

In a further aspect, the present invention involves a deoccluding device adapted to remove a powder residue from an inner surface of a tube. The device includes a first portion structured and arranged to deocclude an inner surface of a tube by rotating and descending into the tube, wherein the first portion does not contact the inner surface of the tube.

In still another aspect, the present invention involves a receptacle impacting device. The receptacle impacting device includes a support portion and a plurality of arms projecting from the support portion. Each of the plurality of arms is structured and arranged to impact a receptacle.

In yet another aspect, the present invention includes a receptacle lock system structured and arranged to receive a receptacle of predetermined configuration. The system includes a device that moves from a locked position to an unlocked position based on a position of the receptacle, wherein the receptacle comprises an outline comprising a first pair of sides and a second pair of sides that are shorter than the first pair of sides, the first pair of sides comprising notches, and wherein the receptacle lock system interacts with the notches of the receptacle.

In another aspect, the present invention involves a kit including (1) an apparatus; and (2) at least one powder-containing receptacle. The apparatus comprises a support for supporting a receptacle, an outlet, and a feed tube communicating with the outlet. The apparatus also includes at least one of:
  a mechanism configured to create at least one opening in a wall of a receptacle, the mechanism comprising a blade having a leading edge, wherein the leading edge comprises an elliptical leading edge having a rho value from 0.1 to 0.5;
  a deoccluding device permanently arranged within the feed tube;
  a receptacle impacting device that has a plurality of stable positions such that the receptacle impacting device is automatically cocking; and
  a receptacle lock system that interacts with notches of the receptacle wherein the receptacle has an outline comprising a first pair of sides and a second pair of sides that are shorter than the first pair of sides, the first pair of sides comprising the notches; and In still another aspect, the present invention includes a combination comprising (1) an apparatus; and (2) a powder-containing receptacle inserted in the apparatus. The apparatus comprises a support for supporting a receptacle, an outlet, a feed tube communicating with the outlet, and at least one of:
  i) a mechanism configured to create at least one opening in a wall of a receptacle, the mechanism comprising a blade having a leading edge, wherein the leading edge comprises an elliptical leading edge having a rho value from 0.1 to 0.5;
  ii) a deoccluding device permanently arranged within the feed tube;
  iii) a receptacle impacting device that has a plurality of stable positions such that the receptacle impacting device is automatically cocking; and
  iv) a receptacle lock system that interacts with notches of the receptacle wherein the receptacle has an outline comprising a first pair of sides and a second pair of sides that are shorter than the first pair of sides, the first pair of sides comprising the notches.

In still another aspect, the present invention involves an apparatus comprising an outlet, a feed tube communicating with the outlet, a mechanism configured to create at least one opening in a wall of a receptacle, a deoccluding device arranged within the feed tube, a receptacle impacting device, and a receptacle lock system.

In a further aspect, the present invention involves a method of aerosolizing a powder using an apparatus. The method includes inserting a receptacle containing a powder into the apparatus, rotating one portion of a housing relative to another portion of the housing, and inhaling on a mouthpiece of the apparatus.

In another aspect, the present invention involves a kit comprising components for assembling an apparatus. The apparatus includes at least an outlet, a feed tube communicating with the outlet, a mechanism configured to create at least one opening in a wall of a receptacle, a deoccluding device arranged within the feed tube, a receptacle impacting device, a receptacle lock system, and written instructions for assembling the components into an apparatus for aerosolizing a powder.

In still another aspect, the present invention involves an apparatus comprising a support for supporting a receptacle, an outlet, and an internally flared feed tube communicating with the outlet. The apparatus also includes a mechanism configured to create at least one opening in a wall of the receptacle, the mechanism comprising a blade having a leading edge, wherein the leading edge comprises an elliptical leading edge having a rho value from 0.1 to 0.5.

In yet another aspect, the present invention involves an apparatus comprising a support for supporting a receptacle, an outlet, and an internally flared feed tube communicating with the outlet. The apparatus also includes a mechanism configured to create at least one opening in a wall of the receptacle, the mechanism comprising a blade having a leading edge, wherein the leading edge comprises an elliptical leading edge having a rho value from 0.1 to 0.5.

In still another aspect, the present invention involves a method of administering a drug-containing powder via inhalation. The method include inserting a powder-containing receptacle into an apparatus for aerosolizing a powder, the apparatus comprising a support for supporting a receptacle, an outlet, a feed tube providing communication between the receptacle and the outlet, and at least one of:
  i) a mechanism configured to create at least one opening in a wall of the receptacle, the mechanism comprising a blade having a leading edge, wherein the leading edge comprises an elliptical leading edge having a rho value from 0.1 to 0.5;
  ii) a deoccluding device arranged within the feed tube;
  iii) a receptacle impacting device; and
  iv) a receptacle lock system; and
  producing at least one opening in the powder-containing receptacle; and
  inhaling on a mouthpiece of the apparatus, whereby powder in the powder-containing receptacle is administered.

In still another aspect, the present invention involves an apparatus comprising a support for supporting a receptacle, an outlet, and a feed tube communicating with the outlet. The apparatus also includes a valve positioned between the receptacle and the outlet such that air flow from the receptacle to the outlet passes through the valve.

In yet another aspect, the present invention involves a cutter mechanism. The cutter mechanism includes a plastic blade having a leading edge, wherein the leading edge comprises an elliptical leading edge having a rho value from 0.1 to 0.5.

In still another aspect, the present invention involves an apparatus including a support for supporting a receptacle, an outlet, and a feed tube communicating with the outlet. The apparatus also includes a puncturing device disposed in the feed tube, wherein the puncturing device is moveable relative to the feed tube to puncture the receptacle.

In yet another aspect, the present invention involves a receptacle. The receptacle includes a lower foil laminate comprising a blister for holding powder and an upper foil laminate covering the lower foil laminate, wherein the receptacle comprises a rear portion having two sides perpendicular to a third side, a middle portion comprising notches, and a tapered front portion.

BRIEF DESCRIPTION OF THE DRAWINGS

FIG. 3 shows a side perspective view of an embodiment of the invention and illustrates how the cover can be removed by lifting it vertically off of the device;

FIG. 4 shows another side perspective view of the embodiment of FIG. 3 and illustrates how the receptacle can be inserted into the front side of the device after the cover has been removed. During insertion of the receptacle, the lock system is engaged and the receptacle impacting system is activated;

FIG. 5 shows another side perspective view of the embodiment of FIG. 4 and illustrates how the mouth piece or upper portion of the device can be rotated relative to a lower portion of the device after the receptacle has been properly inserted. Rotation of 180 degrees automatically causes puncturing and tearing of both the inlet and outlet openings in the receptacle and deoccluding of the feed tube;

FIG. 6 shows another side perspective view of the embodiment of FIG. 5 and illustrates how, after the mouth piece is rotated 180 degrees, the device can be used by the user for inhalation;

FIG. 7 shows another side perspective view of the embodiment of FIG. 6 and illustrates how the receptacle can be removed;

FIG. 8 shows another side perspective view of the embodiment of FIG. 7 and illustrates how the cover can be placed back onto the device after use;

FIG. 44 shows a top view of the trigger shown in FIG. 9;

FIG. 45 shows a front side view of the trigger shown in FIG. 44;

FIG. 46 shows a top front perspective view of the trigger shown in FIG. 44;

FIG. 47 shows a rear bottom perspective view of the trigger shown in FIG. 44;

FIG. 56 shows a bottom view of the cutter mechanism shown in FIG. 53;

FIG. 57 shows a right side view of the cutter mechanism shown in FIG. 53;

FIG. 58 shows a top front perspective view of the cutter mechanism shown in FIG. 53;

FIG. 59 shows a bottom left side perspective view of the cutter mechanism shown in FIG. 53;

FIG. 69 shows a bottom view of the lower bearing member shown in FIG. 66;

FIG. 70 shows a right side view of the lower bearing member shown in FIG. 66;

FIG. 71 shows a top right front perspective view of the lower bearing member shown in FIG. 66;

FIG. 72 shows a bottom rear side perspective view of the lower bearing member shown in FIG. 66;

FIG. 108 shows a top view of the receptacle shown in FIG. 9;

FIG. 109 shows a front side view of the receptacle shown in FIG. 108;

FIG. 110 shows a bottom view of the receptacle shown in FIG. 108;

FIG. 111 shows a top right front side perspective view of the receptacle shown in FIG. 108;

FIG. 112 shows a partial flow diagram illustrating air flow into the receptacle from the inlet openings towards the center of the receptacle tub, and then up through the center opening of the receptacle and then finally up through the feed tube and past the deoccluding member;

FIG. 126 shows a section view of FIG. 124 and shows a rotational direction of movement of the teeth which will form the inlet openings in the receptacle;

FIG. 127 shows one of the teeth of FIG. 126 and non-limiting cross-sectional height and width dimensions in millimeters thereof;

FIG. 129 shows a perspective view of a mouthpiece of the embodiment shown in FIG. 128;

FIG. 130 shows a perspective view of an adapter of the embodiment shown in FIG. 128;

FIG. 131 shows a perspective view of a deoccluding device of the embodiment shown in FIG. 128;

FIG. 132 shows a perspective view of a cutter mechanism of the embodiment shown in FIG. 128;

FIG. 133 shows a perspective view of a bearing member of the embodiment shown in FIG. 128;

FIG. 134 shows a perspective view of a body of the embodiment shown in FIG. 128;

FIG. 135 shows a perspective view of a tray of the embodiment shown in FIG. 128;

FIG. 136 shows a perspective view of a receptacle impacting member of the embodiment shown in FIG. 128;

FIG. 137 shows a perspective view of a baseplate of the embodiment shown in FIG. 128;

FIG. 138 shows a perspective view of a skirt member of the embodiment shown in FIG. 128;

FIGS. 139-178 shows various diagrams and drawings relating to air flow characteristics of an apparatus of the invention.

FIG. 179 shows the rho dimension of a conic segment PQ.

DETAILED DESCRIPTION OF THE INVENTION

Figure 1:
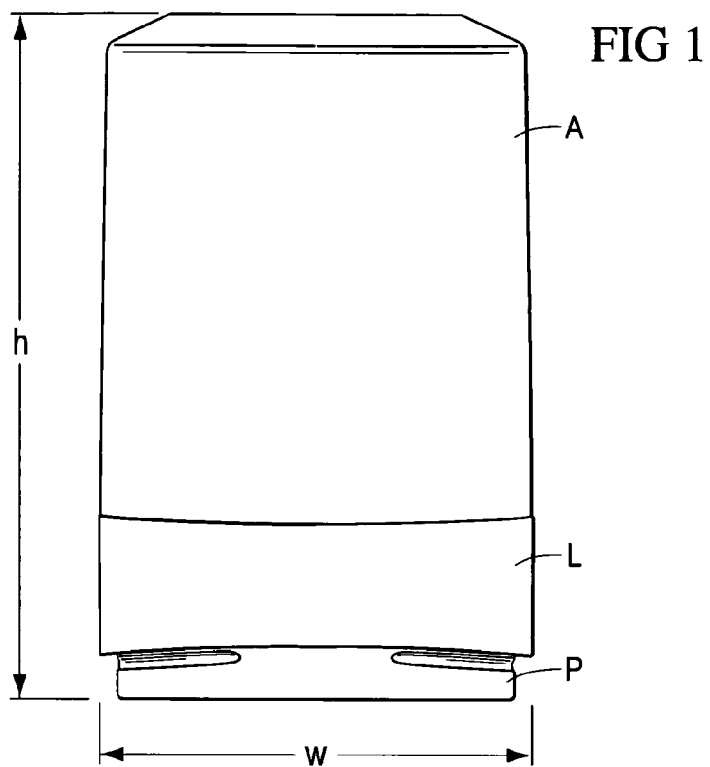
FIG. 1 shows a front side view of one embodiment of the invention and includes an overall height dimension and an overall width dimension.

The invention is directed to methods and apparatuses for the pulmonary delivery of a substance such as drugs. More particularly, the present invention relates to a method and apparatus for dispersing dry powder medicaments for inhalation by a patient. The invention is also directed to devices, which can be used in or on such devices such as a receptacle puncturing mechanism, a deoccluding device, a receptacle impacting device, and a receptacle lock device or system. Such features can be used alone or in combination with an apparatus according to the invention.

Unless otherwise stated, a reference to a compound or component includes the compound or component by itself, as well as in combination with other compounds or components, such as mixtures of compounds. As used herein, the singular forms "a," "an," and "the" include the plural reference unless the context clearly dictates otherwise. Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values within that range. For example, if a range is from about 1 to about 50, it is deemed to include, for example, 1, 7, 34, 46.1, 23.7, or any other value within the range.

Before further discussion, a definition of the following terms will aid in the understanding of the present invention.
Definitions The terms used in this disclosure are defined as follows unless otherwise indicated. Standard terms are to be given their ordinary and customary meaning as understood by those of ordinary skill in the art, unless expressly defined herein.

A composition that is "suitable for pulmonary delivery" refers to a composition that is capable of being aerosolized and inhaled by a subject so that a portion of the aerosolized particles reaches the lungs, e.g., to permit entry into the alveoli and into the blood. Such a composition may be considered "respirable" or "inhaleable."

An "aerosolized" composition contains liquid or solid particles that are suspended in a gas (typically air), typically as a result of actuation (or firing) of an inhalation device. A passive dry powder inhaler would be actuated by a user's breath.

A "dry powder inhaler" is a device that is loaded with a unit dose of the drug in powder form. Generally, the inhaler is activated by taking a breath. For example, a capsule or blister is punctured and the powder is dispersed so that it can be inhaled, e.g., in a "Spinhaler" or "Diskhaler." "Turbohalers" are fitted with canisters that deliver measured doses of the drug in powder form.

As used herein, the term "emitted dose" or "ED" refers to an indication of the delivery of dry powder from an inhaler device after an actuation or dispersion event from a powder unit or reservoir. ED is defined as the ratio of the dose delivered by an inhaler device to the nominal dose (i.e., the mass of powder per unit dose placed into a suitable inhaler device prior to firing). The ED is an experimentally determined amount, and may be determined using an in vitro device set up which mimics patient dosing. To determine an ED value, as used herein, dry powder is placed into a device to be tested. The device is actuated (e.g., by inserting a blister, rotating a mouthpiece of the device, and applying a 30 L/min vacuum source to an exit of the mouthpiece), dispersing the powder. The resulting aerosol cloud is then drawn from the device by vacuum (30 L/min) for 2.5 seconds after actuation, where it is captured on a tared glass fiber filter (Gelman, 47 mm diameter) attached to the device mouthpiece. The amount of powder that reaches the filter constitutes the delivered dose. For example, for a capsule containing 5 mg of dry powder that is placed into an inhalation device, if dispersion of the powder results in the recovery of 4 mg of powder on a tared filter as described above, then the ED for the dry powder composition is 80% (=4 mg (delivered dose)/5 mg (nominal dose)).

A composition in "dry powder form" is a powder composition that typically contains less than about 20 wt % moisture.

As used herein, "mass median diameter" or "MMD" refers to the median diameter of a plurality of particles, typically in a polydisperse particle population, i.e., consisting of a range of particle sizes. MMD values as reported herein are determined by laser diffraction (Sympatec Helos, Clausthal-Zellerfeld, Germany), unless the context indicates otherwise. Typically, powder samples are added directly to the feeder funnel of the Sympatec RODOS dry powder dispersion unit. This can be achieved manually or by agitating mechanically from the end of a VIBRI vibratory feeder element. Samples are dispersed to primary particles via application of pressurized air (2 to 4 bar), with vacuum depression (suction) maximized for a given dispersion pressure. Dispersed particles are probed with a 632.8 nm laser beam that intersects the dispersed particles' trajectory at right angles. Laser light scattered from the ensemble of particles is imaged onto a concentric array of photomultiplier detector elements using a reverse-Fourier lens assembly. Scattered light is acquired in time-slices of 5 ms. Particle size distributions are back-calculated from the scattered light spatial/intensity distribution using an algorithm.

"Mass median aerodynamic diameter," or "MMAD," is a measure of the aerodynamic size of a dispersed particle. The aerodynamic diameter is used to describe an aerosolized powder in terms of its settling behavior, and is the diameter of a unit density sphere having the same settling velocity, in air, as the particle. The aerodynamic diameter encompasses particle shape, density, and physical size of a particle. As used herein, MMAD refers to the midpoint or median of the aerodynamic particle size distribution of an aerosolized powder determined by cascade impaction at standard conditions (20° C.; 40% RH) using the device to be tested.

"Fine particle fraction" is the fraction of particles with an aerodynamic diameter that is less than 5 microns (μm). Where specified, the fine particle fraction may also refer to the fraction of particles with an aerodynamic diameter that is less than 3.3 microns.

"Fine particle dose" is the amount of particles with an aerodynamic diameter that is less than 5 microns (μm). Where specified, the fine particle dose may also refer to the amount of particles with an aerodynamic diameter that is less than 3.3 microns.

"Receptacle" is a container. For example, a receptacle may be a unit dose receptacle, or it may be a reservoir having multiple doses. Examples of unit dose receptacles include blister packs and capsules. In certain embodiments, the receptacle may be removable from an inhaler device, or the receptacle may be part of an inhaler device. The receptacle typically comprises any material that allows tearing, e.g., a controlled tear, such as foil-plastic laminates.

"Tearing" means to pull apart. A blade may be used to tear a material so long as the material pulls apart at a distance from a leading edge of the blade.

"Cutting" means to divide. A blade may be used to cut a material such that a leading edge of the blade contacts the material to be cut.

Figure 179:
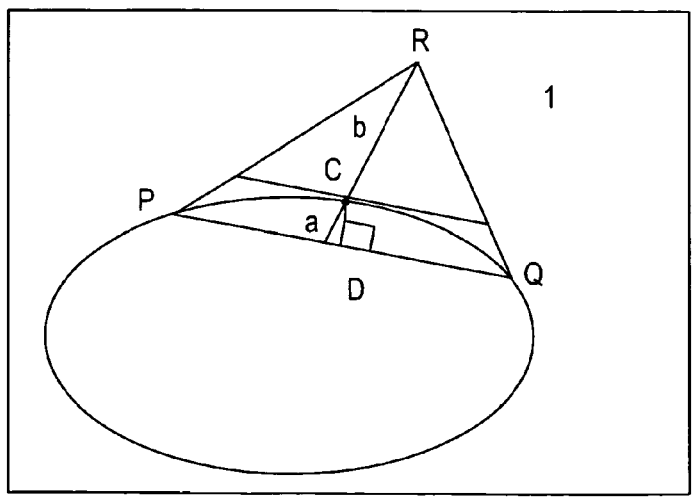

The "rho" dimension of a conic segment PQ defines the shape of the conic (see FIG. 179). The rho dimension specifies a ratio along a vector from the chord (PQ) through a point C to the vertex (R). Point C is at the maximum distance (CD), measured by a normal from the chord PQ to the conic segment PQ. Rho is a/(a+b).

Cutter Mechanism

One aspect of the invention relates to a mechanism configured to cut or tear materials. This aspect of the present invention may be used for most any application in which cutting or tearing is desired. As one example, the blades of the present invention may be used in the food packaging field. As another example, the mechanism may be configured to create at least one air inlet opening in a wall of a receptacle by causing a puncture in the wall and also causing a controlled tearing of the wall, whereby the tearing may bend torn edges of the wall inwardly (see e.g., FIG. 102). According to one non-limiting embodiment of the invention, such a mechanism can be utilized in the apparatus and/or method for aerosolizing a powdered medicament as described herein (see e.g., FIGS. 1-9, 24-27, and 114-123). The receptacle can take the form of a primary drug package which is sealed against moisture using a foil that spans the tub containing the powder (see e.g., FIGS. 108-111). To release the powder for inhalation by a user in an effective manner, puncturing of the foil in a substantially controlled fashion is desired. This control can be performed effectively using one or more substantially tooth-shaped members (see e.g., FIGS. 126-127).

The tooth (or teeth), which performs the controlled puncturing, generally first moves into engagement with the package (e.g., by moving the tooth toward the package or by moving the package toward the tooth). Preferably, the receptacle remains static (neither raised nor lowered) in the apparatus and instead the receptacle puncturing mechanism moves vertically to a lower position, wherein the receptacle is punctured, and also to an upper or retracted position. This degree of movement should be sufficient to cause the foil of the package to be punctured. This generally occurs when the foil is locally, i.e., in the vicinity of the tooth, stretched beyond its ability to resist plastic deformation. When this occurs, the tooth punctures or tears through the foil and causes the torn edges to bend inwardly, i.e., into the tub of the receptacle. Alternatively, in other embodiments, the torn edges or flaps bend outwardly, or one edge or flap can go inwardly and the other outwardly. With the penetration depth of the tooth maintained, the tooth can then be moved across the foil surface in any geometric pattern whereby a side leading edge of the tooth essentially separates the foil. In this embodiment the tooth is moved in an arc-shaped movement and for a desired arc-angle. The arc-angle is typically at least about 90° or more, such as at least about 100°, 110°, 120°, 130°, 140°, 150°, 160°, 170°, or 180°, and may range from, e.g., from 40° to 350°, such as 50° to 300°, 60° to 250°, 70° to 200°, or 80° to 150°. In some cases, the ideal would be a complete 360° cut/tear, except that the central portion of the foil would come loose. Typically, the goal is to make as long of a cut/tear as possible, with just enough to keep the lidstock from coming apart. In some cases, there is also a need to raise the blades over spoke-like members that hold the feed tube in place. In addition to arc-shaped cuts or rotary tears, the blades of the present invention can be used to make cuts/tears of different shapes. For instance, the blades may be used to make linear cuts/tears.

Figure 102:
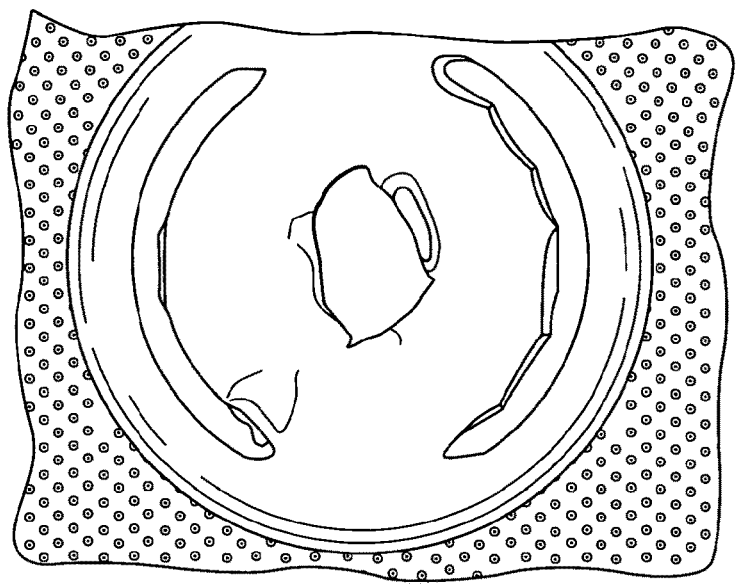
FIG. 102 shows a top view of a punctured foil lid of a receptacle after being used in an inhalation apparatus of the type described herein and illustrates the two curved inlet openings and the center outlet opening.

By way of non-limiting example, FIGS. 126-127 illustrate such tooth movement and FIG. 102 illustrates two arc-shaped inlet openings formed by two teeth of the type shown in FIGS. 126-127. The tooth or teeth can be retracted or caused to move away from the package in a linear or curvilinear fashion. This movement forms one or more arc-shaped inlet openings in the package or receptacle whereby the torn edges of the opening(s) are bent inwardly, i.e., into the receptacle, thereby ensuring that the edges will not substantially obstruct the flow of air into the receptacle when the receptacle is thereafter evacuated using the apparatus. This puncturing system, for example, provides advantages over a cutter mechanism that descends into the foil, cuts openings in the foil and then stays in place during evacuation. In some embodiments of this puncturing system, the user is aware of rotation but is not aware of the telescoping of the cutter mechanism, which occurs internally.

Although less preferable, the invention, however, does not preclude using cutter/opening systems of the type used in Diskhaler® and Diskus® (see, e.g., U.S. Pat. Nos. 4,811,731; 5,035,237; and 5,590,645, which are incorporated herein by reference) in an apparatus of the type disclosed herein; particularly in combination with one or more of the other features of the apparatus described herein.

In one preferred embodiment of the invention, one or more teeth creates one or more arc-shaped inlet openings in the foil using a plowing effect. As explained above, this creates a controlled tear of the foil and bends the cut or torn edges into the package. For arc-shaped and other cuts/tears, the tooth is designed to penetrate and separate the foil in such a way that it produces a very smooth edge. This edge has a Hausdorff dimension of no greater than 1.5, such as less than 1.2. Another advantage of this type of cutting/tearing is that it minimizes chances for loose foil or foil particulate to potentially break away and enter the drug path of the device and possibly enter the user's lungs. The tooth essentially creates a consistent and precise tear (producing openings of substantially reproducible size and shape) in the foil, which also contributes to reducing the overall variability in the aerosol performance of the device. This also allows the opening(s) in the foil to play an active role in the effective evacuation of the blister or receptacle by allowing and/or directing the airflow into the drug package more efficiently. Another advantage of forming the puncturing member in the shape of a tooth, is that such shapes can be readily made by injection molding and using plastic material. As a result, the tooth or teeth can be made with great consistency, at relatively low cost, and in high volume manufacturing. The tooth shape can be such that it is in the line of draw of the injection molding tool, which creates a simpler and more consistent component manufacture. A non-limiting example of the tooth shape is shown in FIGS. 124-127, which illustrate a cutter mechanism having two teeth.

It should be noted that while in some embodiments, puncturing occurs first, followed by tearing, these actions can occur simultaneously. For example, a desired opening can be created by a single puncturing movement, producing a desired shape. Alternatively, the puncturing and tearing can occur essentially simultaneously by a mechanism that lowers a leading edge into a material to be cut or torn while at the same time moving through a cutting or tearing arc.

In a preferred embodiment of the invention, the shape of the tooth at the plane where it cuts or tears through the material to be cut or torn, e.g., foil, is a balance of not too sharp (such that it cuts, not tears, but is subject to wear over time) and not too blunt (such that it creates an uncontrolled tear in the material to be cut or torn). For instance, an elliptical leading edge of the tooth may have a rho value from 0.1 to 1.0, such as from 0.2 to 0.9, 0.3 to 0.8, or 0.4 to 0.7.

It has been found that such a shape is simple to manufacture and creates consistent and precise openings in the material to be cut or torn, e.g., foil lidstock. This shape is also robust enough, even when made of standard injection molded plastic materials, to allow a long use life for the device. Again, reference is made to FIGS. 126-127, which show a tooth shape having a rounded leading end for causing the tearing. In an alternative embodiment (not shown in the drawings), the tooth has two leading edges to allow bidirectional cutting or tearing.

For rotary cuts or tears, the orientation of the tooth has been optimized. For example, the yaw of the tooth typically ranges from 0-12°, 4-10°, 6-8°, away from center. Although the yaw of the tooth is not critical, the finding that yaw is ideally 6-8° away from center is a surprising result. If the yaw is not within this ideal range, the tear tends to be more ruffled on one side.

The tooth is particularly useful in puncturing a drug package receptacle that has a foil-plastic laminate lid covering a tub that is roughly hemispherical in shape. Non-limiting examples of such receptacles are disclosed in U.S. Pat. No. 6,668,827, the disclosure of which is hereby expressly incorporated by reference in its entirety. Other non-limiting examples of the receptacle are shown in FIGS. 108-111. The top of the drug package is generally planar and is sealed with a foil lidstock over its top surface. The drug package receptacle is inserted into the apparatus (see e.g., FIGS. 4 and 104-107), and the apparatus is manipulated to automatically open the drug package when a rotary motion is applied to two halves or housing parts of the apparatus (see, e.g., FIG. 5). The actuation of the apparatus creates several holes in the foil lidstock (see, e.g., FIG. 102). Air inlet openings are formed to allow ambient air to enter the drug package (e.g., the two arc-shaped openings in FIG. 102). An exit opening is also formed to allow the drug-entrained air to exit the drug package (e.g., the central opening in FIG. 102). In some embodiments, tooth or teeth is/are used to cut or tear one or more arc-shaped air inlet openings by descending, e.g., rapidly, into the drug package, then moving through an arc, and then retracting completely out of the drug package. This movement takes place in the apparatus when the user rotates one housing part of the apparatus relative to another housing part. FIG. 5 shows one non-limiting way in which this can occur.

By way of non-limiting example, the shape of the tooth (or teeth) can have several specific features that enhance its function. The tip of the tooth(s) can be made to come to a point (see e.g., FIG. 124) to allow the tooth to efficiently pierce the foil as it descends into the drug package. The body of the tooth can have a constant or substantially uniform cross section (see e.g., FIGS. 126-127) over the expected range of interaction with the foil. The leading edge of the body of the tooth should preferably not be too sharp, so as to ensure that the edge will not wear unpredictably and possibly create debris. The leading edge of the tooth should also have a specific bluntness (e.g., a rounded configuration such as is shown in FIGS. 126-127) which ensures that the tooth cleaves the foil without causing it to bunch up as the tooth moves through the foil. The width of the body of the tooth can be designed to give the desired width of arc-shaped opening in the foil. Non-limiting size dimensions in millimeters and a shape for the tooth or teeth are shown in FIGS. 124-127.

As explained above, the tooth shape is also designed to allow it to be molded from injection-moldable plastics. The ability to mold the tooth or teeth with a support member (i.e., a member which supports the tooth), in e.g., plastic, can eliminate the need to separately affix and align the tooth or teeth in another member. This facilitates high volume manufacture. The use of plastic and the ability to integrate the tooth or teeth into another part can also result in more consistent performance and lower cost for the apparatus. The tooth shape also does not require any side pulls or other complications to the injection mold design. As such, the tool will require less maintenance over its lifetime. Non-limiting examples of a support member or cutter mechanism having such teeth are shown in FIGS. 53-59 and 124-125.

The blade or cutter mechanism of the present invention can be used in any device that is configured to cut or tear a thin layer, sheet, or film, such as a foil. The invention also contemplates utilizing the blade described herein on devices that include one or more features disclosed in WO2004/110539, WO03/086515, WO03/086516, WO03/086517, and U.S. Patent Application Publication Nos. 2005/0279356 and 2007/0068524, the disclosures of these documents are hereby expressly incorporated by reference in their entireties. For example, the cutter mechanism described herein (or portions thereof such as the tooth or teeth, e.g., plastic tooth or teeth) can be used in an inhaler described in WO 2004/110539. The cutter mechanism of the invention (or portions thereof such as the tooth or teeth) can also be used in an inhaler described in WO 03/086515, and more specifically can be used in place of the foil cutter (ref. No. 11 in WO 03/086515), whereby the disclosed device uses aspects of the instant invention to open a receptacle containing a powder and having a foil lid, e.g., by tearing the foil. The cutter mechanism described herein (or portions thereof such as the tooth or teeth, e.g., plastic tooth or teeth) can also be used in an inhaler described in WO 03/086516, and more specifically can be used in place of the foil cutter (ref. No. 11 in WO 03/086516), whereby the disclosed device uses aspects of the instant invention to open a receptacle containing a powder and having a foil lid, e.g., by tearing the foil. The cutter mechanism described herein (or portions thereof such as the tooth or teeth, e.g., plastic tooth or teeth) can still further also be used in an inhaler described in WO 03/086517, and more specifically can be used in place of the foil cutter (ref. No. 11 in WO 03/086517), whereby the disclosed device uses aspects of the instant invention to open a receptacle containing a powder and having a foil lid, e.g., by tearing the foil. Still further, the cutter mechanism described herein (or portions thereof such as the tooth or teeth) can be used in an inhaler described in US 2005/0279356, and more specifically can be used in place of the foil cutter disclosed in US 2005/0279356, whereby the disclosed device uses aspects of the instant invention to open a receptacle containing a powder and having a foil lid, e.g., by tearing the foil. Even further, the cutter mechanism described herein (or portions thereof such as the tooth or teeth) can be used in an inhaler described in US 2007/0068524, and more specifically can be used in place of the foil cutter disclosed in US 2007/0068524, whereby the disclosed device uses aspects of the instant invention to open a receptacle containing a powder and having a foil lid, e.g., by tearing the foil. Additionally, the cutter mechanism described herein (or portions thereof such as the tooth or teeth) can be used in an inhaler of the type described in any of the following documents: U.S. Pat. No. 6,360,744; U.S. Pat. No. 6,422,236; U.S. Pat. No. 6,436,227; U.S. Pat. No. 6,526,969; U.S. Pat. No. 6,881,398; U.S. Pat. No. 6,868,853; U.S. Pat. No. 6,840,239; U.S. Pat. No. 6,622,723; and U.S. Pat. No. 6,651,341, the disclosures of these documents are hereby expressly incorporated by reference in their entireties.

In view of the above, the blade of the present invention may be used in a device for de-aggregating and into air dispersing particles of a finely divided dry medication powder loaded onto a substrate member. The powder may be made available for inhalation by means of a dry powder inhaler comprising a nozzle with a nozzle outlet, a nozzle inlet, and a nozzle inlet aperture positioned adjacent to available powder. Suction of air, when applied to the nozzle outlet, creates a local, high velocity air stream into the nozzle inlet aperture and out through the nozzle outlet. A relative motion, when introduced between the nozzle and powder onto the substrate member, is arranged such that the nozzle inlet, and the local, high velocity air stream going into the nozzle inlet aperture, traverses the available medication powder, wherein the powder is released and dispersed. Particle aggregates within the finely divided medication powder are de-aggregated by being subjected to shearing stresses, inertia, and turbulence in the local, high velocity air stream going into the nozzle inlet aperture, whereby the particles of the finely divided medication powder are gradually dispersed into the air as available powder is gradually accessed by the local, high velocity air stream when the nozzle and the powder are moved in relation to each other.

The present invention is not limited to the above cutter mechanism. Other cutter mechanisms may be used with other features of the present invention, e.g., deoccluding device, trigger, orifice, etc. As opposed to the punch, plow, and remove before inhalation of the above cutter mechanism, other useful cutter mechanism operations include: (1) punch and retract; (2) punch and stay in position during inhalation; and (3) punch, rotate, and stay in position during inhalation. Also, rather than being made of plastic, the cutter mechanism may be made of wire stock, or by metal injection molding, sheet metal stamping, or sheet metal stamping and grinding.

Deoccluding Device

Another aspect of the invention relates to a deoccluding device, which may be used in any application in which a deoccluding a tube is desired. For example, in one embodiment the deoccluding device is arranged within and/or is configured to clean a feed tube. By way of non-limiting example, the feed tube can be a tube member which directs air flow from the exit opening of a receptacle toward an exit or mouthpiece opening of an inhalation apparatus. According to one non-limiting embodiment of the invention, such a device can particularly be utilized in the apparatus and/or method for aerosolizing a powdered medicament as described herein. The receptacle can take the form of a primary drug package, which can be sealed against moisture using a foil that spans a tub containing the powder (e.g., of the type shown in FIGS. 108-111). To release the powder for inhalation by a user in an effective manner, this foil is preferably punctured with an opening in a substantially controlled fashion. This control can be performed effectively using the puncturing and deoccluding device arranged within the feed tube.

In dry powder inhalers, there is a tendency for the flow paths (and especially any restrictions therein) to become clogged with powder, particularly in humid conditions. Such a restriction exists at the point where the drug exits the primary drug package, i.e., the receptacle, and is introduced into the apparatus. Clogging at this interface can have deleterious effects on the aerosol performance of the apparatus. The deoccluding device can thus be configured to actively deocclude the feed tube upon each actuation of the apparatus to ensure the drug path, i.e., the path for the aerosolized powdered medicament, remains unclogged. In some embodiments, the deoccluding device deoccludes by contacting the feed tube. In other embodiments, the deoccluding device deoccludes by riding just over the surface of the feed tube, such as at a sufficient distance to prevent or limit clogging while avoiding contact with the surface or minimizing contact with the surface, e.g., at a distance within 0.2 mm, such as within 0.15 mm or within 0.1 mm. By avoiding contact, less friction results, and the device typically operates more smoothly. The deoccluding device can also create an exit hole or opening in the receptacle (see e.g., the center exit opening in FIG. 102), thereby eliminating potential misalignments of the exit hole in the receptacle, e.g., blister pack, with the drug exit tube in the apparatus.

According to one non-limiting embodiment of the invention, the deoccluding device provides active deocclusion of the drug path upon each actuation of the apparatus (e.g., each time the apparatus is actuated as shown in FIG. 5). By keeping the drug path consistently unclogged, this device increases the useful life of the apparatus. For example, depending on the type of powder, the useful life may range from 50 to 400 uses, such as 70 to 200 uses, 80 to 150 uses, or 90 to 110 uses. Depending on the frequency of use, this results in a use life of at least 1 month, such as at least 2 months, at least 6 months, or at least 1 year. This results in greater convenience for the user, e.g., patient, and reduces the yearly cost of therapy. Furthermore, because the drug path (and in particular the most restricted portion thereof or the portion of the path most likely to become clogged) is deoccludeed upon each actuation, the pressure drop through the apparatus (and thus the overall performance thereof) varies little, i.e., is substantially constant, over the life of the apparatus. For example, over the life of the apparatus, e.g., over 200 uses, the pressure drop usually varies less than 2%, such as less than 1% or less than 0.5%. By way of non-limiting example, FIG. 112 shows air/powder flow up through a feed tube from the receptacle after the deoccluding device has cleaned the inside of the feed tube and assumed a retracted position.

Thus, the invention provides significant advantages over conventional inhalation devices. For example, certain inhalation devices are susceptible to clogging and gradually decline in performance over time.

The deoccluding device can also provide the additional function of opening the exit hole (see, e.g., center opening in FIG. 102) in the primary drug package, thereby ensuring its concentricity with the drug exit tube. In this case, the device can therefore be characterized as a puncturing and deoccluding device. Since concentricity of the hole relative to the tube increases the efficiency of the coupling between the drug package and the apparatus, the deoccluding device functions to maintain this concentricity. The deoccluding device may be a wireform, e.g., metal wireform, such as a stainless steel wireform. By utilizing a single simple wireform, e.g., a bent wire (see e.g., FIGS. 51 and 52), the device can provide multiple functions while also ensuring that the total part count of the apparatus is minimized. This results in a corresponding reduction in the cost of the apparatus. Of course, the deoccluding device could also be a molded member, such molded plastic, and can even be formed as a one-piece member with one of the components of the apparatus (or features of the components) such as, e.g., the feed tube or either a cutter mechanism (e.g., of the type shown in FIGS. 53-59 and 124-125) or a lower bearing member (e.g., of the type shown in FIGS. 66-72).

The deoccluding device is simple in design and can have the form of a single generally U-shaped or generally V-shaped (or a combination thereof) wireform part. By way of non-limiting example, the puncturing and deoccluding device can have the configuration shown in FIGS. 51-52. The device can also be configured to rotate at least partially upon actuation of the apparatus. This at least partial rotation of the apparatus (or parts thereof) can serve to drive the device (or cause its movement) without requiring a user to perform any other steps. The device can thus be driven internally and is therefore not dependent on the speed or technique of actuation by the user. The mechanism itself can be as simple as a thin wire, so it does not provide any significant impediment to the flow through the apparatus. The device is not limited to a wire (or round wire) and can have a number of cross-sectional shapes such as round, oval, square, polygonal, etc., provided the device is capable of providing one or more of the advantages noted herein. In some embodiments, the device is at least configured to be able to provide active deocclusion of at least a portion of the drug path upon each actuation of the apparatus.

As explained above, the receptacle can be, by way of non-limiting example, a drug package that utilizes a foil-plastic laminate lid and a tub that is roughly hemispherical in shape. Again, FIGS. 108-111 show non-limiting examples of such receptacles. The top of the drug package can be planar, and the tub is sealed with a foil lidstock over its entire top surface. Such a drug package can be inserted into an apparatus (see e.g., FIG. 4) containing the deoccluding device and the apparatus can be manipulated to automatically cause an opening of the drug package when, e.g., a rotary motion is applied to two portions of the apparatus (see e.g., FIG. 5).

As discussed above, the actuation of the apparatus allows the teeth to create several holes in the foil lidstock thereby forming air inlet openings allowing ambient air to enter the drug package. Furthermore, the deoccluding device can form the exit opening in the lidstock which then allows the air entrained with drug to exit the drug package. The exit opening is typically arranged directly below the feed tube which directs the entrained flow into the apparatus. Thus, the same device that forms the exit hole can also serve to deocclude the inner surface of the feed tube and vice versa. By way of non-limiting example, FIG. 102 shows a lidstock having two arc-shaped inlet openings and a center exit opening formed by a puncturing and deoccluding device of the type described herein.

By way of non-limiting example, the deoccluding device can have the form of a wire loop that is configured to rotate, e.g., about 180°, with each actuation of the apparatus. FIG. 5 shows one non-limiting way in which the actuation movement can occur. The deoccluding device can also be configured to descend (e.g., move linearly and/or axially within the feed tube toward the lidstock) and retract (e.g., move axially away from the lidstock) by, e.g., about 2 mm, either during or after it initially experiences rotary motion. The vertical sides of the wire loop are configured to deocclude an inside of the feed tube while the bent end, e.g., curved end, perforates the center of the receptacle, e.g., blister pack or drug package. As the loop rotates, the initial penetration of the receptacle, e.g., drug package or blister pack, becomes generally circular. In this regard, the circular hole may be formed by an initial piercing followed by plowing. According to one non-limiting embodiment, the feed tube does not move relative to the blister pack, so that it can serve as a guide for the movement of the wire loop. This ensures concentricity (i.e., axial alignment) of the hole in the lidstock relative to the feed tube. According to the invention, the controlled relative motion of the wire loop and the blister/feed tube is able to provide both the deocclusion and blister opening functions. By way of non-limiting example, the deoccluding device can be used to clean the inside of the feed tube of the lower bearing member shown in FIGS. 66-72 and having upper and lower ends 100*n* and 100*s*, respectively.

The wire diameter can be sized to properly form the hole or opening in the receptacle and also perform the deocclusion function efficiently without significantly obstructing air flow through the device when retracted. For example, the wire should not be made too small in diameter so as not to propagate an uncontrolled tear in the lidstock and should not be made too large so as to obstruct the airflow through the feed tube. For instance, the wire may have a diameter ranging from 0.020 inch to 0.054 inch, such as 0.022 inch to 0.044 inch or 0.024 inch to 0.034 inch. The diameter of the wire affects the radius of the bend possible. Typically, the ratio of the radius of the bend to the radius of the wire is 1.5 or less. FIG. 112 shows flow through the feed tube with the deoccluding member in a retracted position.

Impacting or Receptacle Impacting Device

Another aspect of the invention relates to an impacting device. The impacting device of the present invention can be used in most any application in which an impact is desired. For example, the impacting device may be used to impact receptacles inline during a filling process to break up powders. According to one non-limiting embodiment of the invention, such a device can particularly be utilized in the apparatus and/or method for aerosolizing a powdered medicament as described herein. Non-limiting examples of such inhalation devices are shown in FIGS. 1-9, 24-27, and 128-138. The receptacle can take the form of a primary drug package, which is sealed against moisture using a foil that spans the tub containing the powder (e.g., of the type shown in FIGS. 108-111). The impacting device has particular application in causing the powder arranged within the receptacle to be broken up into a more dispersible powder. It has been found that the powder in the blister pack receptacle is more easily deagglomerated if the blister pack is given a sharp impact before the blister pack is opened. Based on studies with an offline impact mechanism, the energy of impact typically ranges from 0.017 to 0.025 J, such as 0.007 to 0.085 J, or anything above about 0.005 J. The device described herein is structured and arranged to provide such an impact to the blister pack. When such an impacting device is utilized on the apparatus described herein, the impact can occur upon insertion of the receptacle into the apparatus.

In one embodiment, when used on an inhalation apparatus, such as on the apparatus described herein, the impacting device can be compact and can be made with only two additional components to the apparatus part count, that is, a torsion spring and an impacting member. However, the invention also contemplates using a single member which includes or performs the functions of these devices. The level of impact on the blister pack can be tailored to provide the maximum effect. For example, the impact should not be too light; otherwise it may not have the desired effect. It should also not be too heavy because it can cause the powder to compact on, among other places, an opposite surface of the blister pack from the location of impact.

The impacting device can be made of injection molded plastics compatible with high volume manufacturing. The device can also made so as to be easily assembled in an apparatus, e.g., it can be assembled in the vertical axis, i.e., uniaxial assembly, (which is compatible with high volume automated assembly) and can be made so as to not require special adjustment. The device can also desirably be configured so as to not require resetting by the user. According to one non-limiting embodiment, the impacting device is configured so that it can begin and end its movement in an apparent identical state. Because it can be configured to automatically reset so as not to require resetting by the user, the device will be less likely to accidentally end up in the wrong state (i.e., not reset).

Figure 94:
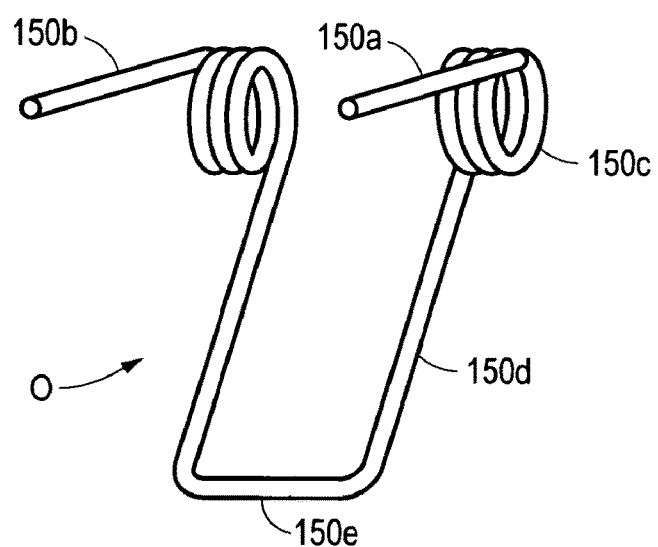
FIG. 94 shows a top right front perspective view of the torsion spring shown in FIG. 155.
Figure 95:
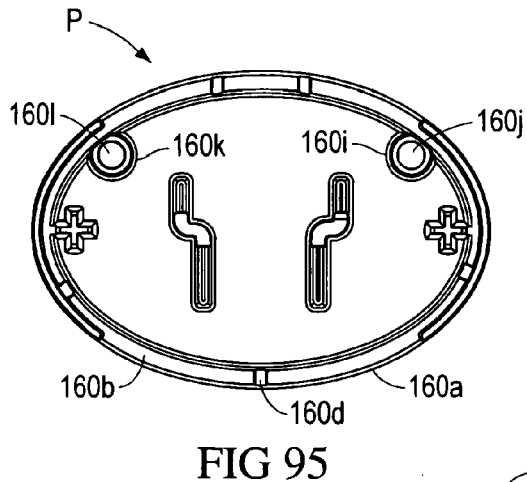
FIG. 95 shows a top view of the bottom or lower housing member shown in FIG. 9.
Figure 96:
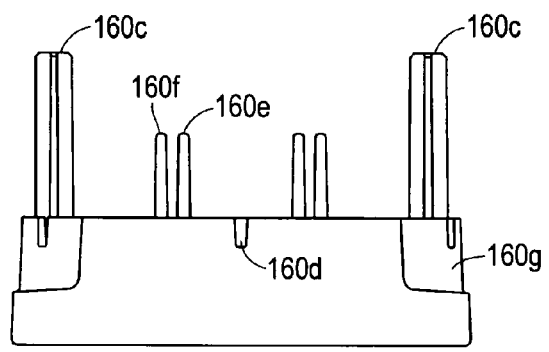
FIG. 96 shows a front side view of the bottom or lower housing member shown in FIG. 95.
Figure 97:
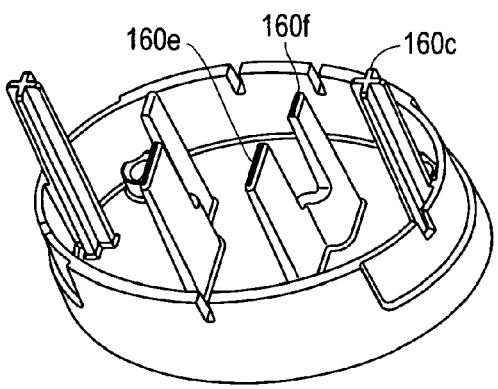
FIG. 97 shows a top right front perspective view of the bottom or lower housing member shown in FIG. 95.
Figure 98:
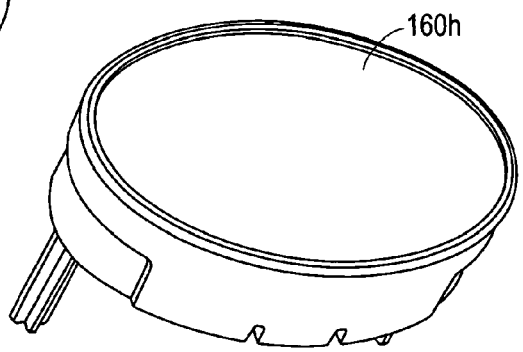
FIG. 98 shows a left bottom rear side perspective view of the bottom or lower housing member shown in FIG. 95.

The impacting device is preferably made so as to be simple and easy to assemble. As explained above, it can be configured to provide an impact to the receptacle upon its insertion into an apparatus. This action can simultaneously provide feedback (i.e., the user can come to recognize the sound of a fully and properly inserted receptacle based on the noise generated by the impacting device) to the user of correct blister insertion. The act of inserting the blister pack can also be utilized to provide the motive force for the activating the device. For example, a spring biasing the device can be lightly stressed when the device is not in use. A non-limiting example of such a spring is shown in FIG. 94. The impacting device can be made entirely from one or more injection molded plastics. The travel of the blister pack into the apparatus (see, e.g., FIGS. 4 and 104-107) can then be used to allow mechanical advantage to drive the device and compress the spring. This configuration can eliminate the need for additional devices such as metal springs, which provides a cost savings in materials and assembly costs—especially in high volume production. The requirements for the spring are compatible with a molded plastic beam incorporated into another part in the assembly, thus the total increase in part count can be a single component. In other embodiments, a metal spring is used. The lack of a need for resetting the device can also reduce the potential failure modes in the operation of the apparatus.

Figure 19:
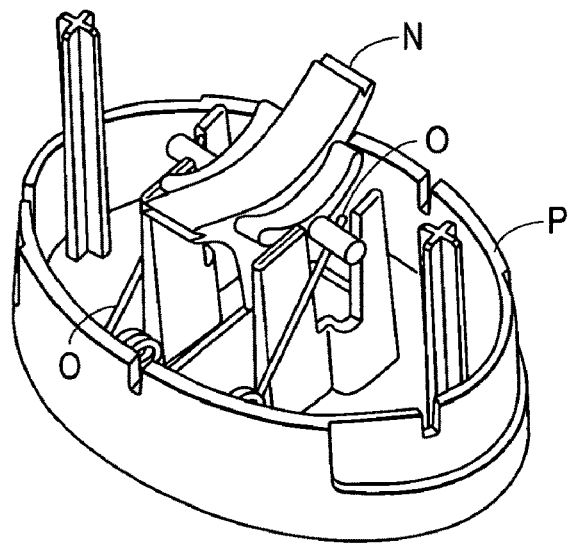
FIG. 19 shows how the receptacle impacting mechanism and the subassembly shown in FIG. 18 are assembled together.

By way of non-limiting example, the impacting device can be a tri-lobed wheel with a central axle protruding out on one or more sides. Non-limiting examples of such a tri-lobed wheel are shown in FIGS. 88-92. When installed in an apparatus, the wheel can be constrained axially by ribs (e.g., ribs 160*e* in FIGS. 95-98) that protrude from a bottom surface of the apparatus or a portion thereof. Slots in these ribs can constrain or limit the overall movement of the axle of the wheel and also allow it to ride up and down vertically. In this arrangement, the wheel can be free to rotate and also move up and down in the slots. It can also be prevented from moving substantially axially or side-to-side. A spring is positioned so as to bias each side of the axle so as to cause a biasing of the tri-lobed wheel upwards. FIG. 19 shows one non-limiting way in which the wheel can be mounted to the slots of the ribs and biased upwards by a spring. Two lobes of the wheel can also be configured to rest against a horizontal surface that is in the same plane as the top of the blister pack insertion slot in the apparatus. Viewed from the side, the wheel can appear to generally form a "Y" shape (see, e.g., FIG. 104). As the blister pack is inserted into the apparatus, a leading edge of blister pack can contact one of the lobes of the wheel and cause the wheel to rotate (see, e.g., FIGS. 105-107).

Figure 115:
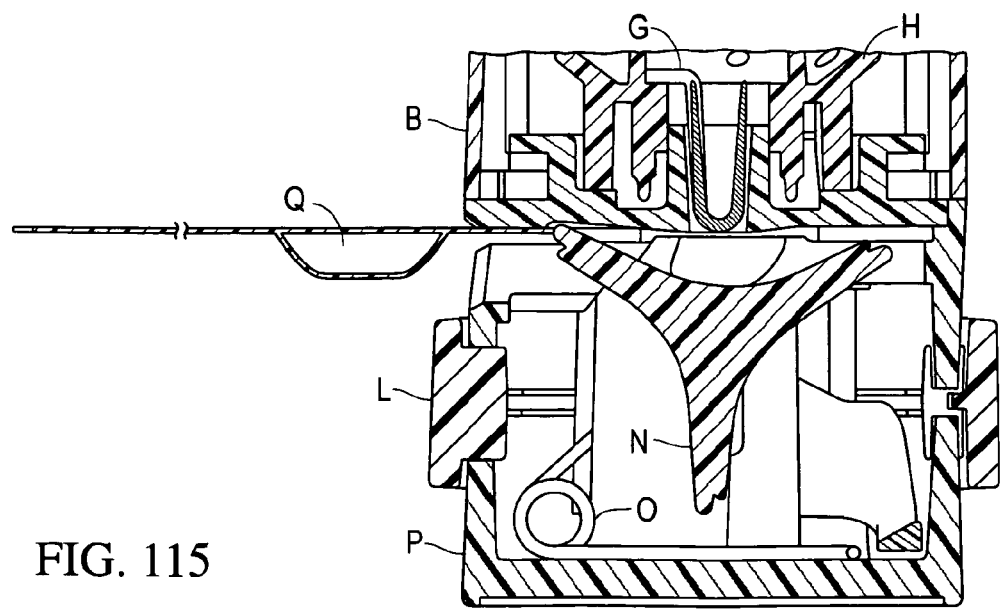
Figure 116:
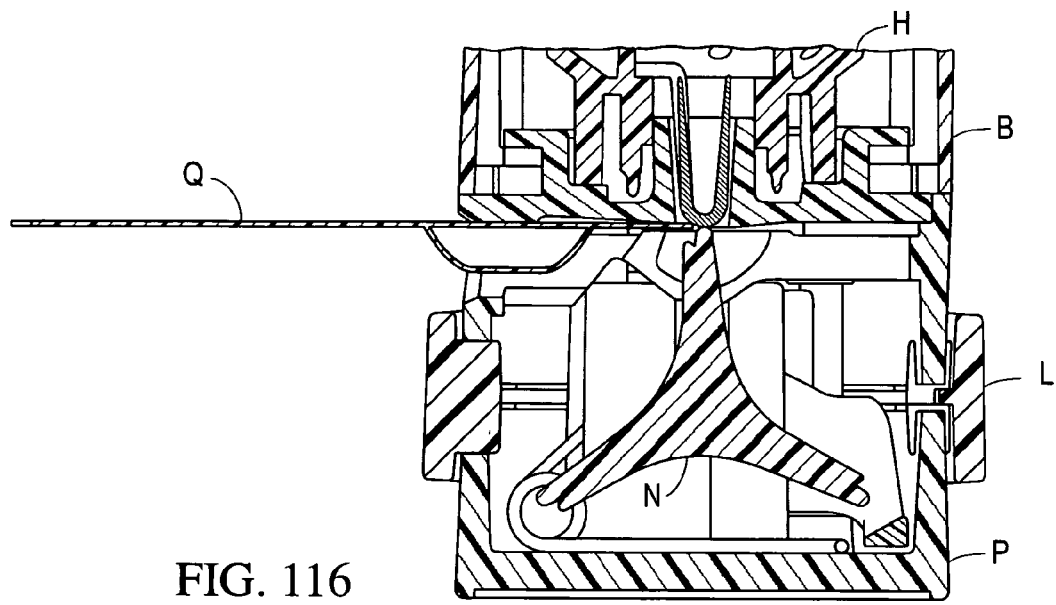
Figure 117:
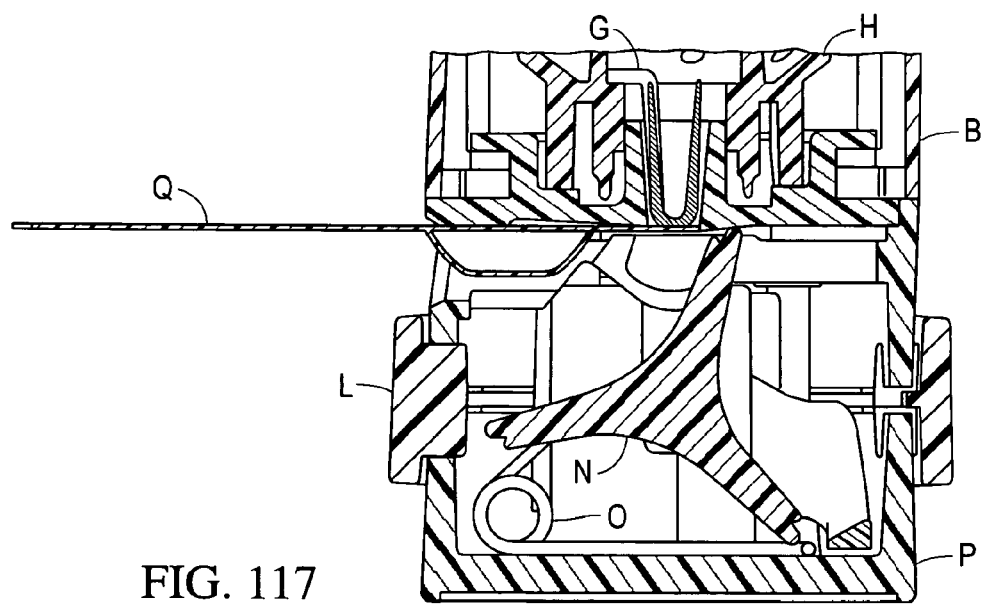
Figure 118:
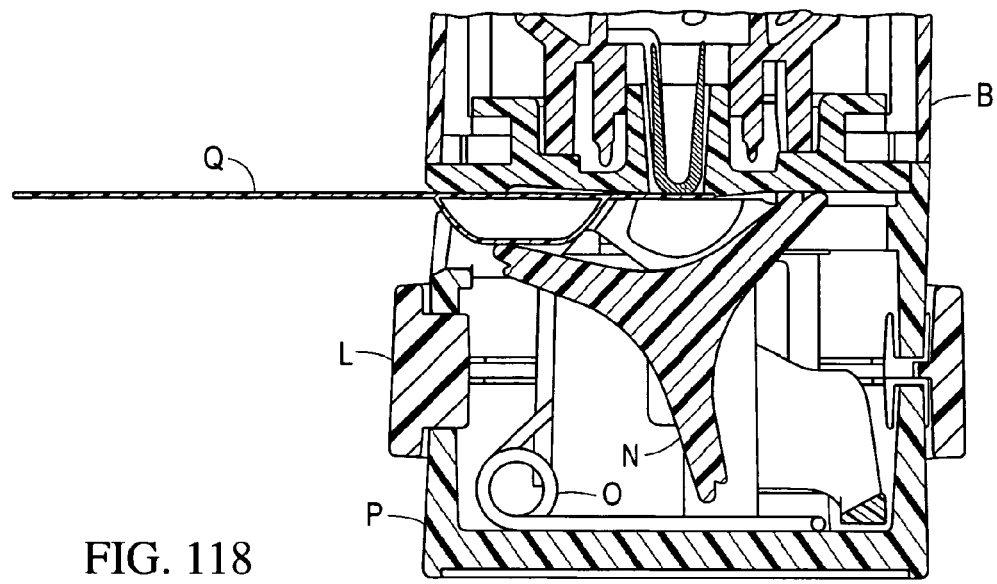
Figure 119:
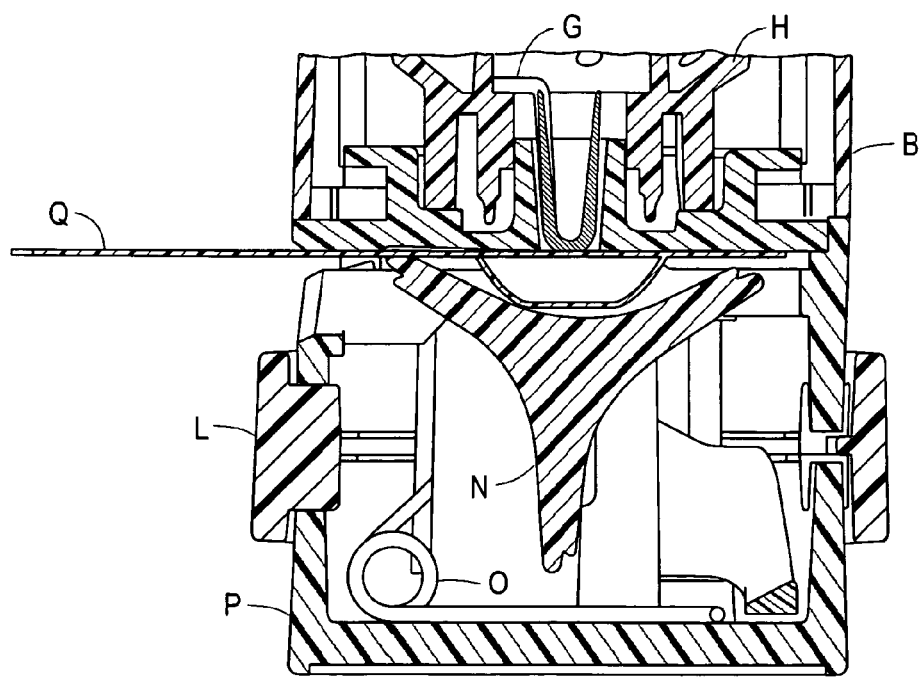
Figure 120:
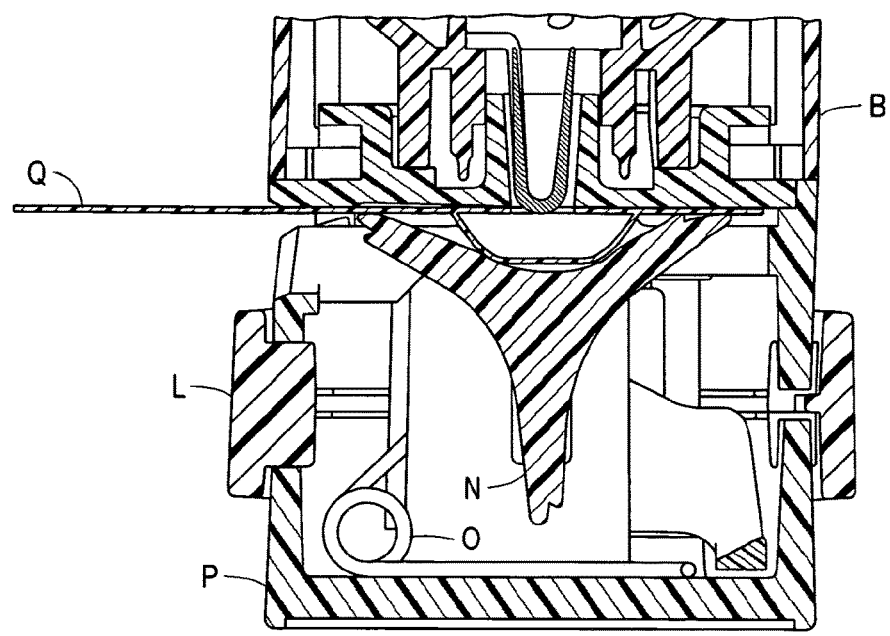
Figure 121:
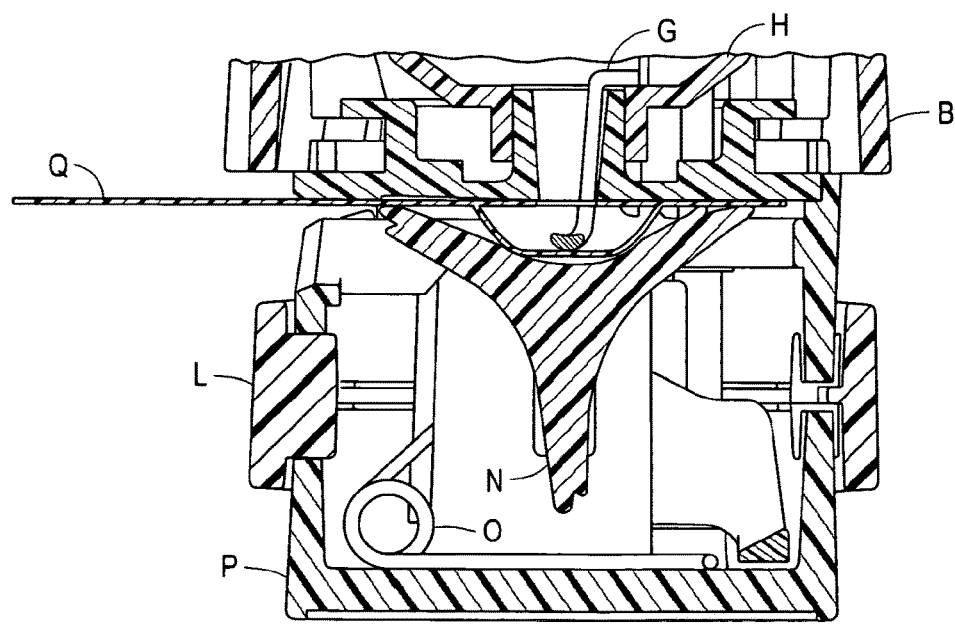
Figure 122:
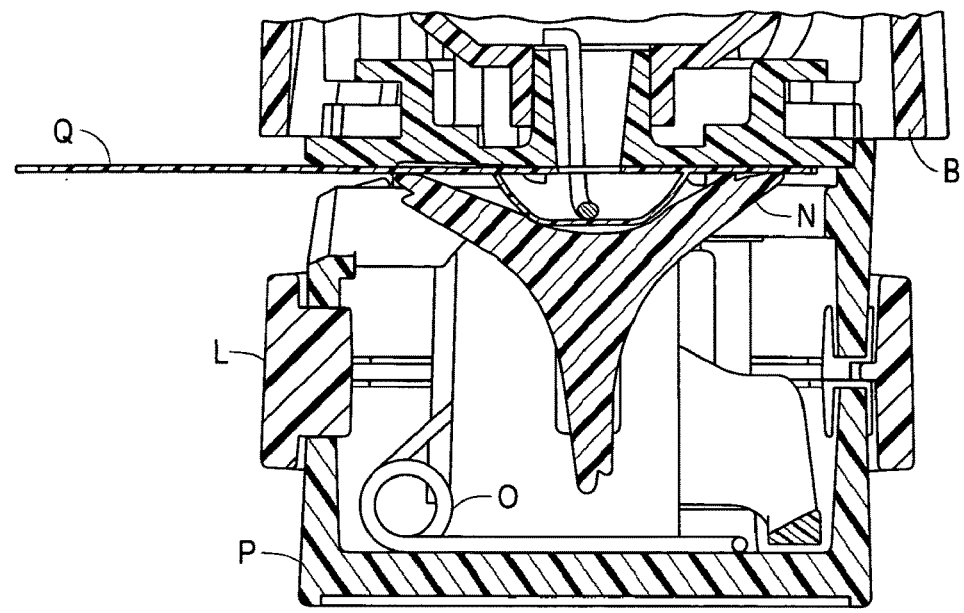
Figure 123:
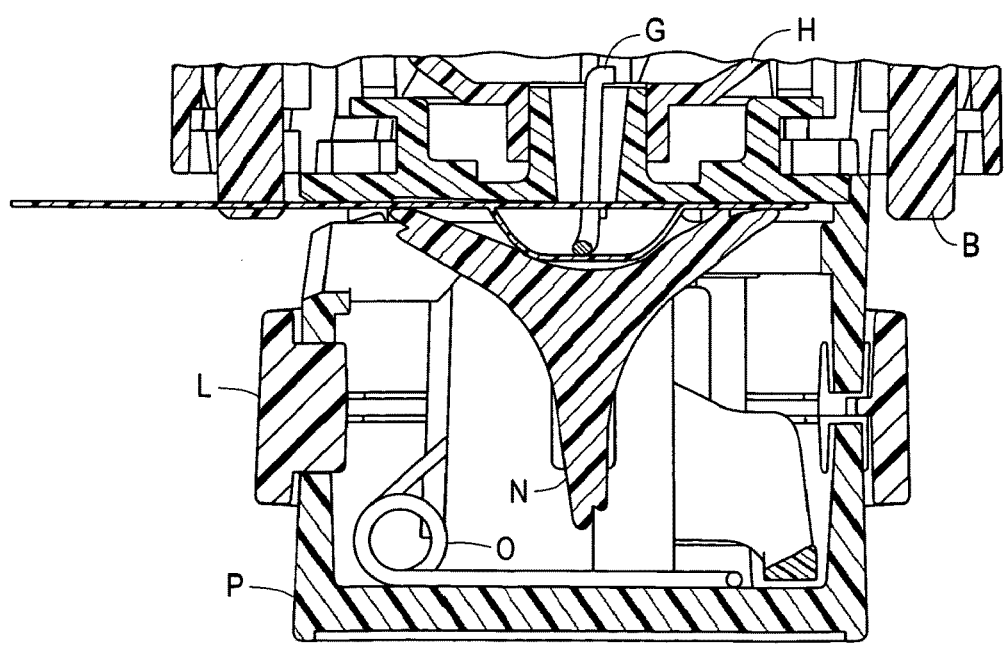
Figure 124:
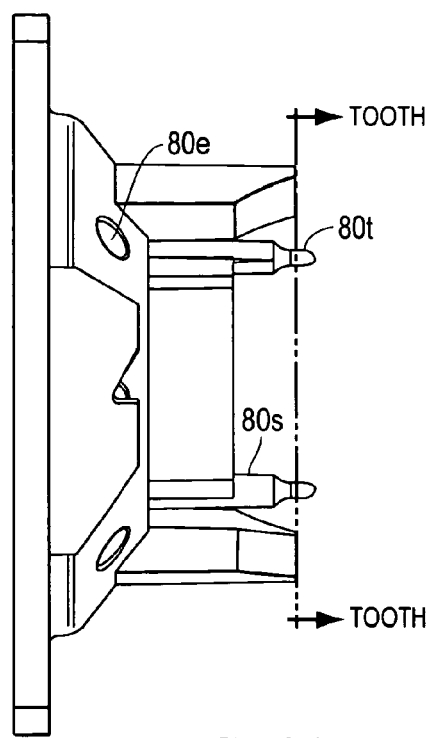
FIG. 124 shows an enlarged left side view of an exemplary cutter mechanism which can be used in the inhalation apparatus.
Figure 125:
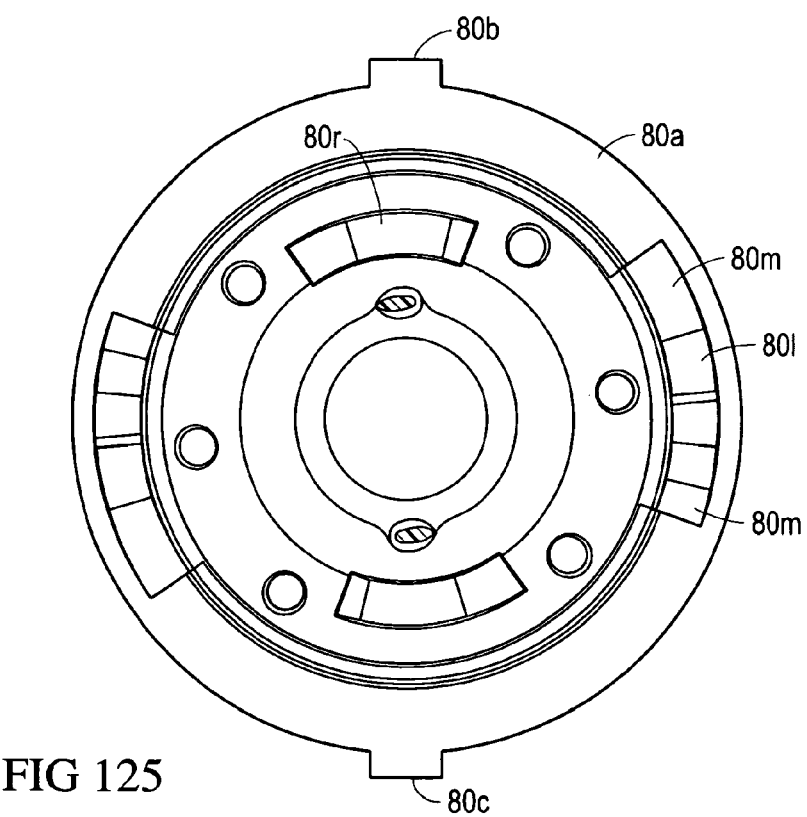
FIG. 125 shows a top view of the cutter mechanism shown in FIG. 124.

According to one non-limiting embodiment, each lobe of the wheel can have a notch at the end which catches the leading edge of the blister pack as it is inserted into the apparatus (see, e.g., FIG. 115). According to another non-limiting embodiment, each lobe of the wheel can be configured to contact the curved front portion of the tub of the receptacle as it is inserted into the apparatus (see, e.g., FIG. 104). Regardless, further sliding into the apparatus of the blister pack causes the wheel to rotate (see FIGS. 105-107 and 116-119). As the wheel rotates, the end of the contacted lobe moves with the blister pack or receptacle and along the horizontal surface above the blister insertion slot. All the while, the wheel is biased upwards by the spring (e.g., a spring of the type shown in FIG. 94). As a result, the wheel is caused to move downward or away from the horizontal surface. This movement is guided because the axle is movably disposed in the retention slots. As the axle moves downward, the spring becomes compressed. The maximum compression of the spring occurs when the tri-lobed wheel resembles a generally upside-down "Y" as viewed from the side (see e.g., FIGS. 106 and 116). By way of non-limiting example, this position can correspond to approximately 50%, such as 40% to 60%, blister insertion, i.e., the wheel will resemble the upside-down "Y" when the blister pack is inserted into the apparatus half-way. Further insertion movement of the receptacle causes the impacting device to rapidly go over-center (see e.g., FIGS. 117 and 118). That is, the lobe that has moved to an approximately vertical position when the blister pack is half-way inserted, will automatically rapidly move or rotate along the direction of insertion when it rotates past the vertical position owing to the biasing action of the spring. This results in a sudden release of the spring energy, which in turn causes an adjacent lobe of the wheel to rapidly impact the bottom of the blister tub (see e.g., FIG. 118). The level of energy imparted to the blister tub is largely dependent upon the spring force. Thus, the energy can be tuned by design to provide the desired effect. For example, in one embodiment, when the device is at rest, or during inhalation, the spring is compressed to 11.35 mm. When the device is cutting or tearing, the spring is compressed to 13.85 mm. The free length of the spring is nominally 19.05 mm and the spring rate is 1.89 N/mm. This means that the nominal spring force is 14.5 N when at rest, and 9.8 N during cutting or tearing. The spring force at rest typically ranges from 10 N to 16 N, such as 11 N to 15 N, or 12 N to 14 N. The spring force during cutting or tearing typically ranges from 7 N to 11 N, such as from 8 N to 10 N.

The impacting device is also preferably configured so as not to interfere with the removal of the receptacle from the apparatus (see e.g., FIG. 7). By utilizing a tri-lobed wheel, removal of the blister pack can occur easily. This is because the tri-lobed wheel does not need to rotate in an opposite direction very much to allow the tub to slide past. Furthermore, by making the three lobes on the wheel substantially identical, the device can end up in a position which resembles the initial starting position, even though the wheel has turned 120° each time a receptacle is inserted. In this configuration, the impacting device ensures that no resetting of the apparatus by the user is needed, and the impacting device remains always ready for the insertion of another or new receptacle.

Other non-limiting examples of impact mechanisms include bistable springform, spring loaded mousetrap type mechanism, and embossed ridges on the blister to induce vibration.

Lock System or Receptacle Lock System

Another aspect of the invention relates to a lock device or system. This system may be used in most any application in which a locking is desired. For example, the lock system may be a receptacle lock system in which an inhaler device is locked during insertion of a receptacle. One advantage of this device is that it prevents possible damage to the teeth of the receptacle puncturing mechanism which could otherwise occur if the teeth descend into portions of the receptacle which are more rigid and/or thicker instead of into the foil lid stock of the receptacle (which they are configured to penetrate and tear). Additionally, such device can be configured to allow only one predetermined shape of receptacle, e.g., blister pack. This feature minimizes the chance that improper medication is inserted into the device. According to one non-limiting embodiment of the invention, such a device can particularly be utilized in the apparatus and/or method for aerosolizing a powdered medicament as described herein. Non-limiting examples of such inhalation devices are shown in FIGS. 1-9, 24-27, 114-123 and 128-138. The receptacle can preferably take the form of a primary drug package which is sealed against moisture using a foil that spans the tub containing the powder (e.g., of the type shown in FIGS. 108-111). The device has particular application when used in the apparatus and/or method for aerosolizing a powdered medicament which utilizes single-use receptacles, e.g., blister packs.

The receptacle lock system can be configured to prevent relative rotation between two portions of an apparatus unless a receptacle of predetermined configuration is properly inserted into the apparatus. This feature increases the likelihood that the patient will be successfully dosed. The receptacle lock system can also preferably allow relative rotation between two portions of an apparatus when a receptacle is not inserted into the apparatus. This can allow the user to become familiar with the operation of the apparatus without wasting a receptacle. It is also contemplated that the receptacle lock system may prevent relative rotation between two portions of an apparatus unless a receptacle of predetermined configuration is properly and/or fully inserted into the apparatus.

According to one non-limiting embodiment, the lock device can function as follows: while the blister pack is inserted into the apparatus (see, e.g., FIG. 4), spring-loaded arms with interlock pins of the receptacle lock device can spread apart by angled edges of the blister pack. While these arms are spread apart and before they are moved to an original position, the lock device can prevent use and/or activation of the apparatus, i.e., it can prevent the type of movement shown in FIG. 5. By way of non-limiting example, the lock device can prevent relative rotation of the parts of the apparatus such as the rotation of a mouthpiece relative to another housing part. When the blister pack has reached a home or fully inserted position, the interlock pins engage with one or more recesses, e.g., cutouts 170g of FIGS. 108-111, on the sides of the receptacle. At this point, the arms move to an unlocked position, which will allow the user to activate or use the apparatus, e.g., the mouthpiece is then allowed to rotate relative to the lower half of the apparatus (see e.g., FIG. 5). By way of non-limiting example, the lock device can have the configuration shown in FIGS. 84-87.

Receptacles

In view of the above, another aspect of the invention relates to the receptacles themselves. In one version, the receptacle includes a lower foil laminate comprising a blister for holding powder and an upper foil laminate covering the lower foil laminate. The receptacle comprises a rear portion having three perpendicular sides, a middle portion comprising notches, and a tapered front portion. The notches are capable of interacting with the above-described receptacle interlock system.

Non-limiting examples of receptacle materials include those disclosed in U.S. Pat. Nos. 5,589,275 and 6,270,869, which are incorporated herein by reference. Suitable foils are commercially available, e.g., from Alcan Inc. (Montreal, Quebec).

The invention also contemplates an arrangement wherein the receptacle is supported in a mechanism for advancing a continuous web (e.g., a strip or disk), which carries a plurality of receptacles past the fluidization location. Non-limiting examples of such devices are disclosed in U.S. Pat. No. 6,606,992, the disclosure of which is hereby expressly incorporated by reference in its entirety.

Trigger Valve

Still another aspect of the invention relates to triggers or trigger valves. The trigger may be positioned between the receptacle and the outlet of the mouthpiece such that air flow from the receptacle to the outlet passes through the valve. A non-limiting example of the trigger is shown in FIGS. 44-47.

One function of the trigger is to ensure consistent and uniform dosing. To open the trigger, a threshold vacuum pressure must be applied. For instance, the threshold vacuum pressure is usually at least about 15 cm $H_2O$ or at least 25 cm $H_2O$, and typically ranges from 10 cm $H_2O$ to 50 cm $H_2O$, such as from 15 cm $H_2O$ to 40 cm $H_2O$, 18 cm $H_2O$ to 30 cm $H_2O$, or 24 to 30 cm $H_2O$. Accordingly, the initial flow rate through the device is consistent with respect to intrapatient and interpatient variability. Thus, the trigger functions to regulate air flow through the device. The trigger also provides audible and tactile feedback to the user indicating correct inhalation.

Another function of the trigger is to deagglomerate the powder. Deagglomeration of the powder increases the fine particle fraction and increases the amount deposited in the lungs.

Still another function of the trigger is to reduce patient blowback. Reducing patient blowback increases the cleanliness of the device.

The trigger is typically automatically closing or self-closing, which eliminates the need for resetting the trigger. When the vacuum is removed, i.e., when the patient stops inhaling, the trigger is biased back into its original position. The valve will usually reset at valve pressure drop below 5 cm $H_2O$, such as less than 4 cm $H_2O$ or less than 3 cm $H_2O$.

Typically, the trigger is also self-deoccluding. The opening and closing of the trigger prevents powder from accumulating thereon. The Shore A hardness of the trigger usually ranges from 20 to 60, such as 30 to 50 or 35 to 45.

Non-limiting examples of valves include those disclosed in U.S. Pat. Nos. 5,213,236; 5,377,877; 5,409,144; 5,531,363; 5,839,614; 6,065,642; 6,079,594; 6,273,296; 6,405,901; 6,951,295; and 7,086,572; and U.S. Published Application No. 2004/0000309, which are incorporated herein by reference. Suitable valves are commercially available, e.g., from Liquid Molding Systems (Midland, Mich.), and many of these valves are described on their website at www.siliconelms.com, which is incorporated herein by reference.

Apparatus Utilizing One or More of the Above-Noted Features

Although the invention contemplates using one or more of the above-noted features, e.g., the cutter mechanism, the deoccluding device, the receptacle impacting device, the receptacle lock device or system, the receptacles, and the trigger, in or on devices such as apparatuses for aerosolizing a powdered medicament, such features can also be used alone, in various apparatuses, and in an apparatus of the type described herein. As an example, the cutter mechanism could be used for cutting different materials. Still further, a skilled artisan would appreciate that many of the methods and approaches of the present invention can find use with the dispersion and delivery of preselected metered amounts (boluses) of powdered medicaments from receptacles containing multiple dosage units, i.e., "bulk" powders contained in a single receptacle. For example, the trigger, impact mechanism, and deoccluding device of the present invention would work with a reservoir device.

The invention also relates to the pulmonary delivery of dry powder medicament such that an arrangement for efficient and repeatable powder fluidization and deagglomeration is combined with an arrangement for providing, through airflow control, enhanced consistency of lung deposition within an apparatus powered by the user's inhalation effort.

A passive DPI (dry powder inhaler) is a man-machine system including the powder to be delivered via pulmonary route, a delivery device (i.e., an apparatus of the type described herein), and the user. The user, who supplies power for the device through inhalation effort, tends to be the source of highest variability. It is therefore desirable to control the user's inhalation such that energy provided for powder aerosolization and flow rate of aerosolized powder to the lungs are both controlled within a narrow range. One aim of the delivery apparatus is to aerosolize the powder medicament consistently in both size of dose delivered and aerosol quality. Powder quality may be measured as fine particle fraction, or FPF, to indicate the fraction of the aerosolized powder having particle size below a given threshold. Typically, the primary particle size is substantially smaller than the threshold used for FPF. Therefore, FPF is most often a function of agglomeration state, or percentage distribution of particles that are single primary particles or agglomerations of multiple primary particles. It has been found that to provide superior aerosol quality, as measured by FPF or more precisely agglomerate state, it is highly effective to divide the aerosolization function into two distinct, successive stages. The first such stage of aerosolization is Powder Fluidization that is intended to produce a suspension of particles of powder medicament in an air stream. Often, FPF and agglomeration state of the powder medicament are not ideal after Powder Fluidization. Therefore, a second stage may be utilized and is designated here as Powder Deagglomeration. The Powder Deagglomeration stage can provide a way to break-up a high percentage of agglomerates into smaller agglomerates or possibly into primary particles. The Powder Deagglomeration may be accomplished through shearing airflows, turbulent airflows, impaction, or accelerating flows. It should be evident to one skilled in the art that the above sequence of aerosolization stages can provide a beneficial particle delivery by using Powder Fluidization followed by Powder Deagglomeration.

Efficacy of two-stage powder aerosolization depends in part on inhalation flow patterns. For instance, it has been found that high value of flow increase rate, or FIR, is desirable in accomplishing the Powder Fluidization phase. For instance, the peak FIR often exceeds 5 liters/sec$^2$, such as above 10 liters/sec$^2$. The peak FIR may, e.g., range from 10 liters/sec$^2$ to 50 liters/sec$^2$, such as 15 liters/sec$^2$ to 40 liters/sec$^2$ or 20 liters/sec$^2$ to 30 liters/sec$^2$.

It has also been found that, once airflow is initiated, controlled flow rate provides both more consistent powder deagglomeration and more consistent flow to control pulmonary deposition. For these reasons, the inhalation control function can be a single stage or can be divided into two stages. The first stage of inhalation control can provide a way for imposing a threshold pressure differential, such that the user must meet or exceed this threshold pressure differential through vacuum of inhalation effort before flow begins. The threshold vacuum may be accomplished with a trigger valve (e.g., of the type shown in FIGS. 44-47), i.e., a mechanism for enforcing threshold pressure differential such that essentially no airflow can occur until pressure drop across the trigger valve exceeds the threshold pressure differential. The optional second stage of inhalation control can provide a way for regulating flow rate once the threshold vacuum is achieved, wherein the regulating arrangement may be a flow regulator valve that changes orifice shape in order to control flow rate as a predetermined function of pressure drop across the flow regulator valve.

It has been found that separating powder aerosolization into sequential stages of Powder Fluidization and Powder Deagglomeration, where the Powder Deagglomeration is accomplished by structuring and arranging elements of the device to produce airflows having high acceleration, and where inhalation control is enforced to achieve a high value of FIR, produces aerosols of surprising and unexpectedly high FPD and agglomeration states having a high percentage of small agglomerates or possibly primary particles.

According to one non-limiting embodiment, there is provided an apparatus for aerosolizing a powdered medicament which is a passive dry powder inhaler. Non-limiting examples of such devices are shown in FIGS. 1-9, 24-27, and 128-138. As used herein, the term passive means that it requires patient inspiratory effort to generate an aerosol, in contrast to an active inhaler which utilizes a mechanism in the apparatus to create the aerosol. The drug product is packaged in a receptacle, e.g., foil blister pack, which is opened by the device and evacuated using the user's, e.g., a patient's, breath. FIGS. 108-111 show non-limiting example of such a receptacle, which happens to be a foil blister pack.

With reference to FIGS. 1-9, and by way of non-limiting example, the apparatus can utilize two main modules or component assemblies, i.e., a receptacle preparation module and an aerosolization module. The receptacle preparation module can utilize, among other things, one or more of a receptacle impact device of the type described above, a receptacle lock device of the type described above, a receptacle as described above, a trigger as described above, a blister centering arrangement, a deoccluding device of the type described above, and a receptacle puncturing mechanism of the type described above. Receptacle preparation may be achieved by inserting a receptacle or blister pack Q into the apparatus (e.g., as is shown in FIGS. 4, 104-107, and 115-119) and until a click is heard, indicating that the receptacle impact device N has actuated. While the blister pack Q is being inserted, the spring-loaded interlock pins of the receptacle lock device M are caused to spread apart, preventing the mouthpiece B of the apparatus from being rotated prematurely. When the blister pack Q has reached the fully inserted or home position (see e.g., FIGS. 107 and 119), the interlock pins 130*a* (see FIGS. 84-87) engage with cutouts 170*g* (see FIGS. 108-111) on the side of the blister pack Q. This allows the mouthpiece B to be rotated by a user (see, e.g., FIG. 5). The mouthpiece B can then be rotated relative to a lower portion of the apparatus. This causes movement of the puncturing portion 70*g* (see FIGS. 51-51) of the deoccluding device G and the puncturing teeth 80*t* (see FIGS. 53-59) of the receptacle puncturing mechanism H to descend into the tub of the blister pack Q, thereby creating a centrally disposed exit opening, as well as inlet openings, in the foil lid (see, e.g., FIG. 102).

The receptacle impact device N can be a three-lobed cam wheel (see FIGS. 88-92) that is spring-loaded via spring O (see FIG. 94). As the blister pack Q is pushed into the apparatus (see FIG. 4), this mechanism N stores energy via the spring O, which is then released to create a sudden impact on the blister tub. This acts to loosen the powder in the receptacle Q to thereby improve blister pack evacuation efficiency and reduce variability in emitted dose. The emitted dose of the present invention is typically at least 60%, such as at least 70%, at least 75%, at least 80%, at least 85%, or at least 90%. The standard deviation of the emitted dose is typically less than 10%, such as less than 7%, less than 5%, or less than 3%. For example, the emitted dose may range from 60% to 90% with an RSD of 3% to 10%.

The blister centering arrangement, which can utilize, among other things, curved support surface 110*h* of the body member K shown in FIGS. 73-78, can serve to align the center of the blister tub with the central feed tube in the apparatus. The puncturing portion 70*g* (see FIGS. 51-52) of the deoccluding device G plunges into the foil lid stock on the top of the blister pack Q to create an exit opening. The puncturing teeth 80*t* (see FIGS. 53-59) of the receptacle puncturing mechanism H are positioned such that they descend into the foil lid shortly after the puncturing portion 70*g* of the deoccluding device G. This occurs because the puncturing end 70*g* of the deoccluding device G is position below the teeth 80*t* of the receptacle puncturing mechanism H. The puncturing end 70*g* of the deoccluding device G thus contacts and punctures the lid of receptacle Q just before the teeth 80*t* of the receptacle puncturing mechanism H. As the mouthpiece B is rotated (see FIG. 5), the puncturing portion 70*g* of the deoccluding device G displaces foil to create a center outlet hole while the teeth 80*t* of the receptacle puncturing mechanism H form two approximately 120° arc-shaped inlet openings. FIG. 102 shows the top of a receptacle with two inlet openings and a central exit opening formed in this way. The inlet openings form an inlet for air through the blister pack Q and the outlet opening allows air and powder to exit from the receptacle Q. FIG. 112 illustrates one non-limiting way in which this flow can take place. As was described above, the teeth 80*t* preferably do not actually cut the openings in the foil lid, and instead preferably cause or propagate a controlled tear(s). Preferably, the teeth 80*t* do not have sharp side leading edges and instead have rounded (or more blunted) leading edges to facilitate controlled and consistent propagation of the inlet openings. FIGS. 126-127 illustrate one non-limiting rounded configuration for the leading edge of the teeth 80*t*.

When the mouthpiece B has been rotated approximately 180° and clicks into place, the apparatus is ready for aerosolization of the powder in the blister pack. To aerosolize the powder, the user places the mouthpiece B, and more specifically the upper portion thereof, between his or her lips and creates a seal. By way of non-limiting example, the mouthpiece B shape can preferably be designed to be optimal for a wide range of mouth sizes and user preferences. As the user creates a vacuum (indicated by arrow in

Figure 25:
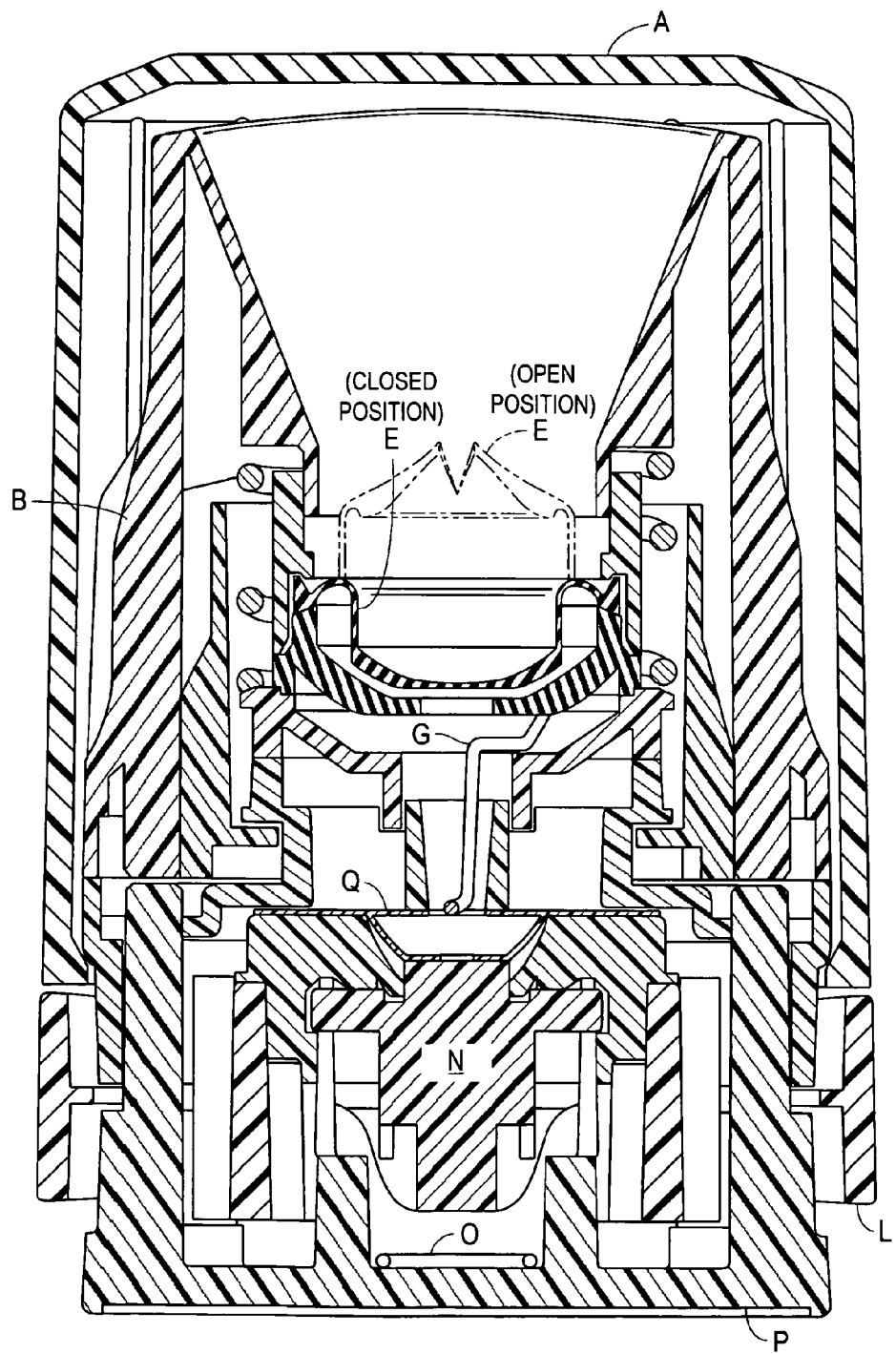
FIG. 25 shows a cut-away rear-side view of the embodiment shown in FIG. 24 with a receptacle installed therein. For purposes of illustration, the trigger is shown in both the closed position and the open position.
Figure 26:
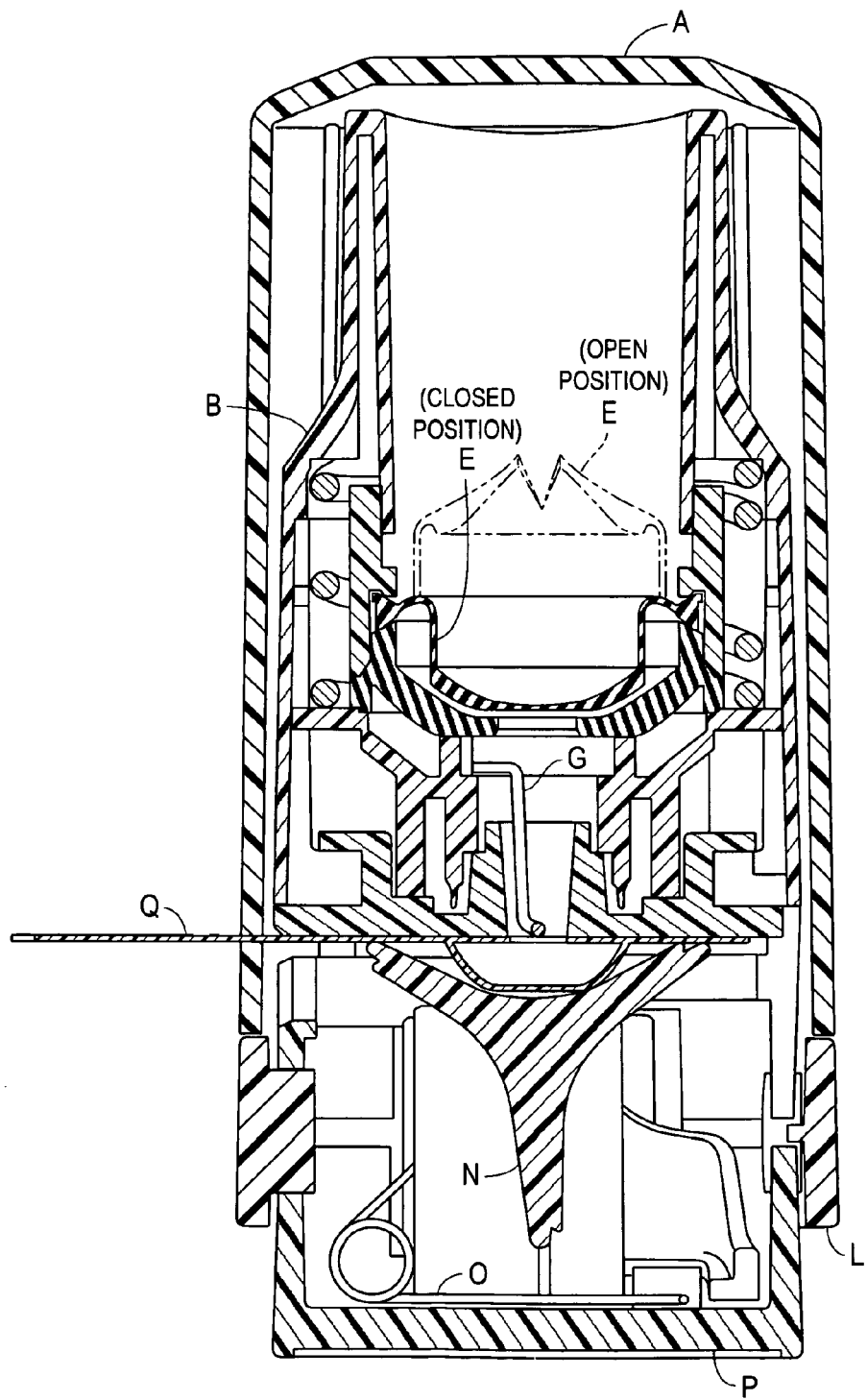
FIG. 26 shows a cut-away right-side view of the embodiment shown in FIG. 24 with a receptacle installed therein. For purposes of illustration, the trigger is shown in both the closed position and the open position.
Figure 27:
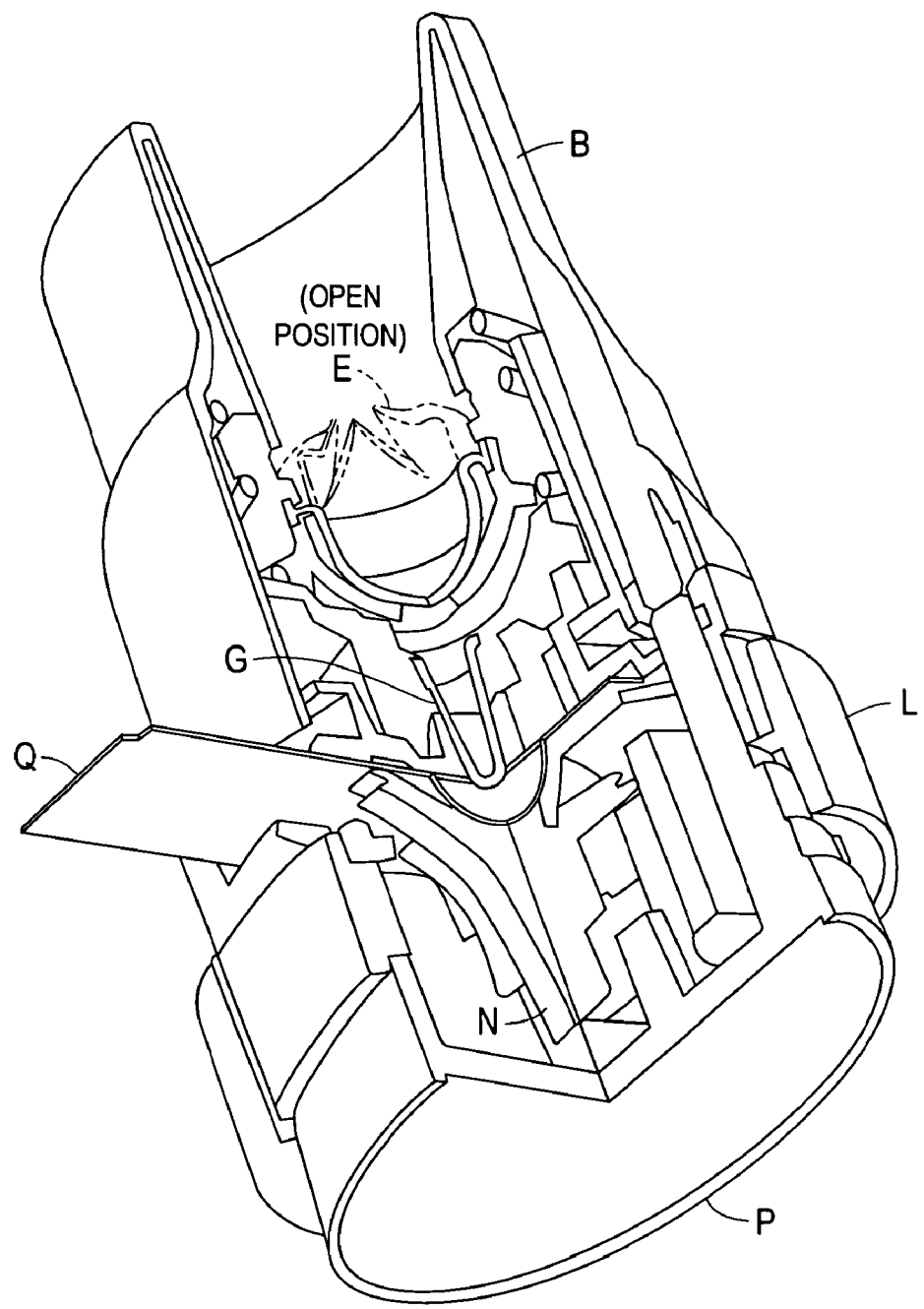
FIG. 27 shows a partially cut-away front side perspective view of the embodiment shown in FIG. 24 with a receptacle installed therein. For purposes of illustration, the trigger is shown in both the closed position and the open position.
Figure 28:
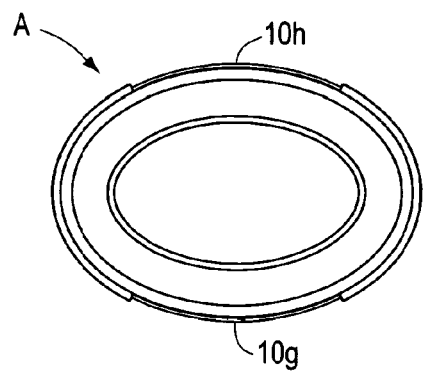
FIG. 28 shows a top view of the cap shown in FIG. 9.
Figure 29:
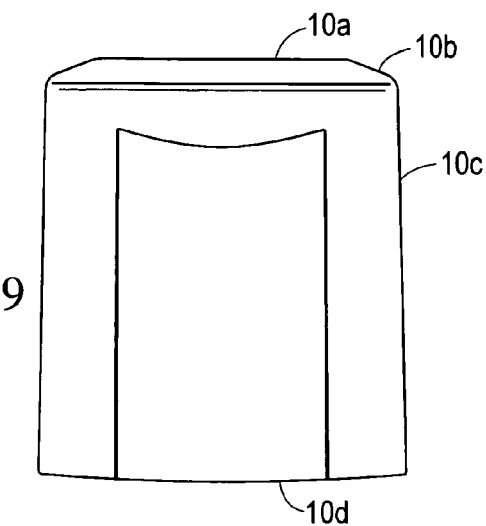
FIG. 29 shows a front side view of the cap shown in FIG. 28.
Figure 30:
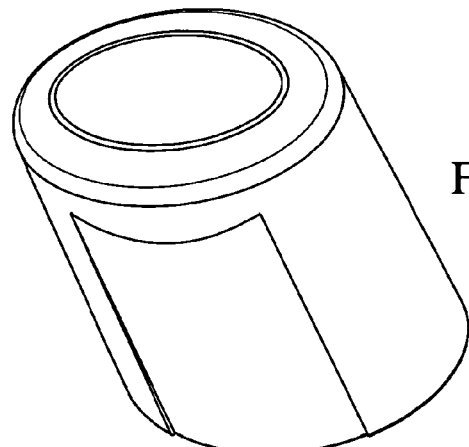
FIG. 30 shows a top front perspective view of the cap shown in FIG. 28.
Figure 31:
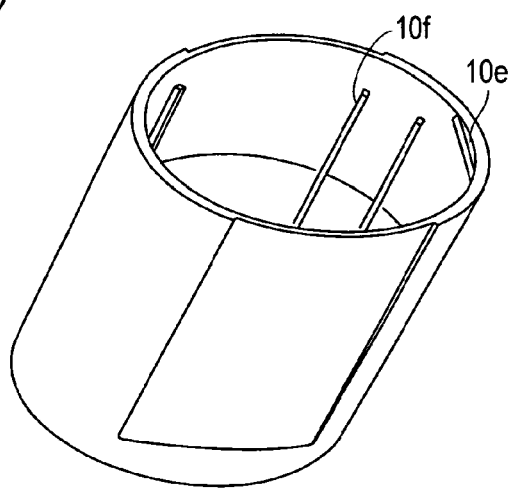
FIG. 31 shows a rear bottom perspective view of the cap shown in FIG. 28.
Figure 32:
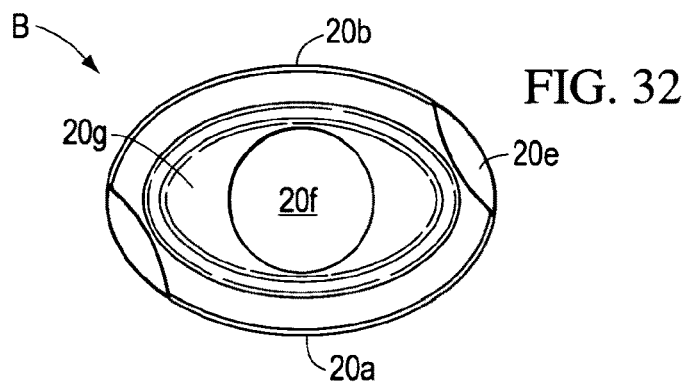
FIG. 32 shows a top view of the mouthpiece shown in FIG. 9.
Figure 33:
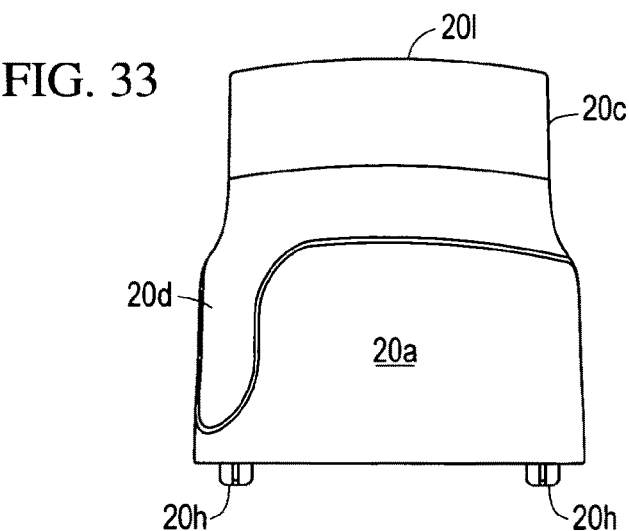
FIG. 33 shows a front side view of the mouthpiece shown in FIG. 32.
Figure 34:
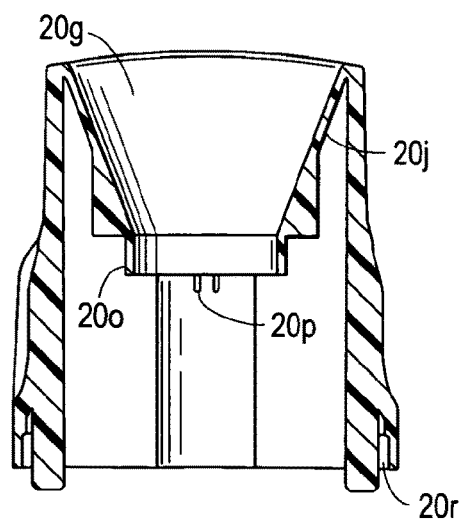
FIG. 34 shows a front side cross-section view of the mouthpiece shown in FIG. 32.
Figure 35:
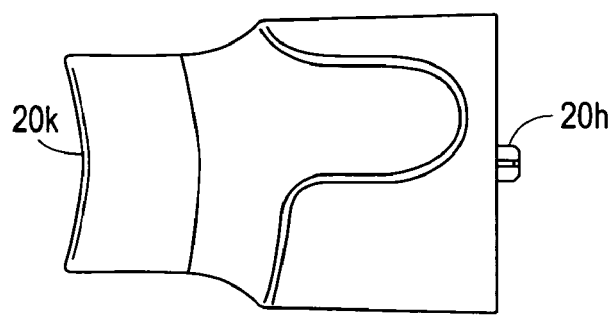
FIG. 35 shows a bottom view of the mouthpiece shown in FIG. 32.
Figure 36:
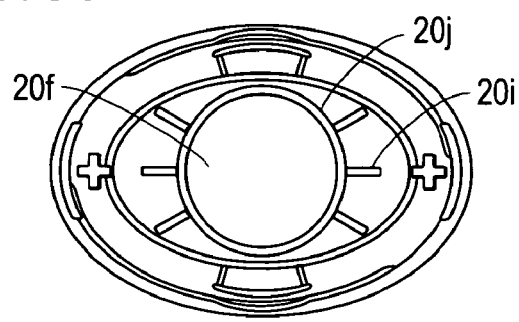
FIG. 36 shows a right side view of the mouthpiece shown in FIG. 32.
Figure 37:
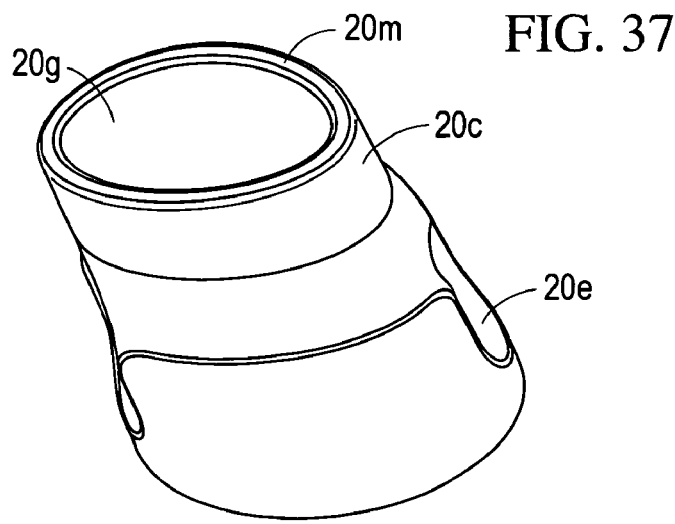
FIG. 37 shows a top front perspective view of the mouthpiece shown in FIG. 32.
Figure 38:
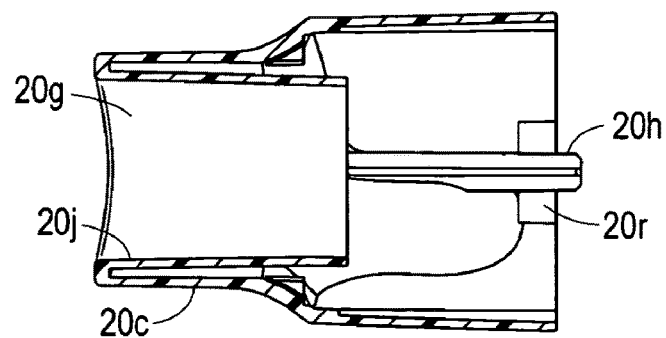
FIG. 38 shows a right side cross-section view of the mouthpiece shown in FIG. 32.
Figure 39:
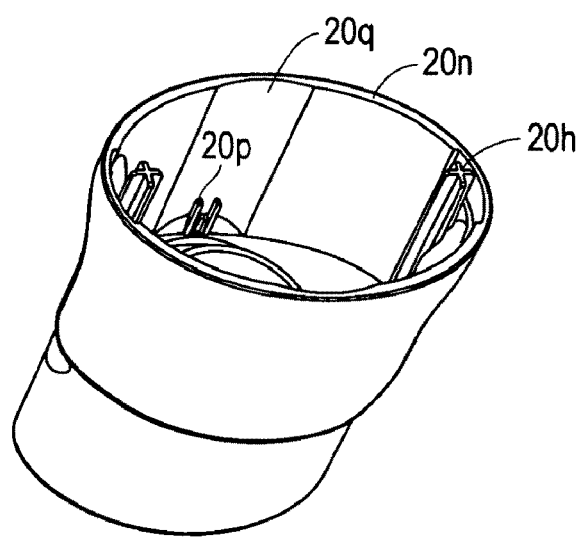
FIG. 39 shows a rear bottom perspective view of the mouthpiece shown in FIG. 32.
Figure 40:
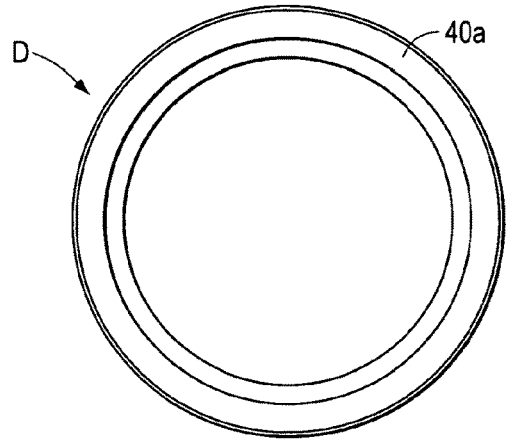
FIG. 40 shows a top view of the retainer shown in FIG. 9.
Figure 42:
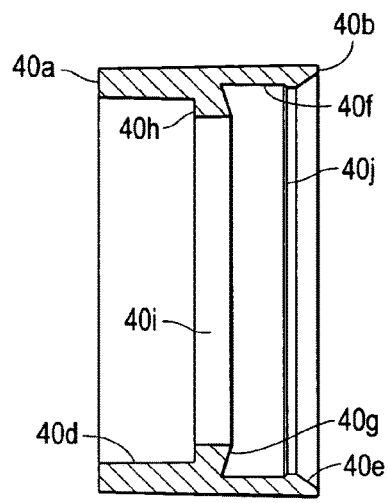
FIG. 42 shows a right side cross-section view of the retainer shown in FIG. 40.
Figure 41:
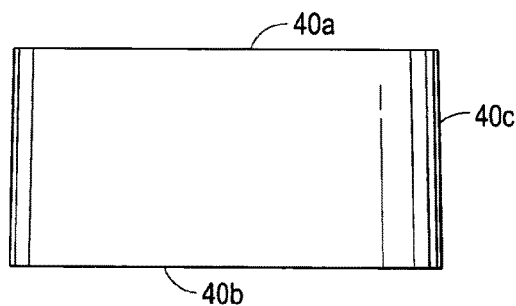
FIG. 41 shows a front side view of the retainer shown in FIG. 40.
Figure 43:
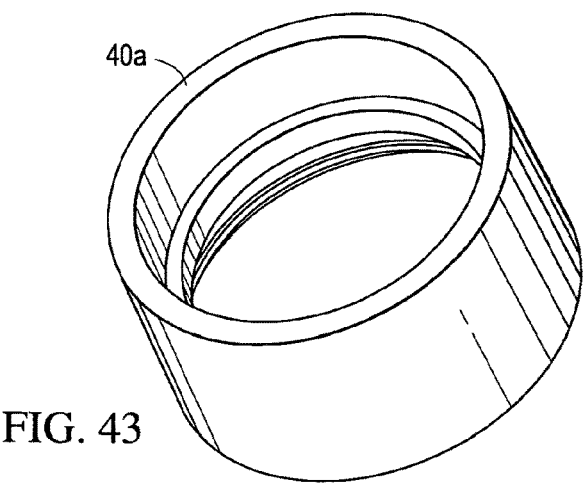
FIG. 43 shows a rear bottom perspective view of the retainer shown in FIG. 40.
Figure 99:
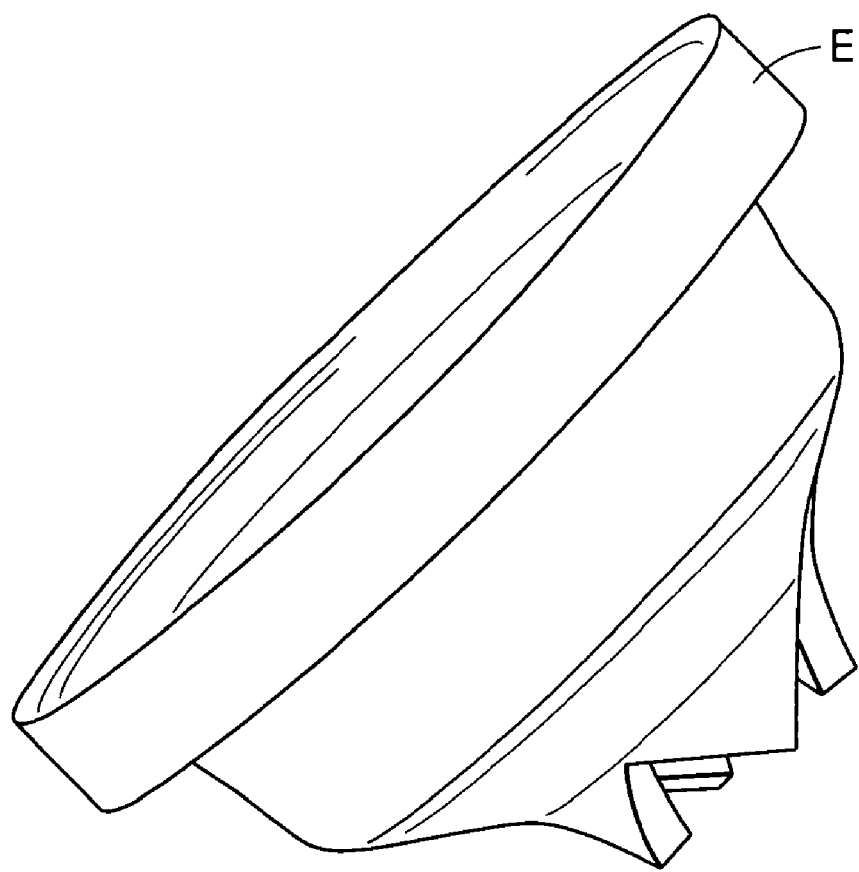
FIG. 99 shows a rear bottom perspective view of a trigger of the type shown in FIG. 9 in the open position.

FIG. 6) in the internal portion of the mouthpiece B, a trigger mechanism E located in the apparatus opens. FIG. 99 shows a trigger E in the open position and FIGS. 25-27 show the trigger E in both the open position and the closed position. The trigger mechanism E can, by way of non-limiting example, have four petals which open when a movable portion of the trigger is inverted. Although four petals is most preferred, anywhere from 3 to 6 petals is reasonable. The petals may also include other shapes, such as slits that branch off at the ends in the form of a cross fourchee.

Once the trigger E opens, outside air is allowed to flow through the apparatus and, in particular, through two primary paths. The first path is through the blister itself, with air coming into the two, e.g., 120°, arc-shaped openings and out through the center hole and into the feed tube (see FIG. 112). This air draws in the fluidized powder from the blister pack Q. The flow then goes up through the feed tube, through an orifice (e.g., through center opening of member F) and the trigger E and into the user's lungs. As the powder-laden air exits through the orifice and the trigger, the larger particles are further deagglomerated to create a fine aerosol suitable for deposition in the deep lung. Thus, in one embodiment, positioning the trigger E between the receptacle and the user results in deagglomeration of powder that would not occur if the trigger E were placed upstream of the receptacle. If the trigger E were placed upstream of the receptacle, the resistance of the trigger E would not deagglomerate powder.

The second path is for bypass air which is designed to reduce the overall resistance of the apparatus and to improve user comfort. In this regard, the overall resistance of the apparatus is usually less than 0.20 (cm H2O)$^{1/2}$/liter/minute, such as less than 0.15 (cm H2O)$^{1/2}$/liter/minute, or less than 0.10 (cm H2O)$^{1/2}$/liter/minute, at a flow rate of 40 Lpm, and typically ranges from 0.15 to 0.21 (cm H2O)$^{1/2}$/liter/minute, such as 0.16 to 0.20 (cm H2O)$^{1/2}$/liter/minute or 0.17 to 0.19 (cm H2O)$^{1/2}$/liter/minute at a flow rate of 40 Lpm. The bypass air enters the apparatus and passes through a plurality of holes 80e (see FIGS. 53-59), in the receptacle puncturing mechanism H and also serves to focus the central flow of aerosol. The number of holes may range from 2 to 10, such as 3 to 9, 4 to 8, or 5 to 7. The hole diameter typically ranges from 0.9 mm to 1.4 mm, such as 1.0 mm to 1.3 mm. The holes, however, need not be round, although round holes are relatively easy to manufacture and fine tune.

Figure 113:
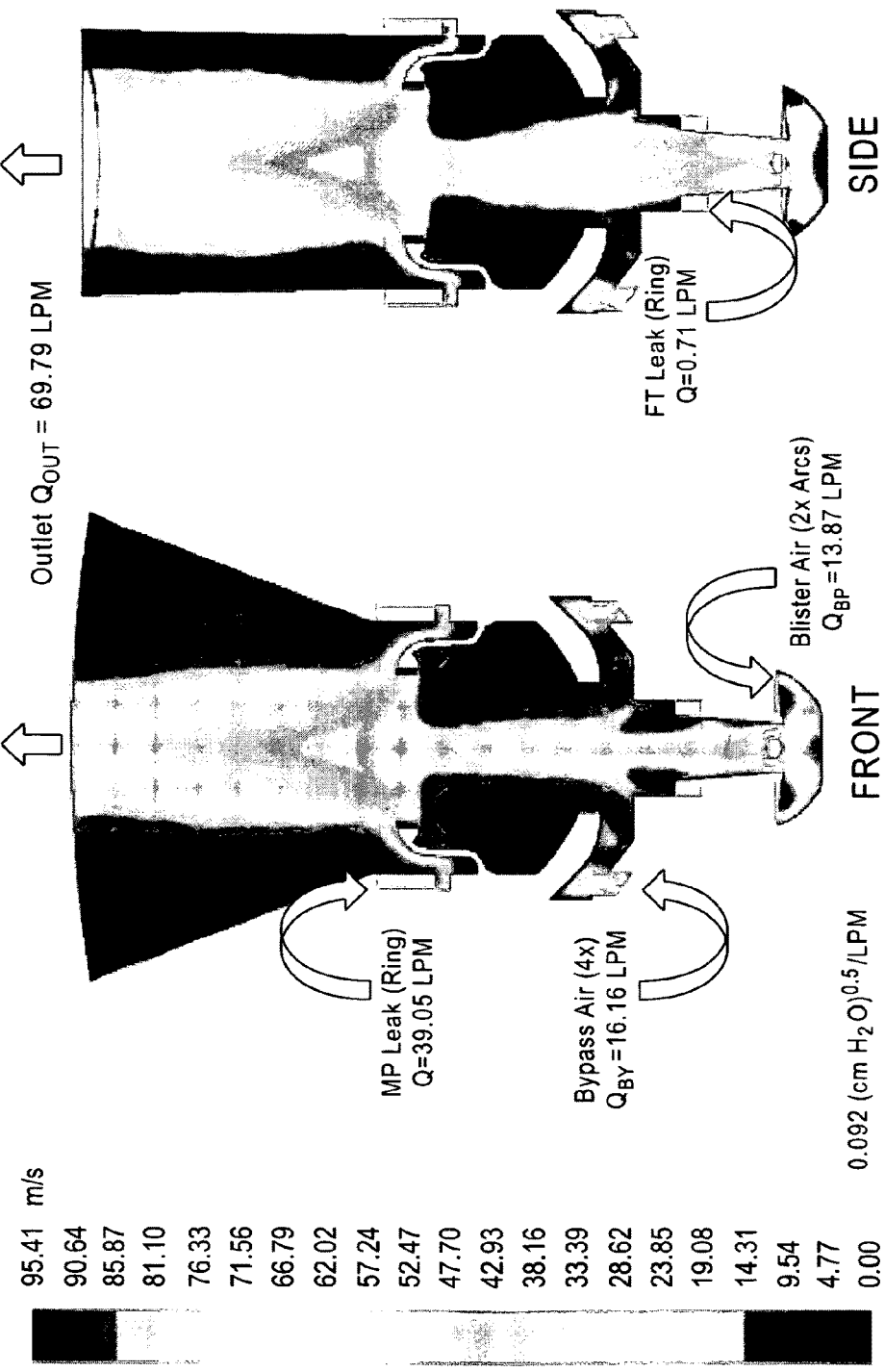
FIG. 113 shows front and side flow diagrams illustrating total air flow through the inhalation apparatus.
Figure 114:
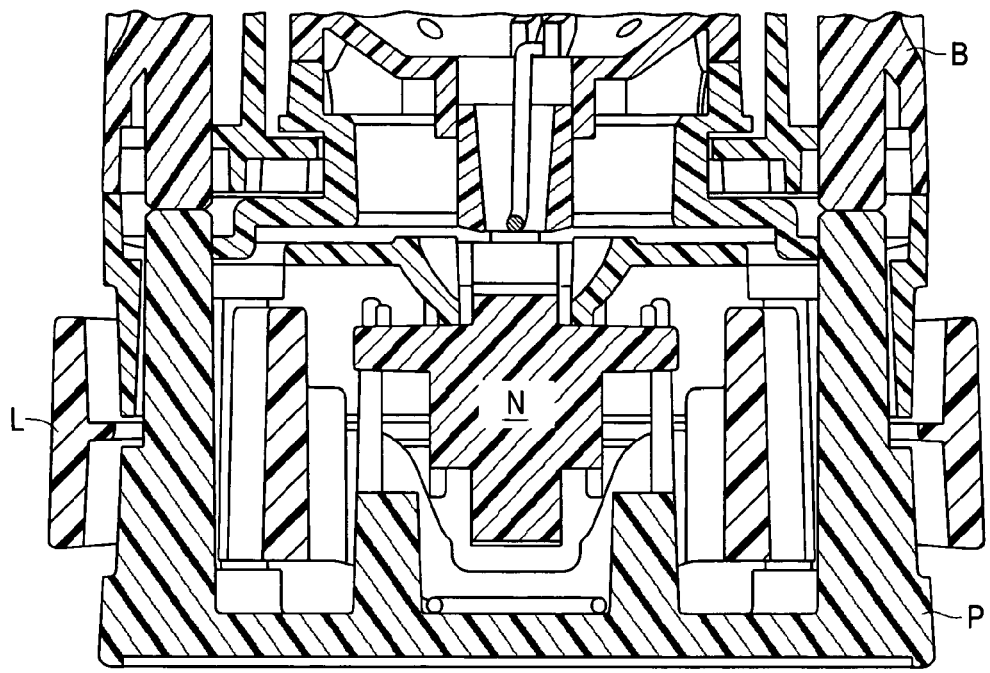
FIGS. 114-123 show various cross-section views of the inhalation apparatus as it is being used and from different angles and positions.

FIG. 113 illustrates one non-limiting way in which two flow paths can occur in the apparatus. By way of non-limiting example, the apparatus can utilize a flow rate of approximately 30 liters per minute. Also by way of non-limiting example, the air flow through the receptacle Q can be approximately 40% while the bypass air flow is approximately 60%. This helps prevent powder deposition within the apparatus, and particularly, between the cutter mechanism H and the outlet of the mouthpiece B. In some embodiments, relative to the total flow, the flow through the receptacle ranges from 30% to 50%, such as 35% to 45%, depending on the overall resistance of the device, receptacle size, and receptacle opening size. Accordingly, the bypass airflow typically ranges from 50% to 70%, such as 55% to 75%, of the total flow.

Figure 48:
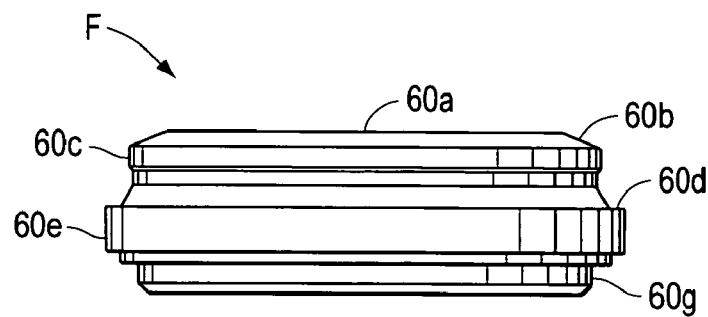
FIG. 48 shows a front side view of the orifice member shown in FIG. 9.
Figure 49:
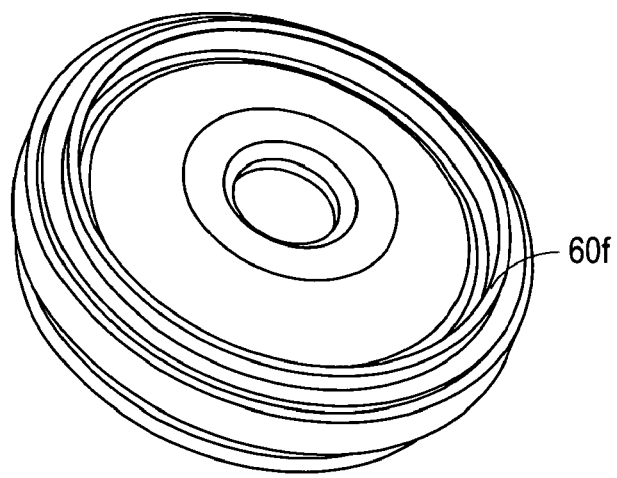
FIG. 49 shows a bottom rear side perspective view of the orifice member shown in FIG. 48.
Figure 50:
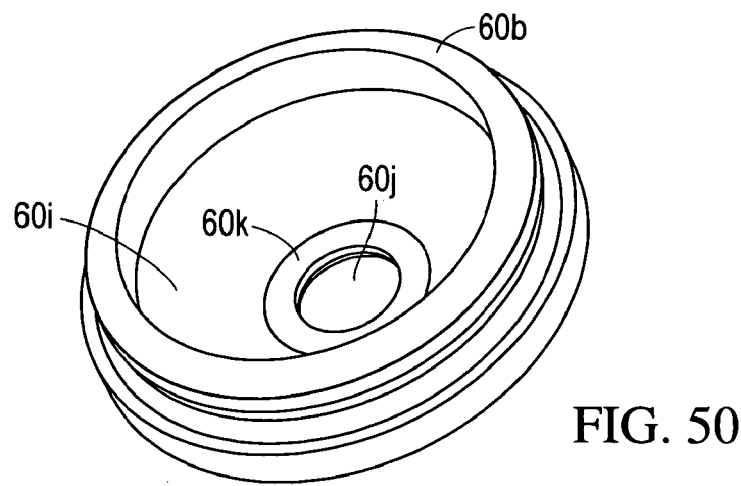
FIG. 50 shows a top side perspective view of the orifice member shown in FIG. 48.

Preferably, the apparatus is configured so that leak paths are minimized and/or optimized to provide acceptable or optimal performance of the apparatus. Key contributors to aerosol performance are the ratio of blister flow to total flow (e.g., controlled by the size of the bypass holes 80e in the receptacle puncturing mechanism H), the size of the orifice 60j (see FIGS. 48-50), and the length of the slits 50c and 50d (see FIGS. 58-67) of the trigger E. By way of non-limiting example, blister/total flow ratios can be between 20% to 70%, such as from 25% to 65%, 30% to 60%, or 35% to 55%, and orifice 60j sizes or diameter can be between 3 mm and 13 mm, such as between 4 mm and 12 mm, or 5 mm and 11 mm. Also by way of non-limiting example, trigger slit length (determined by the smallest diameter circle which fully encloses or encircles the generally X-shaped slits 50c and 50d) can range from 0.2 inches to 0.6 inches, such as 0.3 inches to 0.5 inches, and can be approximately 0.34 inches. In this regard, the trigger slit length typically ranges from 50% to 80%, such as 60% to 70%, of the diameter of the active (non-clamped) portion of the trigger.

One function of the trigger E is to ensure consistent and uniform dosing. In this regard, assuming the trigger E opens, the trigger E opens at generally the same threshold vacuum pressure regardless of the user or user's effort. Once the trigger E opens, the flow rate through the device typically reaches its peak within 20 ms, e.g., within 15 ms or within 10 ms.

The trigger E is typically self-closing, which eliminates the need for resetting the trigger E. When the vacuum is removed, i.e., when the patient stops inhaling, the trigger E is biased back into its original position.

Typically, the trigger E is also self-deoccluding. The opening and closing of the trigger E prevents powder from accumulating thereon.

As explained above, in addition to forming the central hole in the blister pack, the deoccluding device G also serves to clean the feed tube FT (see FIGS. 66-72) with each use. This functions as follows: with each rotation (e.g., 180 degree rotation) of the mouthpiece B, the deoccluding device G deoccludes the inside of the feed tube FT, thereby minimizing the amount of powder left on the inner surface. This prevents long-term buildup on the feed tube FT and extends the life of the apparatus. In this embodiment, the feed tube FT does not enter the receptacle Q. Alternatively, the access surface can be pierced simultaneously with the insertion or engagement with the feed tube FT. The feed tube FT can be made to not have jets or ejector tubes within the flow path, and the clear, undisrupted flow path can thereby reduce any tendency for the feed tube FT to clog or otherwise lose dispersion efficiency.

Thus, the invention provides for a breath-actuated dry powder inhaler which can generally be used for any dry powder, e.g., dry powder insulin. For example, the apparatus may be used with the dry powder described in U.S. Provisional application Ser. No. 61/000,543, filed concurrently herewith, which is incorporated herein by reference. In this regard, the apparatus may be used, e.g., with a dry powder pharmaceutical composition comprising, in percent by weight: from about 60% to about 95% insulin; and from about 5% to about 30% buffer; wherein when the composition is dissolved at a concentration of 1 mg/ml in distilled water to form a solution, the solution has a pH greater than or equal to 7.5.

In some cases, after the powders are filled into the receptacle, they are conditioned as described in U.S. Provisional application Ser. No. 61/000,627, filed concurrently herewith, which is incorporated herein by reference. The present is generally used with dry powders having an MMD and/or MMAD of less than 30 μm, such as less than 20 μm or less than 10 μm, and MMD and/or MMAD typically range from 1 μm to 10 μm, such as 1 μm to 5 μm.

The apparatus disclosed herein is significantly smaller than known devices while also having comparable performance. By way of non-limiting example, the apparatus can be designed to have a one-month useful life and does not require any deoccluding or replacement of parts by the user. The device can therefore be made disposable. The apparatus is also preferably easier to use, is ergonomic, and has a look-and-feel which is more desirable than known devices. Still further, the apparatus can be made small and lightweight for easy storage and can desirably easily fit within a user's shirt or pants pocket. The apparatus also desirably fits in the palm of the user and requires few puffs for a dose, e.g., 1 to 4 puffs, such as 1 to 3 puffs or 1 to 2 puffs.

Figure 2:
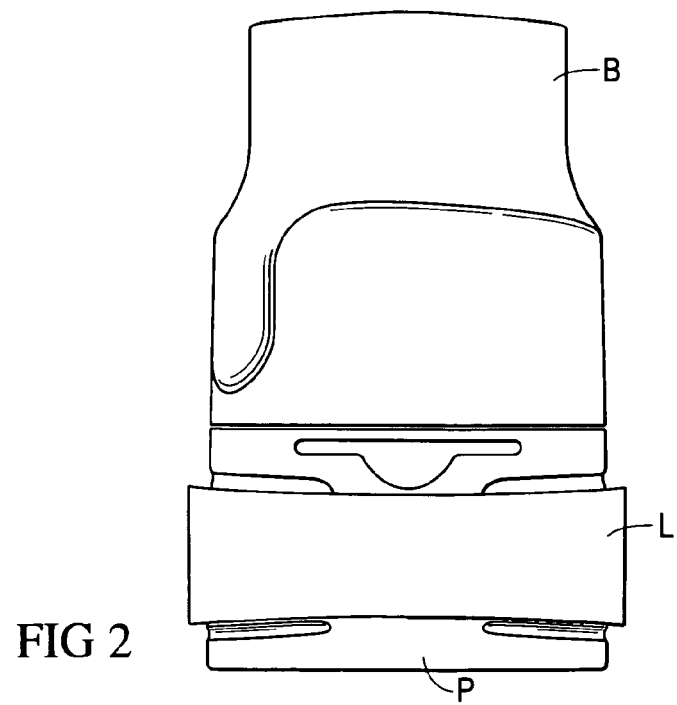
FIG. 2 shows a front side view of the embodiment of FIG. 1 with the cover removed.

Referring now specifically to FIGS. 1 and 2, there is shown a non-limiting embodiment of the apparatus according to the invention. The apparatus may have a height "h" which is typically 50 mm to 80 mm, such as approximately 60 mm and a width "w" which is typically 30 mm to 60 mm, such as approximately 40 mm, and a depth is typically 20 mm to 50 mm, such as approximately 30 mm. There is a lot of flexibility on the overall height. The depth is the dimension that is most sensitive to the user, with smaller dimensions being preferred. There is some flexibility in the width. FIG. 1 shows the apparatus with a cap or protective cover A installed thereon and FIG. 2 shows the apparatus with the cap A removed. As is shown in FIG. 2, with the cap A removed, an opening, which is configured to receive a receptacle, e.g., blister pack, is now accessible to the user.

FIGS. 3-8 show one non-limiting way in which the apparatus of the type described herein and, in particular, of the type shown in FIGS. 1-2 can be used by a user. FIG. 3 shows the apparatus prior to the cap A being removed. As the arrow demonstrates, the cap A can be removed by merely lifting the cap A vertically. The cap A is also configured and therefore capable of being mated with or mounted to the bottom portion of the apparatus to prevent its loss and to increase the surface area available to the user for gripping the apparatus during use. With the cap removed, FIG. 4 shows how a receptacle Q can be inserted into the opening in the apparatus. As the arrow demonstrates, the receptacle Q can be slid into the opening of the apparatus horizontally. Once the receptacle Q is inserted to a home or maximum insertion position (note that a tab portion of the receptacle remains outside the apparatus allowing a user to grip the receptacle when it its required to be removed), FIG. 5 shows how an upper housing portion (i.e., the housing portion containing the mouthpiece B) of the apparatus can be rotated to activate the apparatus. It should be noted that during this insertion movement, the apparatus automatically performs the following functions: the lock system M is moved to the unlocked position and the receptacle impacting member N is activated so as to impact a tub portion of the receptacle Q. As the arrow demonstrates, the upper housing portion or mouthpiece B can be rotated clockwise. The angle of rotation in this embodiment is about 180 degrees. However, it should be noted that such rotation would not be possible unless the receptacle Q has been properly inserted. Thus, rotation is made possible because the lock system N has moved to the unlocked position by proper insertion of the receptacle Q. Furthermore, during this rotation, the apparatus automatically performs the following functions: the air inlet openings and the central outlet opening are formed (e.g., as is shown in FIG. 102) in the foil lidstock of the receptacle Q and the inside of the feed tube FT is deoccludeed by the deoccluding device G. FIG. 6 shows how the air flow can come out through the mouthpiece B. Of course, this will occur when the user places his or her lips on the mouthpiece B and inhales by an amount that is sufficient to open the trigger E. FIG. 7 shows how a spent or used receptacle Q can be removed from the opening in the apparatus. As the arrow demonstrates, the receptacle Q can be slid out of the opening of the apparatus horizontally. Once the receptacle Q is removed (note that the tab portion of the receptacle outside the apparatus is gripped by the user and the receptacle Q is pulled out), the user can insert another receptacle for another inhalation treatment or they can place the cap A back onto the apparatus as is shown in FIG. 8. Thus, this embodiment is intuitive and easy to use, requiring only 6 steps.

Figure 9:
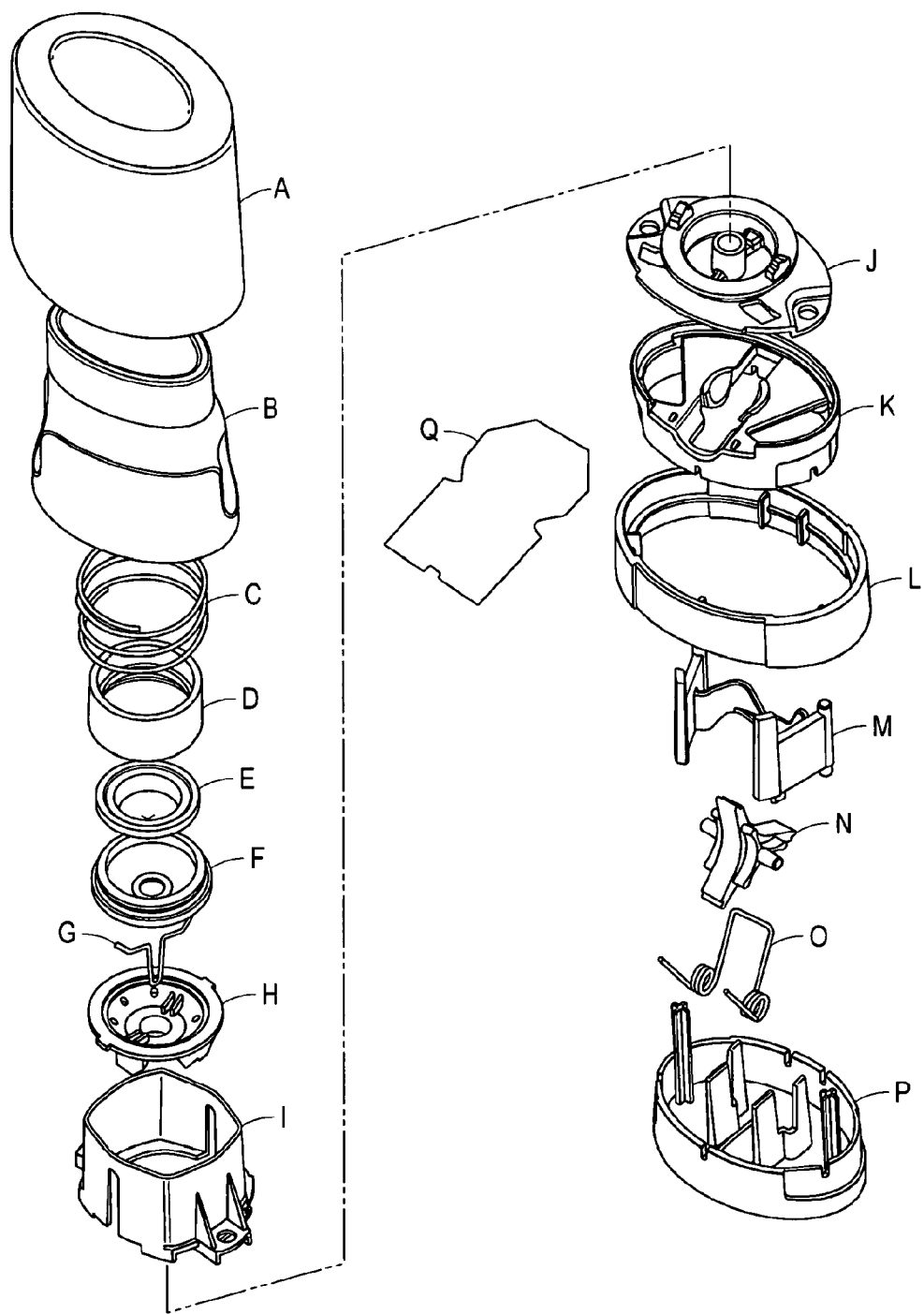
FIG. 9 shows an exploded view of another embodiment of the invention.

FIGS. 9-24 show one non-limiting way in which the apparatus shown in FIGS. 1-2 can be assembled. FIG. 9 shows an exploded view of the apparatus: component A represents the cap; component B represents the mouthpiece; component C represents a coil compression spring; component D represents a retainer or retainer member; component E represents the trigger; component F represents the orifice member; component G represents the deoccluding and puncturing device; component H represents the receptacle puncturing mechanism; component I represents the upper bearing member; component J represents the lower bearing member; component K represents the support body member; component L represents the skirt; component M represents the lock member; component N represents the receptacle impacting member; component O represents a torsion spring; and component P represents the lower housing part. Furthermore, component Q represents a receptacle which can be used with the apparatus.

In view of the above, the part count of the above embodiment is 16 parts. By combining and/or eliminating parts, the part count may be 16 or less, such as 15 or less, 14 or less, 13 or less, or 12. In this regard, component F may be omitted. Component J and the outer portions of components K and P may be combined. Components O and M and the inner portion of component K may be combined. In some embodiments, component E may be omitted.

By way of non-limiting example, at least components A, B, D, F, H-N, and P can made by injection molding and can be made of materials conventionally used in, e.g., commercially available insulin inhalation devices. Non-limiting materials include a wide range of plastics, such as PVT, ABS, polycarbonates, and liquid crystal polymers. Commercially available plastics include Ticona Celanex MT2401 or MT2402 (PBT), GE Cycoloy C1950 or C1204HF (PC/ABS), Basell ProFax PF-511 (PP). More specifically, the cap or component A can be made of PP supplied by Basell or PC/ABS supplied by GE, and the material can have a grade of ProFax PF-511 or a grade of Cycoloy C1950 or C1204HF. The mouthpiece or component B can be made of PC/ABS supplied by GE, and the material can have a grade of Cycoloy C1950 or C1204HF. The trigger retainer or component D can be made of PP supplied by Basell, Ticona Celanex MT2401 or MT2402 (PBT), or PC/ABS supplied by GE, and the material can have a grade of ProFax PF-511 or a grade of Cycoloy C1950 or C1204HF. The trigger E can be made of an elastomer, e.g., silicone or thermoplastic elastomers. The orifice member or component F can, e.g., be made of PP supplied by Basell or PC/ABS supplied by GE, and the material can have a grade of ProFax PF-511 or a grade of Cycoloy C1950 or C1204HF. The orifice member F may be made of rubber to allow flexing and self-deoccluding. The cutter mechanism or component H can, e.g., be made of PBT supplied by Ticona and the material can have a grade of Celanex MT2401 or MT2402. The upper bearing member or component I can, e.g., be made of PC/ABS supplied by GE, and the material can have a grade of Cycoloy C1950 or C1204HF. The lower bearing member or component J can, e.g., be made of PC/ABS supplied by GE or PBT supplied by Ticona and the material can have a grade of Cycoloy C1950 or C1204HF or a grade of Celanex MT2401 or MT2402. The body member or component K can, e.g., be made of PC/ABS supplied by GE, and the material can have a grade of Cycoloy C1950 or C1204HF. The skirt or component L can, e.g., be made of PC/ABS supplied by GE, and the material can have a grade of Cycoloy C1950 or C1204HF. The lock member or component M can, e.g., be made of PC/ABS supplied by GE, and the material can have a grade of Cycoloy C1950 or C1204HF. The receptacle impact member or component N can, e.g., be made of PC/ABS supplied by GE, and the material can have a grade of Cycoloy C1950 or C1204HF. The lower housing or component P can, e.g., be made of PC/ABS supplied by GE, and the material can have a grade of Cycoloy C1950 or C1204HF.

Figure 10:
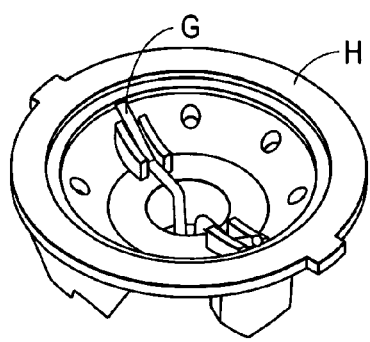
FIG. 10 shows how the deoccluding device and the cutter mechanism shown in FIG. 9 are assembled together.
Figure 11:
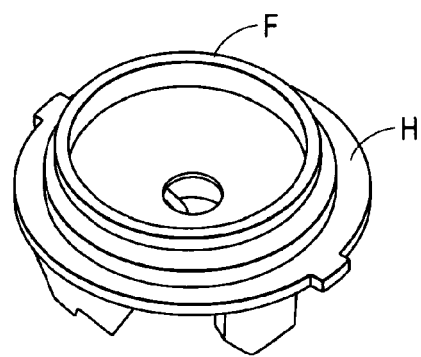
FIG. 11 shows how the orifice member and the subassembly shown in FIG. 10 are assembled together.
Figure 12:
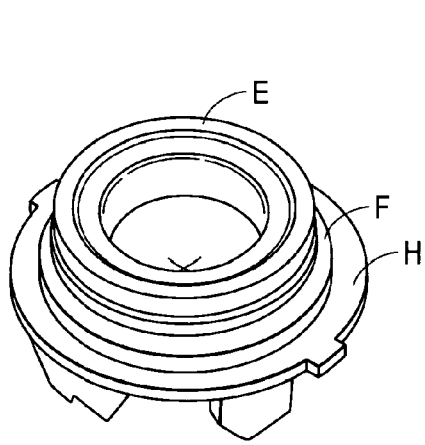
FIG. 12 shows how the trigger member and the subassembly shown in FIG. 11 are assembled together.
Figure 13:
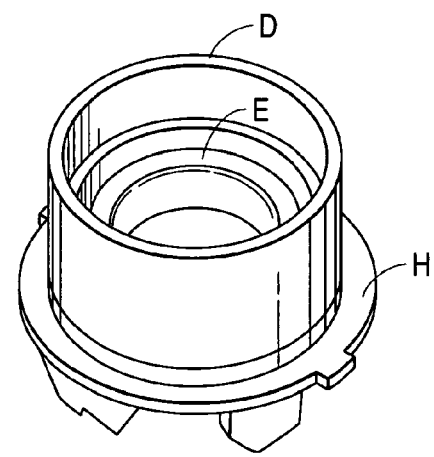
FIG. 13 shows how the retainer member and the subassembly shown in FIG. 12 are assembled together.
Figure 14:
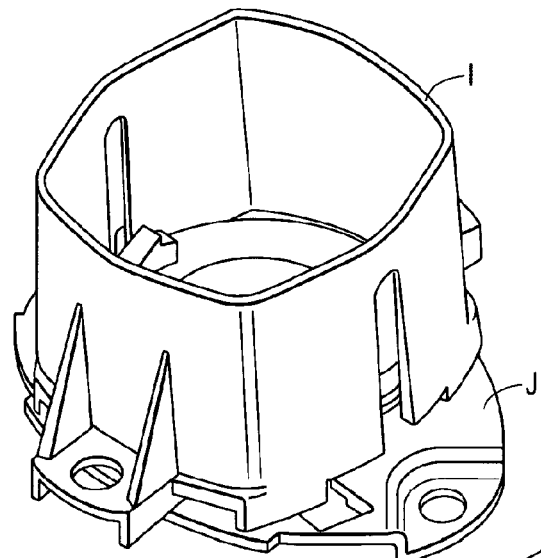
FIG. 14 shows how the upper bearing member and the lower bearing member shown in FIG. 9 are assembled together.
Figure 15:
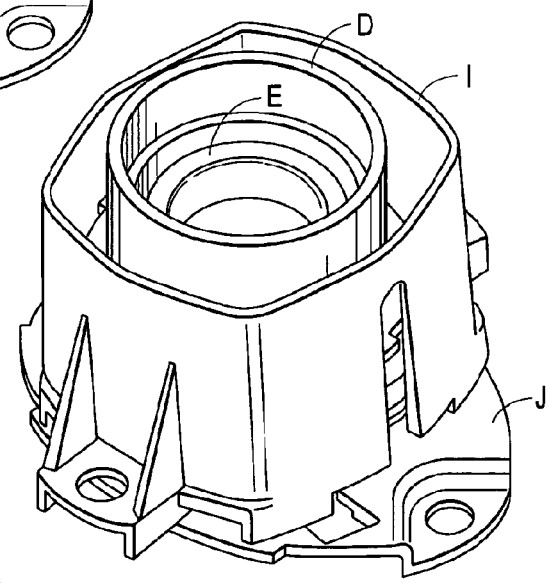
FIG. 15 shows how the subassembly shown in FIG. 13 and the subassembly shown in FIG. 14 are assembled together.
Figure 16:
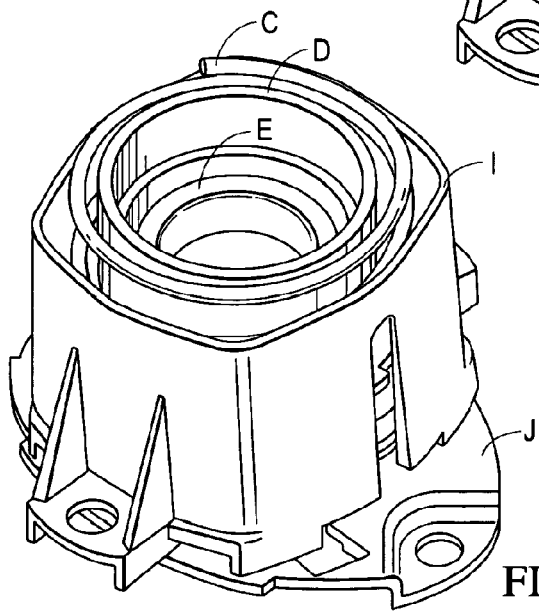
FIG. 16 shows how the coil spring and the subassembly shown in FIG. 15 are assembled together.
Figure 17:
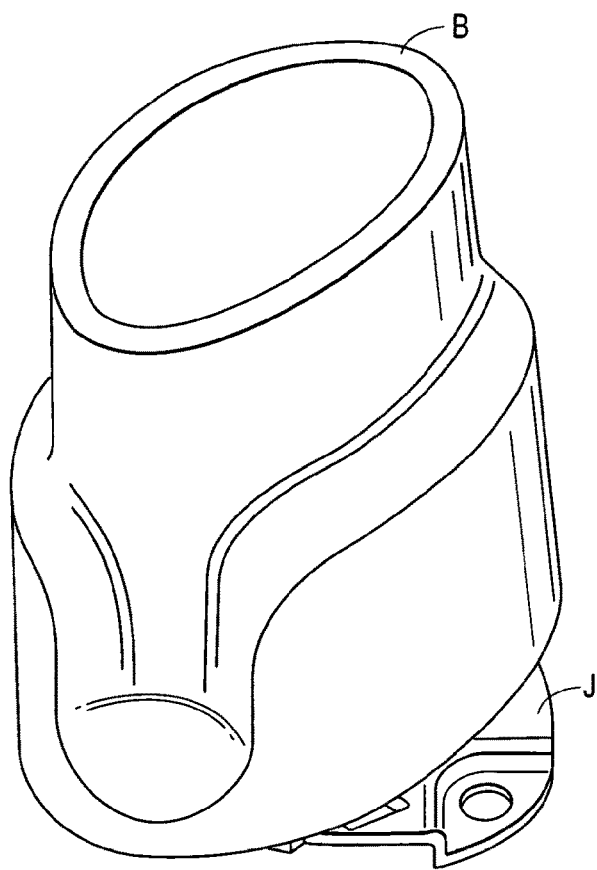
FIG. 17 shows how the mouth piece and the subassembly shown in FIG. 16 are assembled together.
Figure 18:
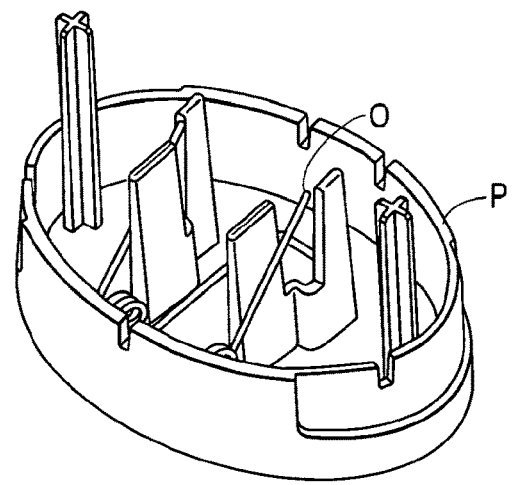
FIG. 18 shows how the bottom housing member and the torsion spring shown in FIG. 9 are assembled together.
Figure 20:
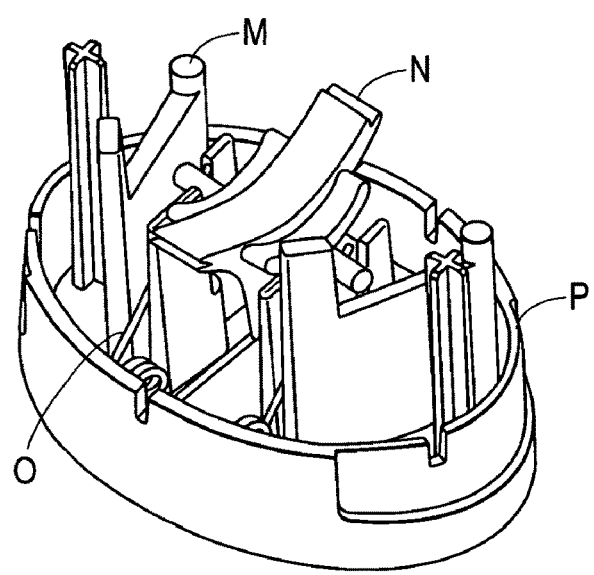
FIG. 20 shows how the lock member and the subassembly shown in FIG. 19 are assembled together.
Figure 21:
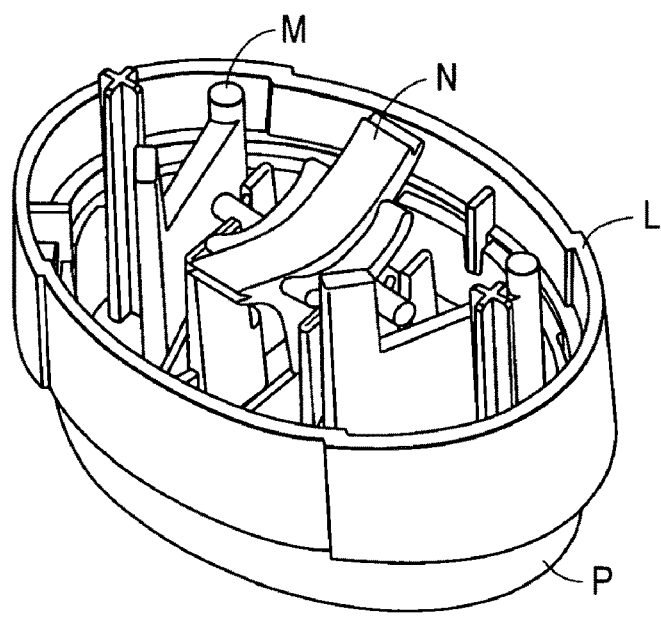
FIG. 21 shows how the skirt member and the subassembly shown in FIG. 20 are assembled together.
Figure 22:
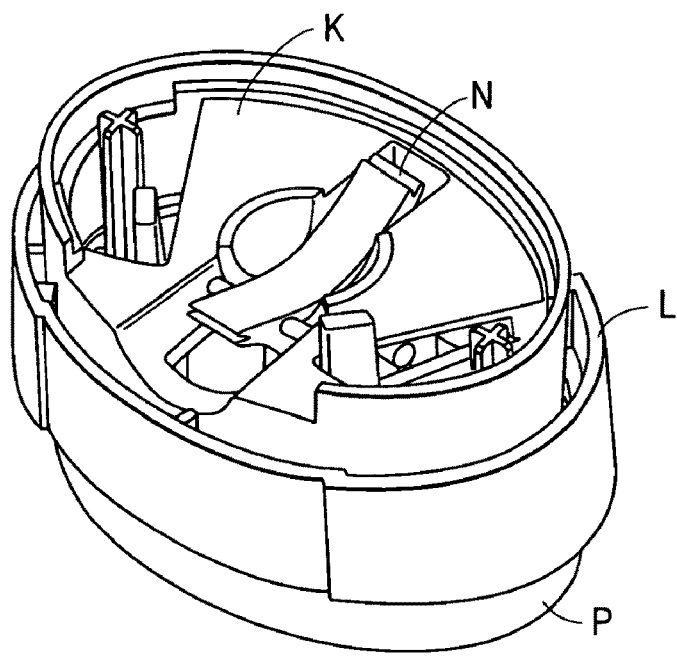
FIG. 22 shows how the body member and the subassembly shown in FIG. 21 are assembled together.
Figure 24:
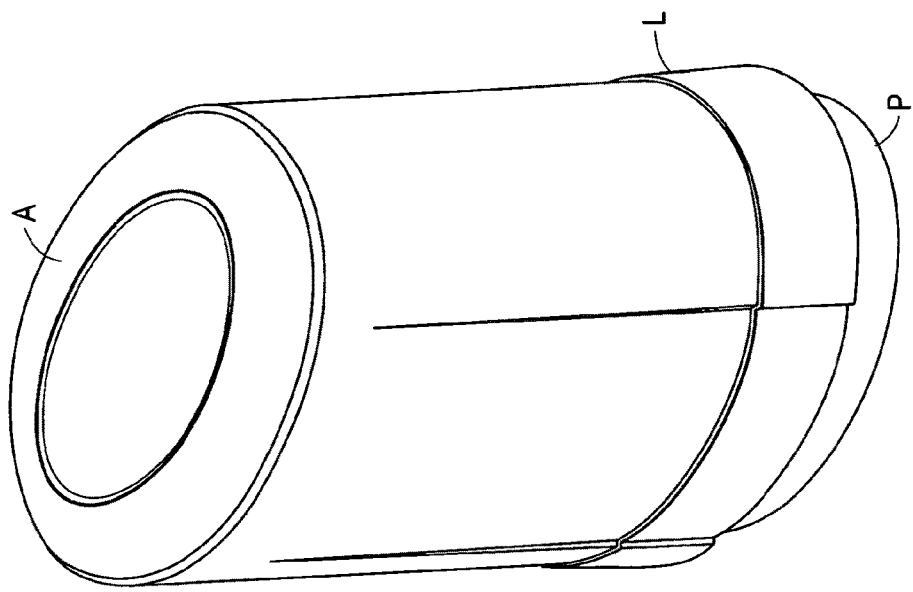
FIG. 24 shows how the cover member and the subassembly shown in FIG. 23 are assembled together.
Figure 23:
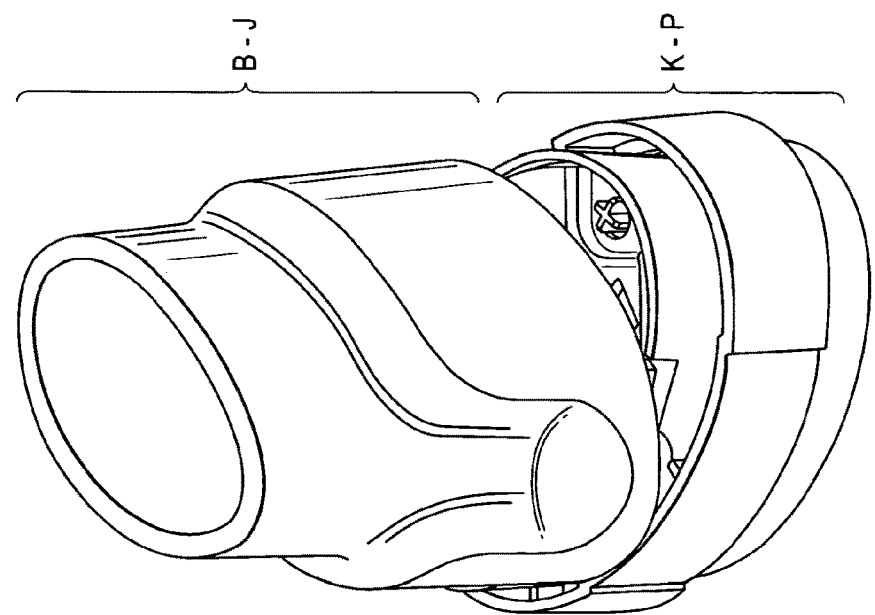
FIG. 23 shows how the subassembly shown in FIG. 17 and the subassembly shown in FIG. 22 are assembled together.

With reference to FIGS. 10-24, the apparatus can, e.g., be assembled as follows: FIG. 10 shows how the deoccluding and puncturing device G can, e.g., be seated inside the receptacle puncturing mechanism H. Next, as shown in FIG. 11, an orifice member F can, e.g., be mounted to the cutter mechanism H. The orifice member F is optional and can, e.g., be omitted from the apparatus. As shown in FIG. 12, the trigger E can then be mounted to the orifice member F. Next, as shown in FIG. 13, the retainer member D is mounted over the trigger E. FIG. 14 shows how the upper bearing member I is mounted to the lower bearing member J. Next, as shown in FIG. 15, the sub-assembly of components D-H are mounted within the upper bearing member I. FIG. 16 shows the spring C thereafter being mounted within the upper bearing member I. The mouthpiece B can then be mounted to the sub-assembly of components C-J as shown in FIG. 17. FIG. 18 shows how the torsion spring O can, e.g., be mounted to the lower housing member P. FIG. 19 shows how the receptacle impacting member N can, e.g., be mounted to the lower housing member P and the torsion spring O. FIG. 20 shows how the lock member M can then be mounted to the lower housing member P. Next, FIG. 21 shows how the skirt L is mounted to the lower housing member P. FIG. 22 shows how the housing member K is mounted to the skirt L and the lower housing member P. Next, as shown in FIG. 23, the sub-assembly of components B-J are mounted to the sub-assembly of components K-P. FIG. 24 shows the fully assembled apparatus after assembly and with the cap A installed thereon.

FIGS. 25-27 show various cross-sectional views of one non-limiting embodiment of the apparatus shown in FIGS. 1-2. FIG. 25 shows a cross-section view of FIG. 1. FIG. 26 shows a cross-section view of FIG. 2 turned 90° relative to FIG. 25. FIG. 27 shows a cut-away perspective view of the apparatus shown in FIGS. 1-2. In each of FIGS. 25-27, the trigger E is shown in both the closed position and the open position (for purposes of illustration) and a receptacle Q is positioned in the home position or fully inserted position. Of course, the trigger E would not normally be opened, and the receptacle would not normally be inserted, while the cap is still installed thereon.

FIGS. 28-31 show various views of one non-limiting embodiment of the cap A shown in FIG. 9 and illustrate the various features thereof. The cap A covers and protects mouthpiece B and the receptacle insertion slot S from ingress of dirt and debris between uses.

As is shown in FIGS. 28-31, the cap A in this embodiment has a generally oval configuration and includes a front section 10*g* and a rear section 10*h*. The cap A also has a closed upper end 10*a* and an open lower end 10*d* which is sized and shaped to slide over the mouthpiece B. In order to ensure that the cap A is removably secured to the apparatus, the cap A utilizes two oppositely arranged projections 10*e* which are configured to engage with indentations formed in member J. The cap A also utilizes internal elongated projections 10*f* which are configured to frictionally engage with outer surfaces of the mouthpiece B so as to prevent the cap A from moving excessively laterally when installed on the apparatus. The cap A can be inverted onto the bottom of the device during dosing to provide additional grip surface. Of course, other configurations and shapes for the cap A are contemplated. Additionally, the cap A can, e.g., be made of the materials described above and can even be made transparent or translucent. Still further, the cap A can also be dispensed with (or replaced with a removable plug-type cap which fits within the exit opening of the mouthpiece B) as it is not required for a proper functioning apparatus.

FIGS. 32-39 show various views of one non-limiting embodiment of the upper housing portion or mouthpiece B shown in FIG. 9 and illustrate the various features thereof. In general, the mouthpiece B generally provides a smooth, elliptical surface to seal against the user's lips during inhalation.

As is shown in FIGS. 32-39, the mouthpiece B in this embodiment has a generally oval configuration and includes a front section 20*a* and a rear section 20*b*. The mouthpiece B also has a closed upper end 20*c* which is sized and configured to allow a user's lips to sealingly engage with the mouthpiece B and thereby allow the user to breathe in without any significant leakage between the user's lips and the upper end 20*c*. The mouthpiece B is shaped to keep the user's tongue from getting in the way, which increases the emitted dose and reproducibility of results. In this regard, the mouthpiece B has a length sufficient to protrude past the teeth of the user.

The mouthpiece B also has an open lower end 20*n* which is sized and shaped to slide over the upper bearing member I. In order to ensure that the mouthpiece B is removably secured to the apparatus, the mouthpiece B utilizes two oppositely arranged projections 20*h* whose free ends are configured to enter openings 90*d* and to become fixed to portions 90*c* formed on upper bearing member I by, e.g., ultrasonic welding, swaging, etc. The projections 20*h*, thus, function as internal ribs on the major axis of the mouthpiece B and may facilitate ultrasonic welding of upper subassembly B-J. The projections 20*h* can each have a generally T-shaped cross-section. The mouthpiece B also utilizes finger engaging indentations or grips 20*d* and 20*e* which are ergonomically shaped to allow the user to grip the mouthpiece B with the thumb and forefinger when the user rotates the mouthpiece B.

The mouthpiece B additionally also utilizes a generally oval-shaped diverging exit opening 20*g* which extends from upper edge 20*l*/20*k* to a generally circular opening 20*f*. The generally oval-shaped diverging exit opening 20*g* allows the aerosolized powder to expand as it moves from the opening 20*f* to exit opening edge 20*l*/20*k*. The front and back exit opening edges 20*l* each have a generally outward curving shape whereas the left and right exit opening edges 20*k* each gave a generally inwardly curving shape.

A plurality of reinforcing ribs 20*i* is arranged on the wall 20*j*, which forms the generally oval-shaped diverging exit opening 20*g*. The plurality, e.g., eight, of reinforcing ribs 20*i* provides support for compression spring C. The generally circular opening 20*f* is defined by a generally circular wall which includes an outer circumferential surface 20*o*. The outer circumferential surface 20*o* is sized and shaped to slide within (see FIGS. 25-27) and/or sealingly engage with inner circumferential surface 40d of member D.

A pair of inwardly projecting spaced-apart ribs 20p is arranged on each of the walls which form the front and back sections 20a and 20b. Each oppositely arranged pair of ribs 20p are sized and configured to slide within the oppositely arranged slots 90f and 90g of the upper bearing member I. Each oppositely arranged pair of ribs 20p is also arranged on one of two oppositely arranged curved indentations 20q. These indentations 20q are sized and configured to receive therein outwardly curved projecting portions 90m of the upper bearing member I.

The mouthpiece B also utilizes oppositely arranged indentations 20r, which are sized and configured to receive therein outwardly curved free ends of the projecting portions 90b and 90c of the upper bearing member I. The projections 20h, the indentations 20q and 20r, and the projections 20p all function to couple the upper bearing member I to the mouthpiece B and ensure that the mouthpiece B causes rotation of the upper bearing member I when the mouthpiece B is rotated. Of course, other configurations and shapes for the mouthpiece B are contemplated. Additionally, the mouthpiece B can, e.g., be made of the materials described above and can even be made transparent or translucent.

FIGS. 40-43 show various views of one non-limiting embodiment of the retainer member D shown in FIG. 9 and illustrate the various features thereof. The retainer member D fits against the orifice member F. An upper portion of the retainer member D is slidingly sealed against mouthpiece B.

As is shown in FIGS. 40-43, the retainer D has a generally circular sleeve configuration and includes an open upper end 40a and an open lower end 40b. The retainer D has a generally cylindrical outer surface 40c and an inner generally cylindrical surface 40d which is sized and configured to sealingly engage with the cylindrical surface 20o of the mouthpiece B. The retainer D also has an upper shoulder surface 40h and a lower shoulder surface 40g formed in an inwardly projecting circumferential projection 40i. The lower shoulder surface 40g and the inner circumferential surface 40f are sized and configured to correspondingly sealingly engage with surfaces 50h and 50e of the trigger E. An inwardly projecting circumferential projection 40j is sized and configured to correspondingly sealingly and lockingly (and/or non-removably) engage with circumferential projection 60c of the orifice member F. To facilitate the connection between the retainer D and the orifice member F (after the trigger E has been inserted inside of the retainer D), the retainer D utilizes a chamfered portion 40e. Of course, other configurations and shapes for the retainer D are contemplated. Additionally, the retainer D can, e.g., be made of the materials described above and can even be made transparent or translucent.

FIGS. 44-47 show various views of one non-limiting embodiment of the trigger member E shown in FIG. 9 and illustrate the various features thereof. The Trigger E minimizes flow through the device and receptacle Q until a minimum threshold vacuum is achieved. The trigger E opens suddenly providing a rapid pulse of air through the receptacle Q and device to aid in receptacle Q evacuation and powder deagglomeration. A star-shaped opening of the tr receptacle Q. Upon each actuation of the device, the deoccluding member G is rotated 180° relative to the feed tube FT to prevent clogging of the drug path. The wings of the deoccluding member G engage features in the cutter mechanism H and prevent the deoccluding member G from coming completely free.

Figure 51:
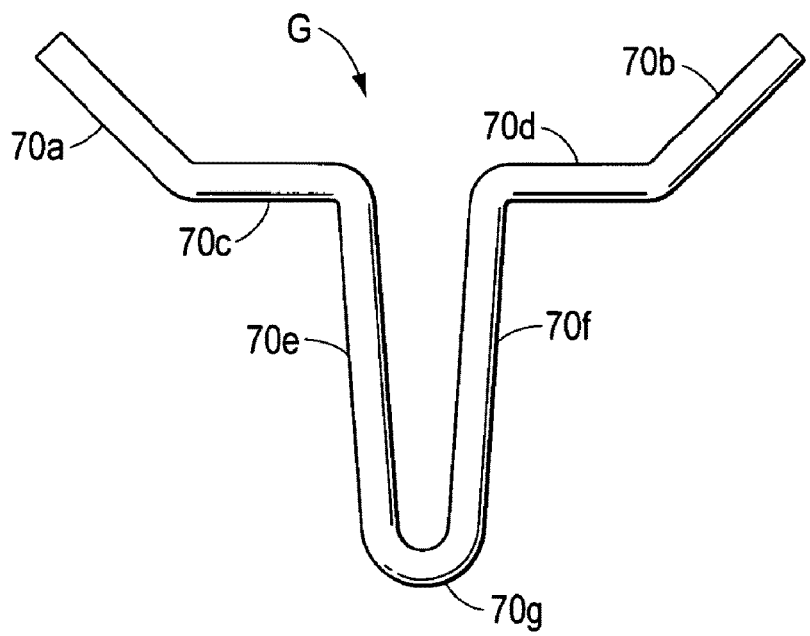
FIG. 51 shows a front side view of the deoccluding member shown in FIG. 9.
Figure 52:
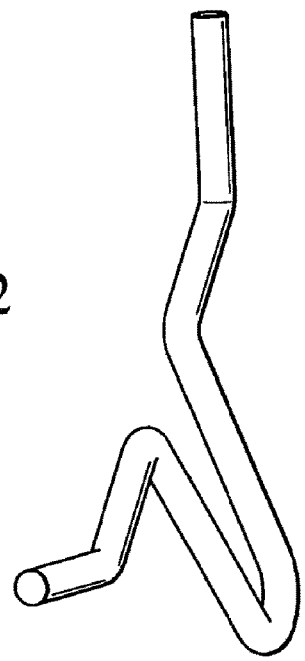
FIG. 52 shows a top left side view of the deoccluding member shown in FIG. 51.
Figure 53:
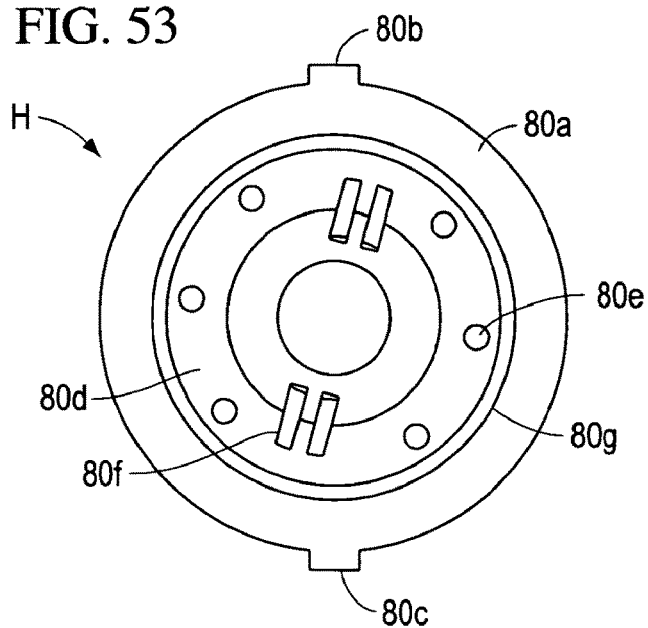
FIG. 53 shows a top view of the cutter mechanism shown in FIG. 9.
Figure 54:
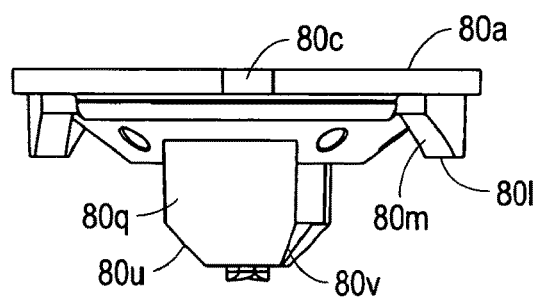
FIG. 54 shows a front side view of the cutter mechanism shown in FIG. 53.
Figure 55:
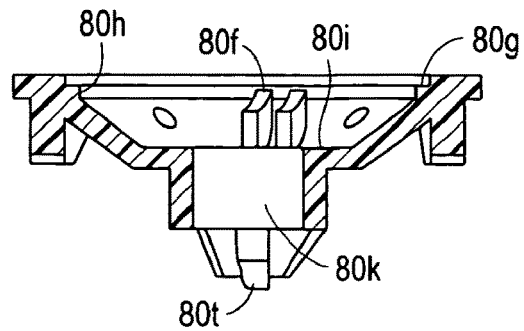
FIG. 55 shows a front side cross-section view of the cutter mechanism shown in FIG. 53.
Figure 60:
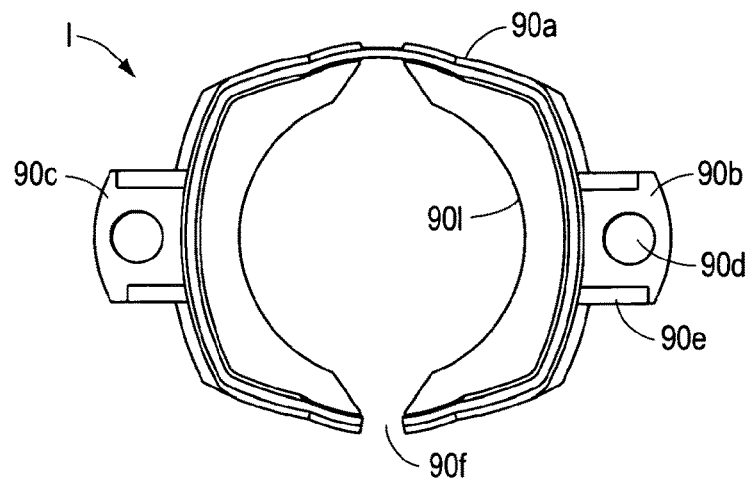
FIG. 60 shows a top view of the upper bearing member shown in FIG. 9.
Figure 61:
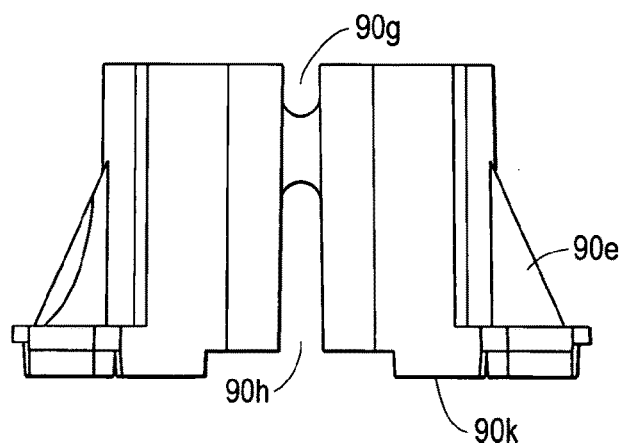
FIG. 61 shows a front side view of the upper bearing member shown in FIG. 60.
Figure 62:
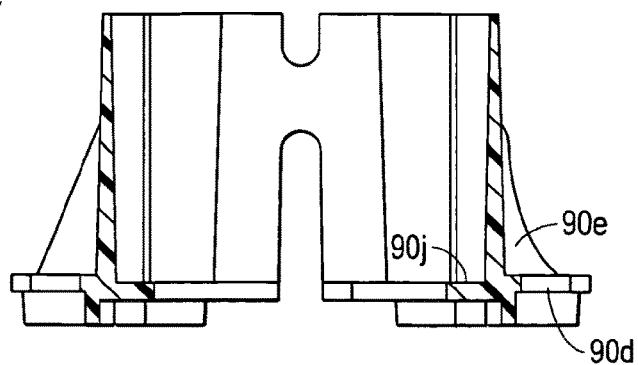
FIG. 62 shows a front side cross-section view of the upper bearing member shown in FIG. 60.
Figure 63:
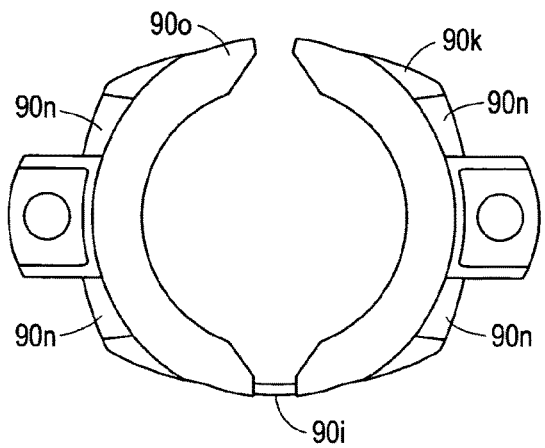
FIG. 63 shows a bottom view of the upper bearing member shown in FIG. 60.
Figure 64:
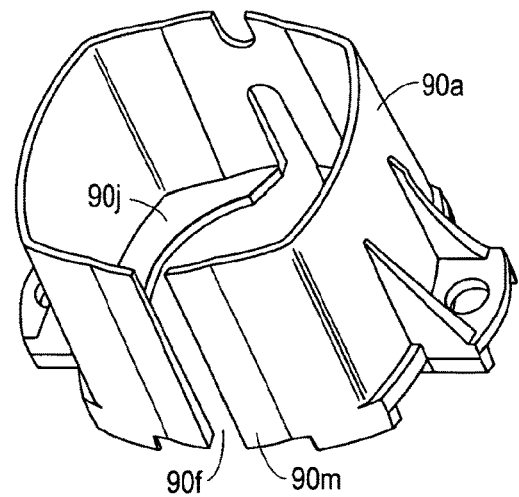
FIG. 64 shows a top right front perspective view of the upper bearing member shown in FIG. 60.
Figure 65:
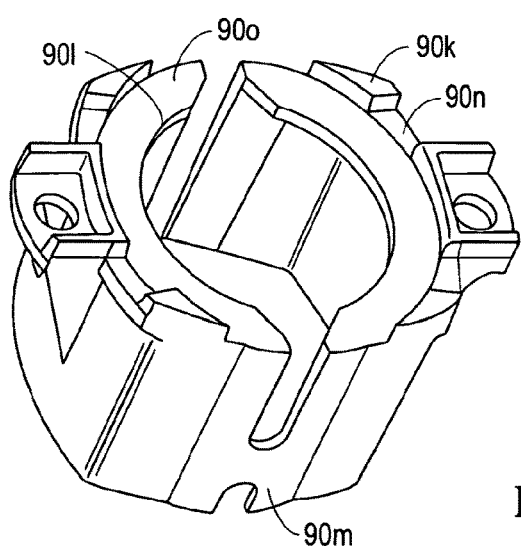
FIG. 65 shows a bottom rear side perspective view of the upper bearing member shown in FIG. 60.
Figure 66:
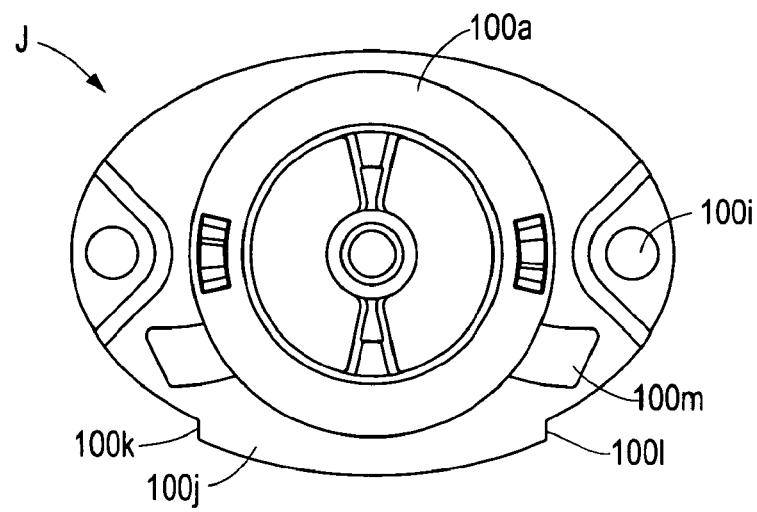
FIG. 66 shows a top view of the lower bearing member shown in FIG. 9.
Figure 67:
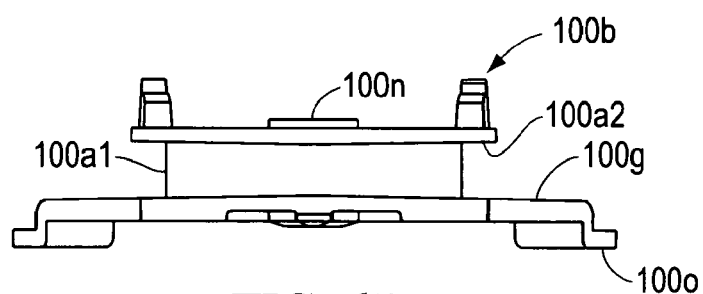
FIG. 67 shows a front side view of the lower bearing member shown in FIG. 66.
Figure 68:
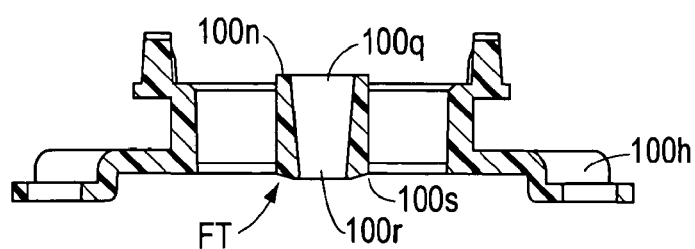
FIG. 68 shows a front side cross-section view of the lower bearing member shown in FIG. 66.
Figure 73:
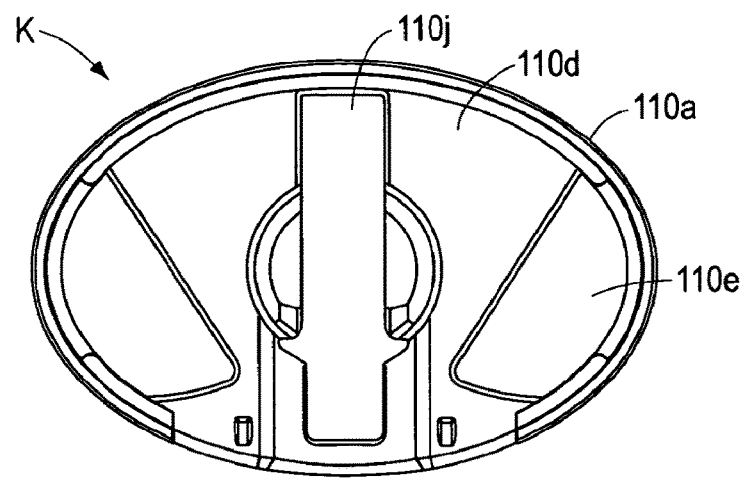
FIG. 73 shows a top view of the body member shown in FIG. 9.
Figure 74:
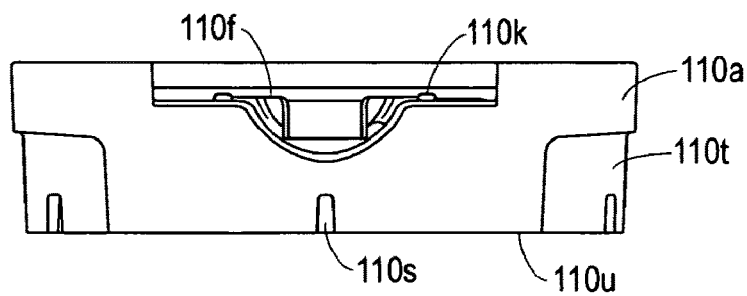
FIG. 74 shows a front side view of the body member shown in FIG. 73.
Figure 75:
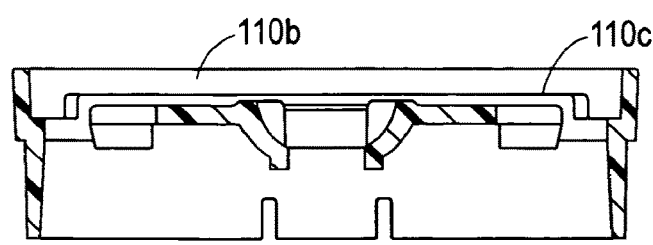
FIG. 75 shows a front side cross-section view of the body member shown in FIG. 73.
Figure 76:
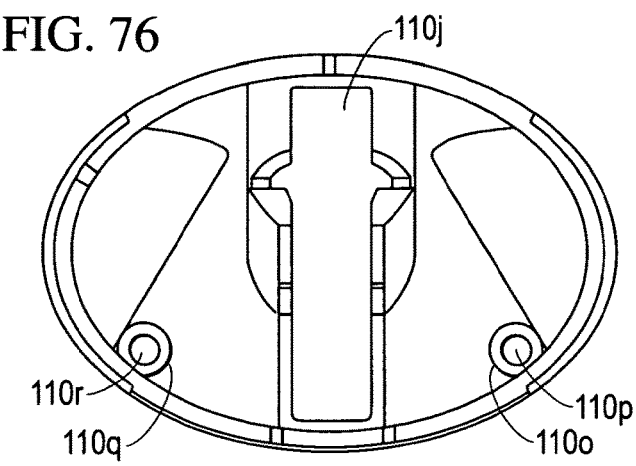
FIG. 76 shows a bottom view of the body member shown in FIG. 73.
Figure 77:
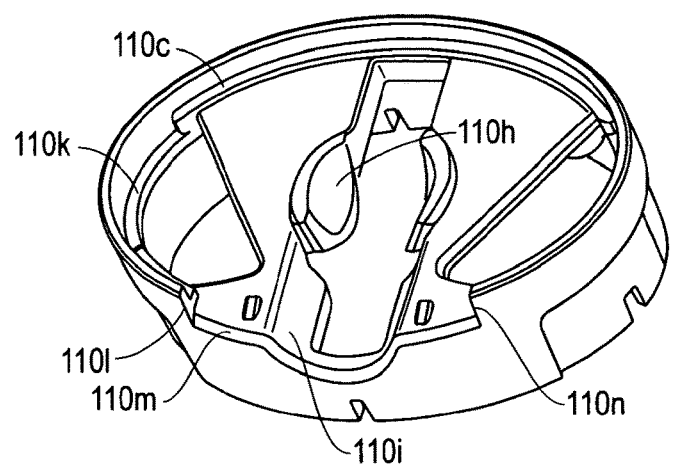
FIG. 77 shows a top right front perspective view of the body member shown in FIG. 73.
Figure 78:
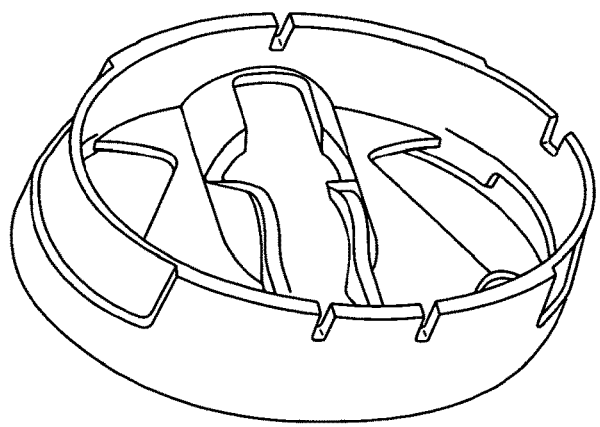
FIG. 78 shows a bottom rear side perspective view of the body member shown in FIG. 73.
Figure 79:
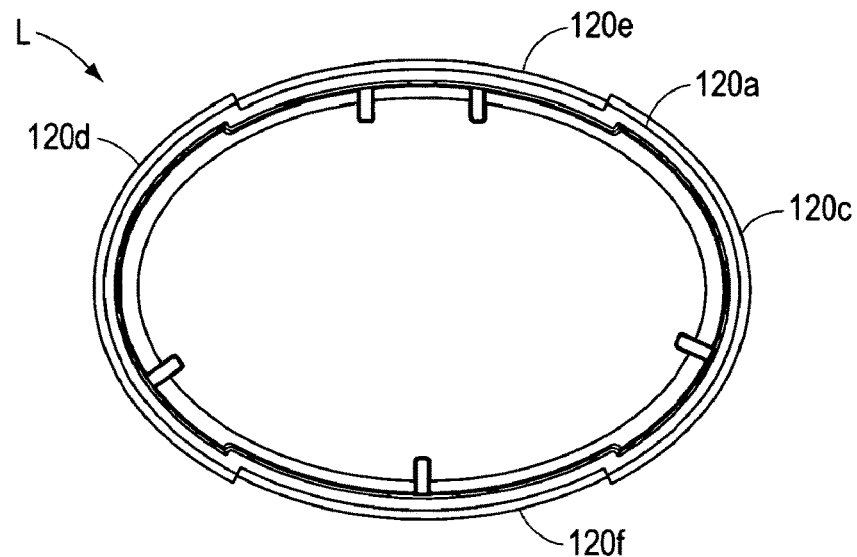
FIG. 79 shows a top view of the skirt shown in FIG. 9.
Figure 80:
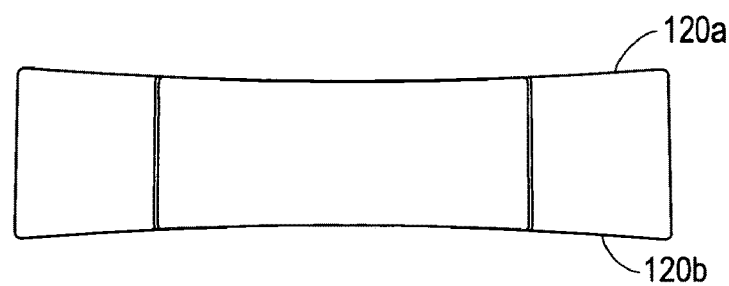
FIG. 80 shows a front side view of the skirt shown in FIG. 79.
Figure 81:
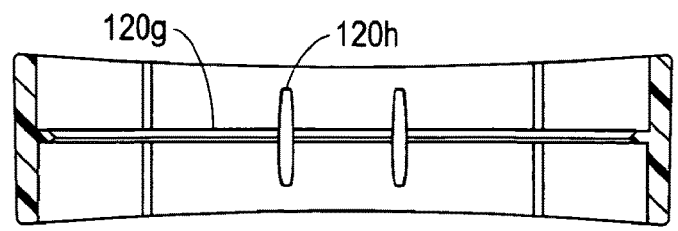
FIG. 81 shows a front side cross-section view of the skirt shown in FIG. 79.
Figure 82:
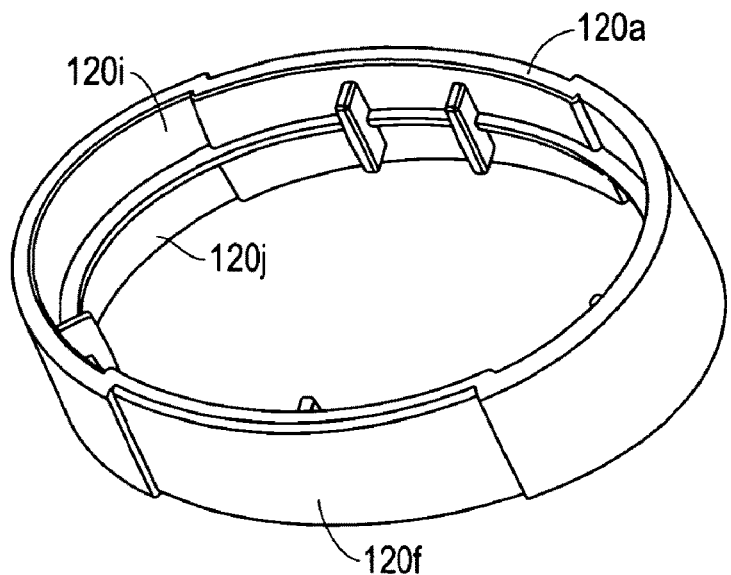
FIG. 82 shows a top right front perspective view of the skirt shown in FIG. 79.
Figure 83:
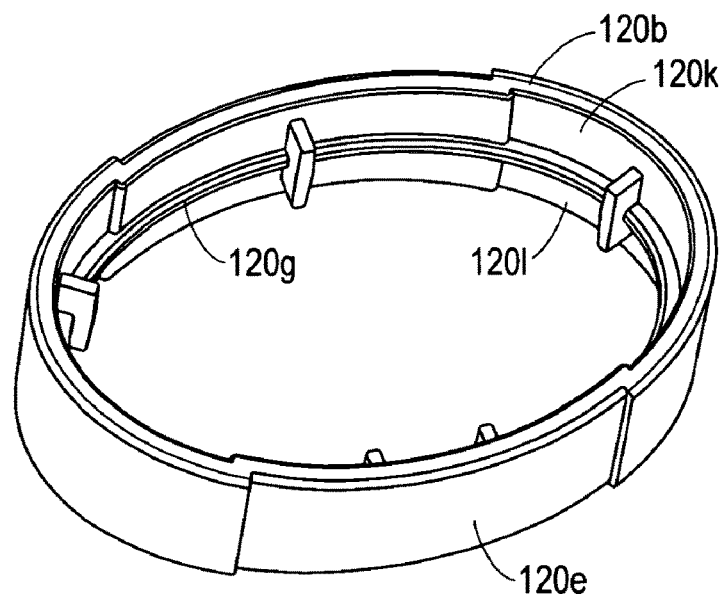
FIG. 83 shows a bottom rear side perspective view of the skirt shown in FIG. 79.
Figure 84:
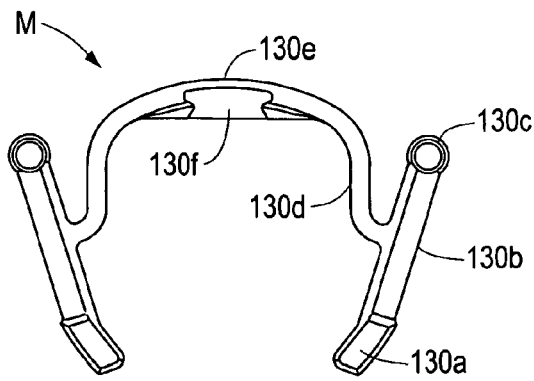
FIG. 84 shows a top view of the lock member shown in FIG. 9.
Figure 85:
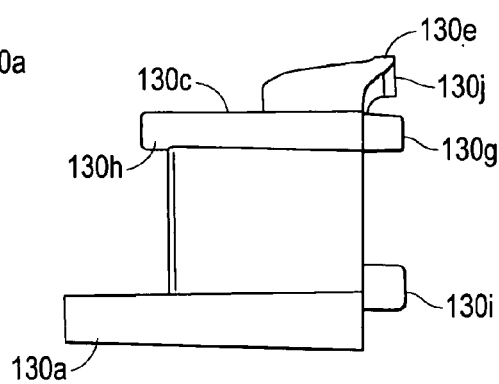
FIG. 85 shows a right side view of the lock member shown in FIG. 84.
Figure 86:
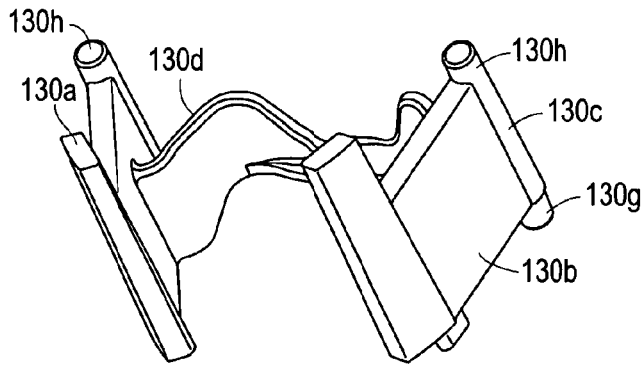
FIG. 86 shows a top right front perspective view of the lock member shown in FIG. 84.
Figure 87:
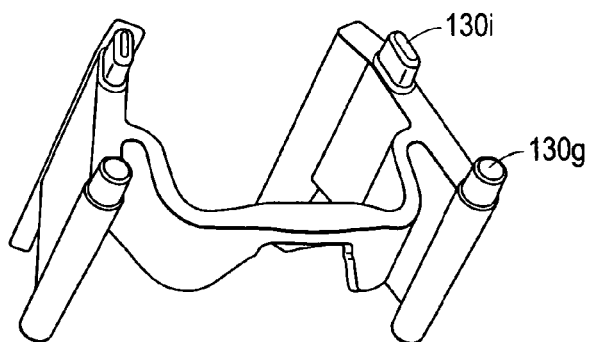
FIG. 87 shows a bottom rear side perspective view of the lock member shown in FIG. 84.
Figure 88:
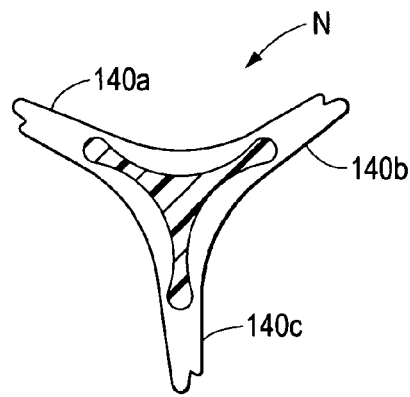
FIG. 88 shows a right side partial cross-section view of the receptacle impacting member shown in FIG. 9.
Figure 89:
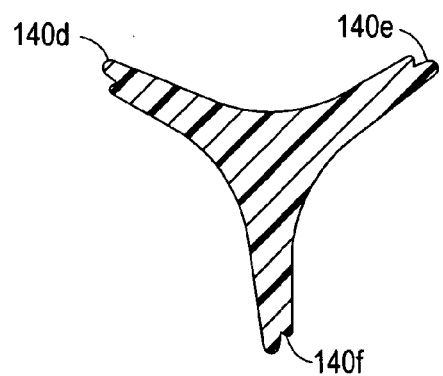
FIG. 89 shows a right side cross-section view of the receptacle impacting member shown in FIG. 88.
Figure 90:
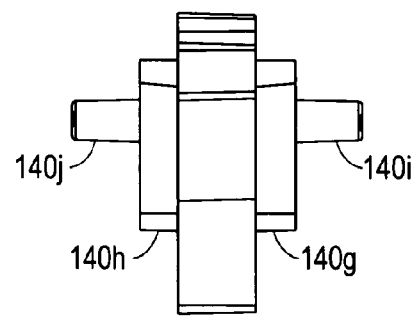
FIG. 90 shows a front side view of the receptacle impacting member shown in FIG. 88.
Figure 91:
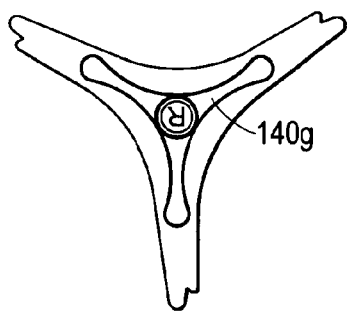
FIG. 91 shows a right side view of the receptacle impacting member shown in FIG. 88.
Figure 92:
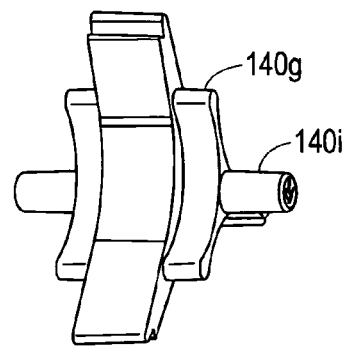
FIG. 92 shows a right front perspective view of the receptacle impacting member shown in FIG. 88.

As is shown in FIGS. 51-52, the deoccluding member G has the form of a bent wire configuration and includes upper free ends 70*a* and 70*b* and a lower rounded puncturing end 70*g*. The upper free ends 70*a* and 70*b* and the connecting portions 70*c* and 70*d* are sized and configured to seat within the oppositely arranged pairs of projections 80*f* of the cutter mechanism H (see FIG. 10). The lower rounded puncturing end 70*g* is sized and configured to puncture and tear open the exit opening of the receptacle Q (see FIG. 102). The deoccluding member G also has two generally vertical deoccluding portions 70*e* and 70*f* which are sized and configured to either ride just above or scrape against the inner surface of the feed tube FT (see FIG. 68). The two generally vertical deoccluding portions 70*e* and 70*f* can preferably be angled to correspond to the tapered surface of the feed tube FT. This ensures that the deoccluding member G will be able to clean the feed tube FT each time that the deoccluding member G is rotated 180 degrees. Of course, other configurations and shapes for the deoccluding member G are contemplated. For example, the deoccluding member G can also be integrally formed with one of the other components of the apparatus such as, e.g., the cutter mechanism H or the orifice member F. Additionally, the deoccluding member G can be made of the materials described above and can even be made transparent or translucent.

FIGS. 53-59 show various views of one non-limiting embodiment of the cutter mechanism member H shown in FIG. 9, and illustrate the various features thereof. Teeth 80*t* of the cutter mechanism H create inlet holes in the lidstock of the receptacle Q. Holes 80*e* allow bypass air to enter the aerosol module D-H to keep the overall resistance of the device at a desired level. Four radial ribs 80*f* locate and constrain the deoccluding device G. The orifice member F and the cutter mechanism H together form a flange to transmit the force of the compression spring C to the aerosol module D-H. Cams 80*m*, 80*n* on the underside of the cutter mechanism H engage cams 100*c*, 100*d*, 100*f* on the body member J to lower and retract the aerosol module D-H. Wedge-shaped recesses on the outer cams 80*o*, 80*p* provide a detent for the home position of the mouthpiece B rotation and discourage reverse rotation from the home position. Central bore 80*k* of the cutter mechanism H creates a telescoping and rotating seal to the feed tube FT.

As is shown in FIGS. 53-59, the cutter mechanism H has a generally circular configuration and includes an open upper end 80*a* having two oppositely arranged projections 80*b* and 80*c*. Projection 80*b* is sized and configured to fit within and slide up in either slot 90*h* or slot 90*f* of the upper bearing member I. Projection 80*c* is sized and configured to fit within and slide up in the other of either slot 90*h* or slot 90*f* of the upper bearing member I. The cutter mechanism H also has a generally circular opening 80*k* which is sized and configured to receive therein in a sealingly manner the upper end of the feet tube FT. The engagement between the generally circular opening 80*k* and the upper end of the feed tube FT utilizes a very small to essentially zero clearance, acts to center the cutter mechanism H in the apparatus and thereby determine the proper position of the teeth 80*t* to precisely form the two arc-shaped inlet openings in the receptacle Q, and also serves as the mounting (or bushing and/or bearing) that allows the cutter mechanism H to rotate and move axially relative to the feed tube FT. The rotational movement is, of course, caused by rotation of the mouthpiece B while the axial movement of the cutter mechanism H is determined by the relative position of the surfaces 80*l* of relative to surface 100*a* of member J. Rotational contact between the surfaces 80*l* and surface 100*a* occurs during the tearing of the inlet openings in receptacle Q and contact between the surfaces 80*l* and surfaces of members 100*b*, i.e., the generally horizontal surfaces between surfaces 100*c* and 100*d* and between 100*e* and 100*f*, occurs when the mouthpiece B is in one of the two 180 degree activation-ready positions. Thus, contact between the surfaces 80*l* and surface 100*a* means that the teeth 80*t* are in the fully extended position (i.e., penetrating into the lidstock of receptacle Q) and contact between the surfaces 80*l* and the generally horizontal surfaces of members 100*b* means the teeth 80*t* are in a retracted position. The spring C biases the cutter mechanism H towards the member J and thus functions to cause the axial movement of the cutter mechanism H towards the member J. The cutter mechanism H also has oppositely arranged notches each defined by a generally vertical surface 80*o* and an angled surface 80*p* whose design is such as to only permit rotation of the cutter mechanism H in the clockwise direction. These surfaces correspond to surfaces 100*c* and 100*d* of member J which together ensure that rotation of the cutter mechanism H is only allowed in the clockwise direction. The cutter mechanism H also utilizes two oppositely arranged pairs of projections 80*f* which receive the free ends of the deoccluding device G as described above. The cutter mechanism H further also utilizes two oppositely arranged angled cam surfaces 80*m* which are configured to engage surfaces 100*c* and 100*d* of the member J and, when so engaged, causes axial movement of the cutter mechanism H away from the receptacle Q. Two other oppositely arranged angled cam surfaces 80*n* are configured to engage surfaces 100*f* of the member J and, when so engaged, allow axial movement of the cutter mechanism H towards the receptacle Q under the biasing force of the spring C. Angled surfaces 80*u* allow the cutter mechanism H to avoid contacting portions 100*t* of the member J when the cutter mechanism H is rotating. Surfaces 80*r* are configured to contact portions 100*t* of the member J when the cutter mechanism H is in the two 180 degree pre-activated positions. A plurality of equally sized, e.g., six, through openings 80*e* are arranged on angled wall 80*d* and allow bypass airflow to pass through the cutter mechanism H and then through the orifice opening 60*j*. Each of the two teeth 80*t* is arranged on a tooth support 80*s* sized and configured to prevent deflection of the teeth 80*t* during cutting or tearing. Of course, other configurations and shapes for the cutter mechanism H are contemplated. Additionally, the cutter mechanism H can be made of the materials described above and can even be made transparent or translucent.

Considerations for the design and configuration of the cutter mechanism H and member J, and certain aspects thereof, can include the following: although the feed tube FT has a tapered configuration, i.e., having an inlet bottom end which is smaller than an outlet upper end and a tapered opening extending therebetween. The angle of taper is typically less than 5°. Other configurations are possible including an opening which is substantially cylindrical, i.e., an angle of taper of 0°. Considerations in the design of the feet tube FT should include a concern for maintaining an accelerating air flow up through the feed tube FT; and ensuring that the opening shape or configuration minimized or avoids boundary layer separation. Some deceleration flow can occur in the feed tube FT, however. The cutter mechanism H can be designed so that the center outlet opening in the lidstock is formed either prior to the two arc-shaped inlet openings or simultaneously therewith (see e.g., FIG. 102). In this regard, once the member G is assembled to the cutter mechanism H, the end 70g can be arranged to have the same axial distance as the end of the teeth 80t. Alternatively, when the member G is assembled to the cutter mechanism H, the end 70g can instead be arranged to have a smaller axial distance than the end of the teeth 80t so that the teeth 80t puncture the lidstock before the end 70g when the cutter mechanism H is moved towards the lidstock of the receptacle Q. The lower end (or inlet end) of the feed tube FT is also preferably in contact with the lidstock during puncturing of the openings and/or when the user activates the trigger E by inhalation. This contact provides a temporary seal and ensures that nearly all of the air/powder flow out of the receptacle Q is directed up through the feed tube FT. A perfect seal in this area is not necessary, however. Acceptable sealing contact can include, among other things, contact which is sufficient to place the lidstock of the receptacle Q in tension.

FIGS. 60-65 show various views of one non-limiting embodiment of the upper bearing member I shown in FIG. 9, and illustrate the various features thereof. The upper bearing member I provides surfaces for ultrasonically welding to the mouthpiece B. Vertical channels on the upper bearing member I engage tabs on the cutter mechanism H to synchronize the rotation of the aerosol module D-H with the rotation of the mouthpiece B.

As is shown in FIGS. 60-65, the upper bearing member I has a generally square configuration and includes open upper and lower ends and two oppositely arranged projecting portions 90b and 90c. Projections 90b and 90c are sized and configured to fit within recesses 20r of mouthpiece B. Projections 90b and 90c each utilize two support flanges 90e arranged on oppositely arranged walls 90a and an opening 90d sized to receive therein the projections 20h of mouthpiece B. The upper bearing member I also has two oppositely arranged projecting wall portions 90m. One of these projecting wall portions 90m includes slot 90f and the other of the projecting wall portions 90m includes upper slot 90g and lower slot 90h. As explained above, the upper portion of slot 90f is sized and configured to receive therein the pair of ribs 20p of the mouthpiece B while the upper slot 90g is sized and configured to receive therein the oppositely arranged pair of ribs 20p of the mouthpiece B. Additionally, the lower portion of slot 90f is sized and configured to slidingly receive therein the projection 80c of the cutter mechanism H while the lower slot 90h is sized and configured to slidingly receive therein the oppositely arranged projection 80b of the cutter mechanism H. The upper bearing member I also has a generally circular opening 90l which is sized and configured to rotatably engage circumferential surface 100a1 of the member J. When the upper bearing member I is installed on member J, the bottom surface 90k of upper bearing member I is configured to frictionally engage with upper surface 100j of member J while the upper surface 90j of upper bearing member I frictionally engages with lower surface 100a2 of member J. Such contact functions to create two bearings and ensures that the upper bearing member I can rotate relative to the member J while also ensuring that the upper bearing member I does not move substantially axially relative to the member J. Furthermore, because the upper bearing member I becomes fixed to the mouthpiece B and because the member J becomes fixed to the lower housing P, these engaging surfaces provide the rotatable and not separable connection between the upper portion of the apparatus formed by parts B-I and the lower portion of the apparatus formed by parts J-P. The upper bearing member I also functions as part of the receptacle lock system described above. In this regard, the upper bearing member I includes four recesses 90n which are sized and configured to receive therein ends 130a of the locking member M when the ends 130a are moved to the locking position. When the locking member M is not in the locking position, the free ends 130a do not extend into recesses 90n and instead remain underneath surface 90o. Of course, other configurations and shapes for the upper bearing member I are contemplated. Additionally, the upper bearing member I can be made of the materials described above and can even be made transparent or translucent.

FIGS. 66-72 show various views of one non-limiting embodiment of the lower bearing member J shown in FIG. 9, and illustrate the various features thereof. A circular flange 100a1 at the top of the lower bearing member J constrains the flange 90l of the upper bearing member I to hold the upper half and lower half of the device together. The feed tube FT provides a conduit for aerosol to exit receptacle Q and enter the aerosol module D-H. The feed tube FT provides a rotating and telescoping seal to the aerosol module D-H. Cams 100c, 100d, 100f on the circular flange 100a1 of the lower bearing member J engage cams 80m, 80n on the underside of the cutter mechanism H to raise and lower the aerosol module D-H. Wedge-shaped teeth 100d on the outer cams provide a detent for the home position of the mouthpiece B rotation and discourage reverse rotation from the home position. Arc-shaped holes 100m on the top of the lower bearing member J provide clearance for the projections 130a of lock member M.

As is shown in FIGS. 66-72, the member J has a generally oval configuration and includes an upper end 100a having two oppositely arranged projections 100b. Projections 100b function to control the axial position of the cutter mechanism H as the cutter mechanism H rotates to ensure that the cutter mechanism H can only rotate clockwise (as was described above). As was explained above, the surface 100a2 forms an upper bearing with surface 90j and the surface 100g forms a lower bearing with surface 90k. Furthermore, the surface 100a1 forms a bearing with surface 90l. The former upper and lower bearings ensure that upper bearing member I is axially retained while the latter bearing ensures that the upper bearing member I remains coaxial with the feed tube FT. The member J also utilizes oppositely arranged lower flange portions 100o which are sized and configured to seat within oppositely arranged support shoulders 110k of member K. The lower flange portions 100o each include a through opening 100i sized and configured to receive therein one of the free ends of projections 160c of member P. The member J also utilizes a front facing main projection 100j which includes sides 100k and 100l that are sized and configured to seat within a main front recess of member K defined by surfaces 110m, 110l and 110n of member K. Member J also utilizes two guide slots 100m which allow the free ends 130a of the locking member M to pass therethrough and limit the movement of the ends 130a between the locked position and the unlocked position. As explained above, a feed tube FT is arranged on the member J and functions to direct and/or convey the aerosolized airflow from the outlet opening formed in the receptacle Q up through the apparatus before passing through the central opening of the orifice member F. In this regard, the feed tube FT includes lower tapered surface 100s which is configured to sealingly engage and/or contact the lidstock of the receptacle Q when the receptacle Q is installed in the apparatus. The feed tube FT utilizes a through opening having a larger upper end 100$q$ and a smaller lower end 100$r$ and is generally tapered and is connected to the member J via two oppositely arranged spoke-like members each having an enlarged portion 100$t$ and a smaller portion 100$u$. The two open areas defined by the inner cylindrical surface of the wall 100$a$1 and the two oppositely arranged spoke-like members each having an enlarged portion 100$t$ and a smaller portion 100$u$ allow for bypass air to flow up through the member J and also serves a storage area for inlet air which will flow into the inlet openings formed in the lidstock of the receptacle Q. The member J also has a centrally disposed tapered inlet guide surface 100$x$ which extends across the main projection 100$j$. This allows the receptacle Q to be inserted more easily and properly. Once the leading end of the receptacle Q passes the tapered surface 100$x$, the upper surface of the leading end of the receptacle Q is guided by surface 100$w$ and then by surface 100$z$ until the receptacle Q is fully positioned. Two shallow recesses 100$v$ are arranged on opposite sides of the guide surfaces 100$w$, 100$y$, and 100$z$ and function to, among other things, reduce the frictional contact with the receptacle Q. Of course, other configurations and shapes for the member J are contemplated. Additionally, the member J can be made of the materials described above and can even be made transparent or translucent.

FIGS. 73-78 show various views of one non-limiting embodiment of the support body member K shown in FIG. 9, and illustrate the various features thereof. A central rectangular opening 110$j$ provides clearance for the receptacle impacting member N.

As is shown in FIGS. 73-78, the member K has a generally oval configuration and includes an upper support surface 110$d$ having a main generally rectangular opening 110$j$ and two outer openings 110$e$. The opening 110$j$ functions to, among other things, allow ends 140$a$-140$c$ of the receptacle impacting member N to pass therethrough and allow the member N to rotate upon insertion of the receptacle Q. The openings 110$e$ function to, among other things, allow the ends 130$a$ of the lock member M to pass therethrough and to move upon insertion of the receptacle Q. Two ramp-shaped support projections 110$k$ are arranged on the surface 110$d$ and function to lift slightly the receptacle Q during its insertion. A main generally spherical recess 110$h$ is located in a central area of the member K and functions to correctly position and support the tub portion of the receptacle Q. A generally curved recess 110$i$ extends from the recess 110$h$ to an entrance area of the member K and functions to allow the tub portion of the receptacle Q to pass into the apparatus. The entrance area is defined by a recess which includes oppositely arranged side edges 110$l$ and 110$n$ and bottom edge 110$m$. The two oppositely arranged side edges 110$l$ and 110$n$ are spaced to receive therein the projecting portion 100$j$ of member J and are configured to abut edges 100$k$ and 100$l$. Two arc-shaped support surfaces 110$f$ are arranged above the spherical recess 110$h$ and function to support the bottom side surface of the receptacle Q while the recess 110$h$ supports the tub portion of the receptacle Q. Additionally, two oppositely arc-shaped support shoulders 110$k$ are arranged to support the oppositely arranged projecting portions 100$o$ of member J. The front and back arc-shaped support shoulders 110$c$ are arranged to support the peripheral portion of the outer surface 100$p$ of member J. The member K also utilizes slots 110$s$ which are sized and configured to receive upper portions of projections 120$h$ of member L. The member K additionally also utilizes two oppositely arranged indentations 110$t$ which function to allow air to enter into the apparatus. When the members K and L are assembled together, a small space remains between bottom edge 110$u$ and shoulder 120$g$ and a larger space between indentations 110$t$ and the indentations 120$i$. Member K also utilizes two bottom facing projections 110$q$ and 110$o$ which have circular recesses 110$r$ and 110$p$ that form bearings for the two ends 130$h$ of lock member M. Of course, other configurations and shapes for the member K are contemplated. Additionally, the member K can be made of the materials described above and can even be made transparent or translucent.

FIGS. 79-83 show various views of one non-limiting embodiment of the skirt member L shown in FIG. 9, and illustrate the various features thereof. The skirt member L provides tamper resistance by covering the holes in the body J required to snap the lower half subassembly together. The skirt member L may provide trade dress. The skirt member L may provide a location for the patient to write on the device, e.g., the date of first use.

As is shown in FIGS. 79-83, the member L has a generally oval configuration and includes an upper edge 120$a$ having a generally inwardly curved front and rear edges and generally outwardly curved left and right sides edges. The member L also includes a lower edge 120$b$ having a generally inwardly curved front and rear edges and generally outwardly curved left and right sides edges. Two oppositely arranged indentations 120$i$ are on inner portions of the left and right sides of the member L and function to allow air to enter into the apparatus. The member L also utilizes projections 120$h$ whose upper ends are sized and configured to engage slots 110$s$ of the member K and whose lower ends are sized and configured to engage slots 160$d$ of the member P. The member L additionally also utilizes an inwardly facing peripheral shoulder 120$g$. When the members L and P are assembled together, there remains a small space between the upper edge 160$b$ and shoulder 120$g$ and a larger space between indentations 120$j$ and the indentations 160$g$. Member L also utilizes two front and back oppositely arranged indentations 120$e$ and 120$f$. Of course, other configurations and shapes for the member L are contemplated. Additionally, the member L can be made of the materials described above and can even be made transparent or translucent.

FIGS. 84-87 show various views of one non-limiting embodiment of the lock member M shown in FIG. 9, and illustrate the various features thereof. Ends 130$a$ are biased inwards to follow the profile of the receptacle Q during insertion. If the receptacle Q is not fully inserted, the ends 130$a$ engage details on the underside of the upper bearing member I that prevent rotation of the mouthpiece B. The ends 130$a$ are biased inwards and engage side notches 170$g$ in the receptacle Q outline to pull the receptacle Q into the device. Once the mouthpiece B is rotated, ends 130$a$ prevent receptacle Q insertion or removal until the mouthpiece B is returned to the home position. Ends 130$a$ prevent the receptacle Q from being inserted backwards. The ends 130$a$ discourage the use of non-mating receptacles in the device.

As is shown in FIGS. 84-87, the lock member M has a main connecting portion 130$e$ having a reinforcing shoulder 130$f$ and connecting together, via two flexible connecting web portions 130$d$, two plate-like members 130$b$. Each web portion 130$d$ functions as a spring so that when the plate members 130$b$ are rotated about the axes of the members 130$c$ (as will typically occur upon insertion of the receptacle Q into the apparatus), the web portions 130$d$ are stressed and function to bias the members 130*b* towards the original non-stressed state shown in FIGS. 135-142. The lock member M also includes upper bearing shaft portions 130*h* which are sized and spaced to engage recesses 110*r* and 110*p* of member K and lower bearing shaft portions 130*g* which are sized and spaced to engage recesses 160*l* and 160*j* of member P. A bottom surface 130*j* of the member M and two optional bottom projections 130*i* function to vertically support the member M within the member P. The member M also utilizes projections 130*a* whose upper ends are spaced apart to receive the leading end of the receptacle Q and which can be moved apart thereby during insertion of the receptacle Q. These ends 130*a* are also configured to seat within oppositely arranged recesses 170*g* of the receptacle Q. The lock member M can also utilize a single end portion 130*a* and/or a single plate-like member 130*b* since only one of these is required to cause a locking of the apparatus. Of course, other configurations and shapes for the member M are contemplated. Additionally, the member M can be made of the materials described above and can even be made transparent or translucent.

FIGS. 88-92 show various views of one non-limiting embodiment of the receptacle impacting member N shown in FIG. 9, and illustrate the various features thereof. Upon insertion of the receptacle Q into the device, the receptacle impacting member N provides an impact to the receptacle tub 170*h* to help break up powder. The insertion of the receptacle Q drives the mechanism due to the recesses 140*e* on the end of each arm 140*a*, 140*b*, 140*c* of the receptacle impacting member N.

As is shown in FIGS. 88-92, the member N has a generally triangular configuration and includes a main portion having three generally identical arms 140*a*-140*c* extending therefrom. The axial end surfaces of the portions 140*h* and 140*g* are sized and configured to movably engage with inner facing surfaces of plate-like projections 160*e* of member P. The plate-like projections 160*e* of member P also function to limit axial movement of the member N and ensure that the arms 140*a*-140*c* move freely within the recess 110*j*. The member N is designed to rotate and move up and down when mounted to the member P. In this regard, the member N includes two oppositely arranged axial projections 140*i* and 140*j* which are sized and configured to rotate and move vertically between the slots formed between the projections 160*f* and 160*e*. Each arm 140*a*-140*c* includes an upper lip portion 140*d* and a recess 140*e* which is designed to receive the leading end of the receptacle Q. Upon insertion of the receptacle Q into the apparatus, the leading end of the receptacle Q with slide beneath the upper lip 140*d* and engage the shoulder 140*f* of recess 140*e*, and further insertion movement of the receptacle Q will cause the member N to rotate about the axis of the projections 140*i* and 140*j*. Such rotation also causes the member N to move downwards between the slots formed between the projections 160*f* and 160*e*. This downward movement is resisted by the free ends 150*a* and 150*b* of the torsion spring O which causes the member N to back upwards as the receptacle Q is moved to a final insertion position in the apparatus. Of course, other configurations and shapes for the member N are contemplated. Additionally, the member N can be made of the materials described above and can even be made transparent or translucent.

Figure 93:
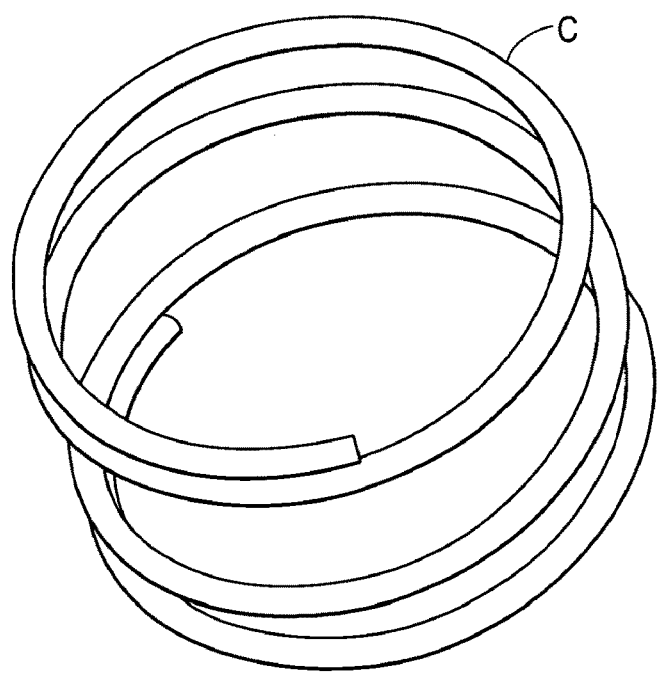
FIG. 93 show a top right front perspective view of the coil spring shown in FIG. 9.

FIG. 93 shows a view of one non-limiting embodiment of the coil spring C shown in FIG. 9, and illustrates the various features thereof. The coil spring C provides a downward bias to aerosol module D-H causing cams 80*m*, 80*n* of cutter member H and surfaces 100*c*, 100*d*, and 100*f* of body member J to determine the vertical position of aerosol module D-H as a function of mouthpiece B rotation.

As is shown in FIG. 93, the spring C has a generally circular configuration and is sized and configured to engage the projections 20*i* of the member B and the surface 80*a* of member H. The spring C thus functions to bias the cutter mechanism H towards member J. By way of non-limiting example, the spring C can be of a configuration which sets the actuation torque (the torque required to rotate the mouthpiece B and actuate the apparatus) within the range of between about 0.3 Nm and about 0.5 Nm, and is preferably set to about 0.33 Nm. By way of non-limiting example, the spring C can be made of stainless steel and can have a grade of 302/304. Of course, other configurations and shapes for the spring C are contemplated.

FIG. 94 shows a non-limiting embodiment of the torsion spring O shown in FIG. 9, and illustrate the various features thereof. As is shown in FIG. 94, the spring O has a generally rectangular base portion formed by two straight generally parallel side sections 150*d* and a connecting portion 150*e*. This base portion is designed to rest on a bottom inner surface of member P. The spring O also utilizes two free end portions 150*a* and 150*b* which are sized and configured to slide between the plate-like projections 160*e* and 160*f* of member P (see, e.g., FIG. 18). These free ends 150*a* and 150*b* are configured to be engaged by the two oppositely arranged axial projections 140*i* and 140*j* of receptacle impacting member N (see, e.g., FIG. 19). Each free end 150*a* and 150*b* is connected to the base portion via a connecting coil portion 150*c*. The coil portion 150*c* functions as a torsion spring and resists the downward movement of the free ends 150*a* and 150*b*. By way of non-limiting example, the spring O can be made of stainless steel and can have a grade of 302/304. Of course, other configurations and shapes for the spring O are contemplated. Furthermore, it is also possible to make the spring O of synthetic resin. The spring O can also have the form of a plate instead of being a wire torsion spring.

FIGS. 95-98 show various views of one non-limiting embodiment of the body member P shown in FIG. 9, and illustrate the various features thereof. The body member P provides a flat surface on the bottom of the device for labeling.

As is shown in FIGS. 95-98, the member P has a generally oval configuration and includes an upper edge 160*b* and a plurality of slots 160*d* which are sized and configured to receive the lower portions of projections 120*h* of member L. Four plate-like projections 160*f* and 160*e* are arranged vertically and function to guide the movement of the spring O as well as the receptacle impacting member N (as was described above). Two cross-shaped projections 160*c* are arranged vertically, and the free ends of these projections 160*c* are structured and arranged to become fixed or non-removably connected to the portions 100*o* of member J. The member P additionally also utilizes two oppositely arranged indentations 160*g* which function to allow air to enter into the apparatus. When the members P and L are assembled together, there remains a small space between upper edge 160*b* and shoulder 120*g* and a larger space between indentations 160*g* and the indentations 120*j*. Member P also utilizes two upward facing projections 160*k* and 160*i* which have circular recesses 160*l* and 160*j* that form bearings for the two ends 130*g* of lock member M. Of course, other configurations and shapes for the member P are contemplated. Additionally, the member P can be made of the materials described above and can even be made transparent or translucent.

Figure 100:
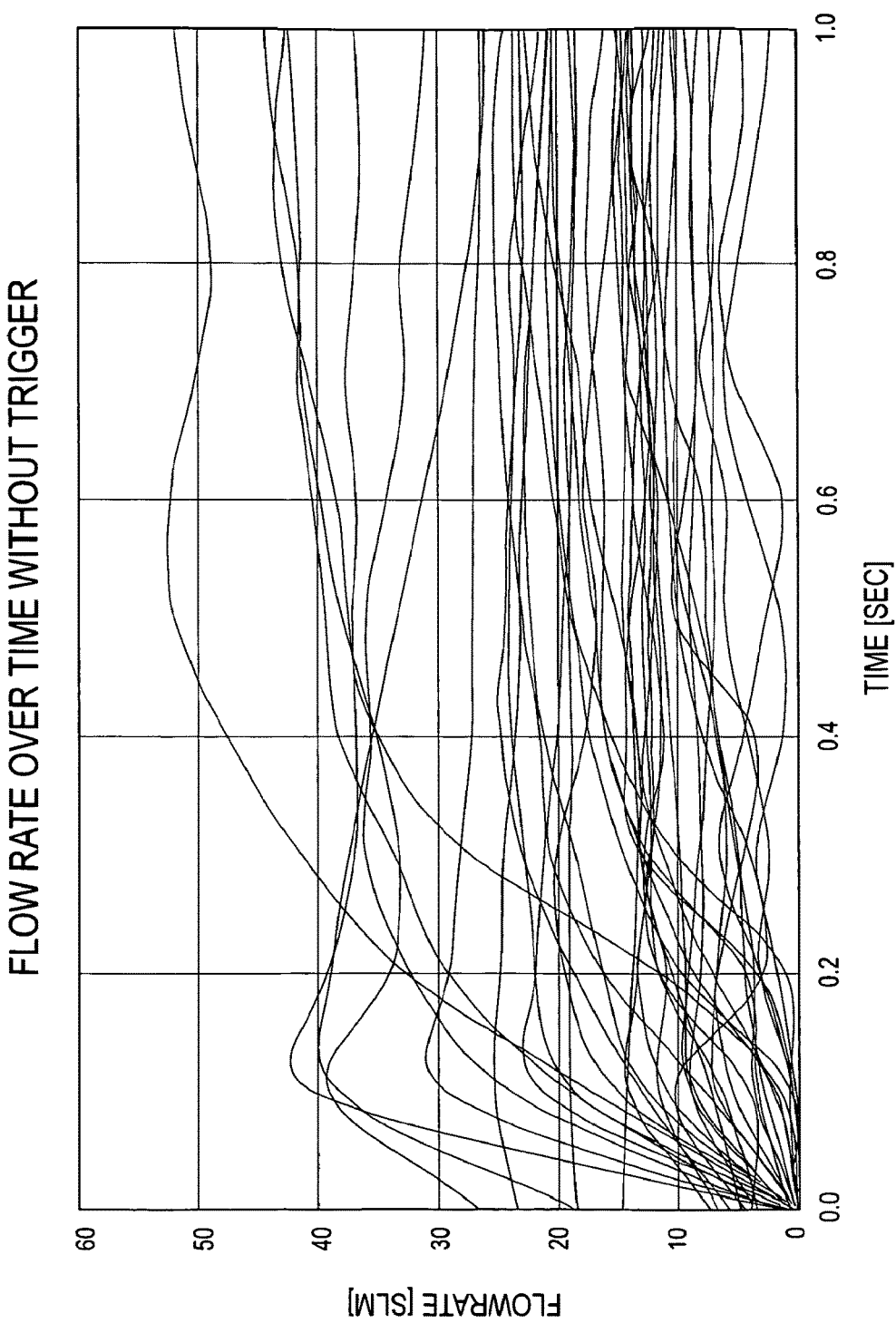
FIG. 100 shows a flow rate chart illustrating flow rates through a device which does not utilize a trigger of the type disclosed herein.
Figure 101:
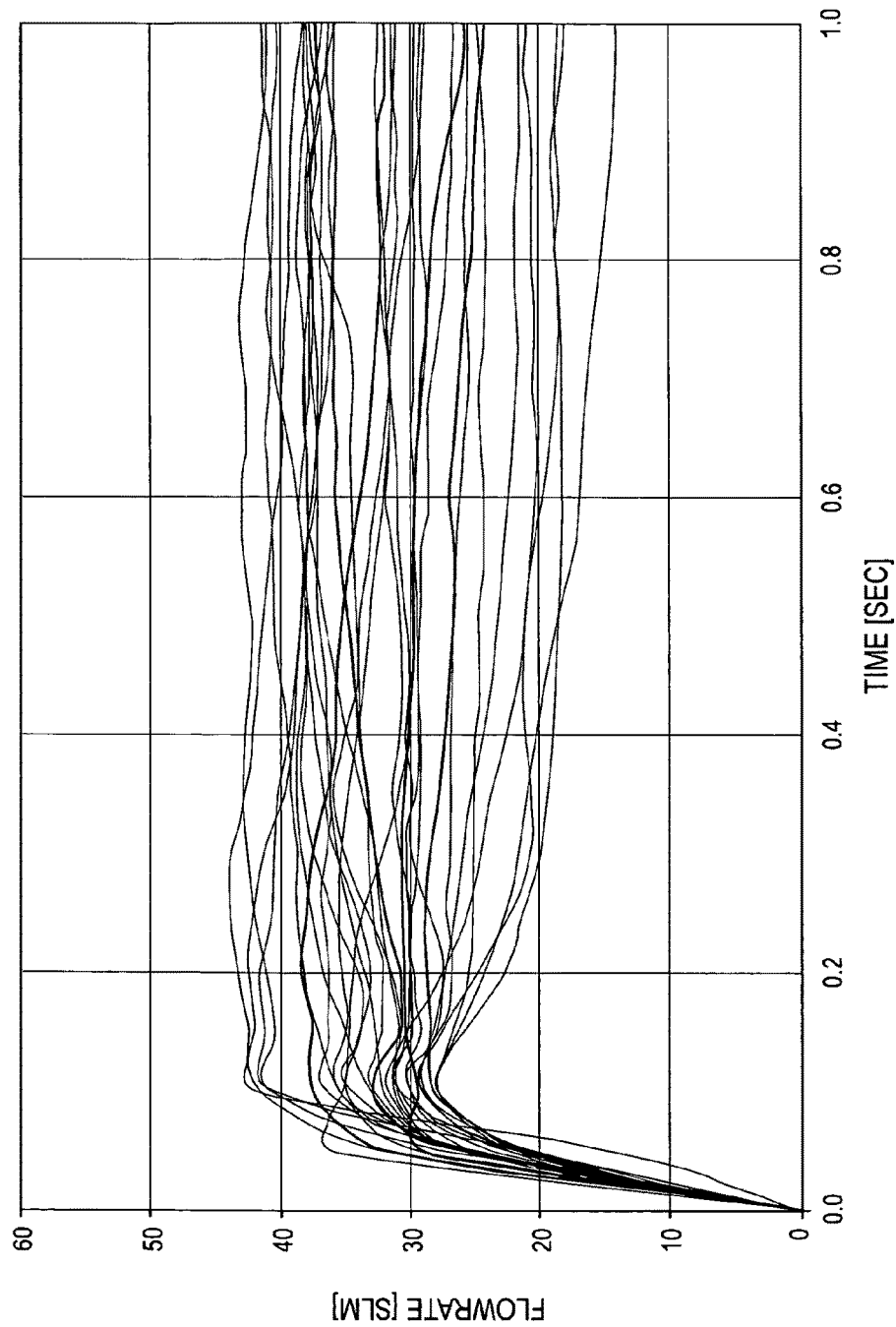
FIG. 101 shows a flow rate chart illustrating flow rates through a device which does utilize a trigger of the type disclosed herein.

FIG. 99 shows a 3D side perspective view of an embodiment of the trigger E after it has assumed the fully opened position. The trigger E functions as follows: as the patient creates a vacuum in the internal portion of the mouthpiece B, the trigger E inverts and the four "petals" of the trigger open (see also FIGS. 25-26). The primary function of the trigger is to ensure consistent and uniform dosing. In this regard, FIGS. 100-101 show test results from flow rate tests conducted with the apparatus with and without the trigger E. The trigger E may reset itself when a user fails to draw sufficient airflow into the apparatus, resulting in incomplete or inconsistent aerosolization of the powder contained in the receptacle Q. This phenomenon can typically be avoided by providing sufficient training on the correct inhalation maneuver for operating the apparatus.

FIG. 102 shows a top view of a lid stock of a receptacle Q after the receptacle Q is used in the apparatus. The outlet opening in the center has been formed by the puncturing and deoccluding device G (and more specifically by the end 70*g*) and the two arc-shaped inlet openings have been formed by the cutter mechanism H (and more specifically by the teeth 80*t*). The member G plunges into the foil lid stock on the top of the receptacle blister pack Q to create the central outlet opening. The two teeth 80*t* of the cutter mechanism H are timed to descend into the foil shortly after or essentially simultaneously with the member G. Such movement is controlled by contact between the corresponding cam surfaces of the members H and J. As the mouthpiece B is rotated, the member G rotates to displace foil and thereby create a center outlet hole while the teeth 80*t* form two approximately 120° arc-shaped openings which provide inlet for air through the blister pack Q. In some embodiments, the teeth 80*t* do not actually cut the foil in forming the inlet openings, but rather propagate a controlled tear as illustrated in FIG. 173.

Figure 103:
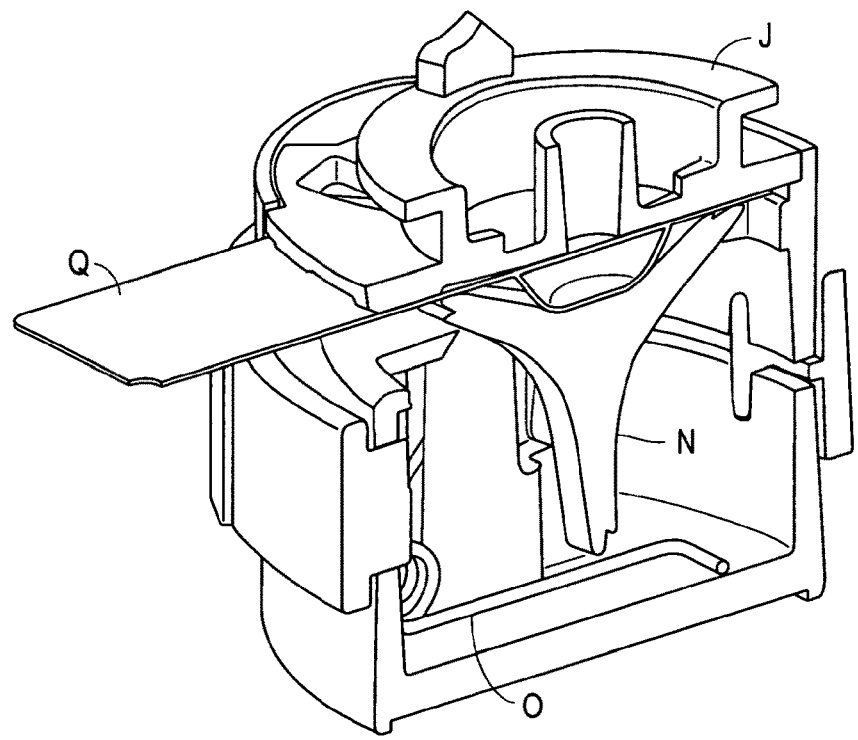
FIG. 103 shows a cut-away view of a bottom portion of an apparatus according to the invention with a receptacle installed therein.

FIG. 103 shows a cut-away view of the lower portion of another embodiment of an apparatus and shows a receptacle Q in the home position and shows a positioning of the components J-Q of FIG. 9.

Figure 104:
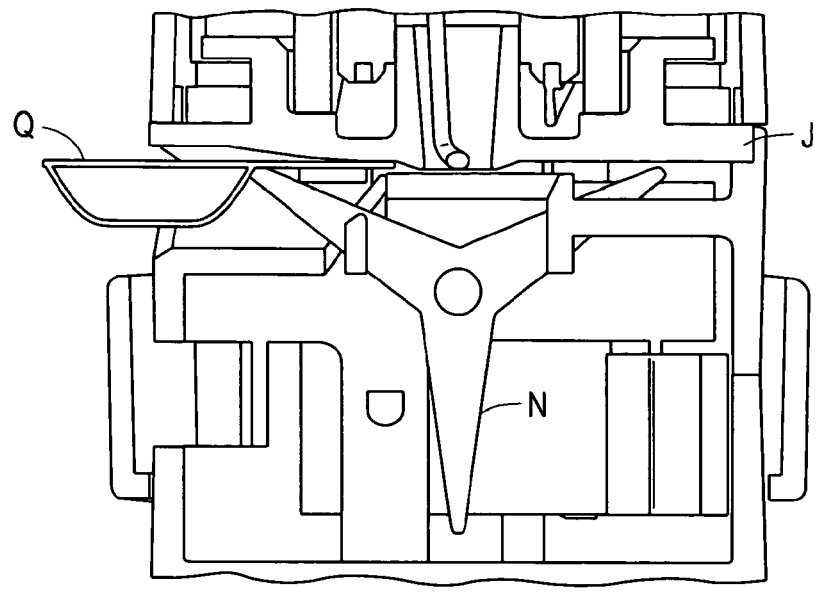
FIG. 104 shows a cut-away view of a bottom portion of an apparatus according to the invention and shows an initial insertion position of the receptacle into the apparatus. The leading edge of the receptacle has passed between an arm of the receptacle impacting member and a bottom surface of the lower bearing member and the front curved surface of the tub portion of the receptacle has come into contact with the arm of the receptacle impacting member.
Figure 105:
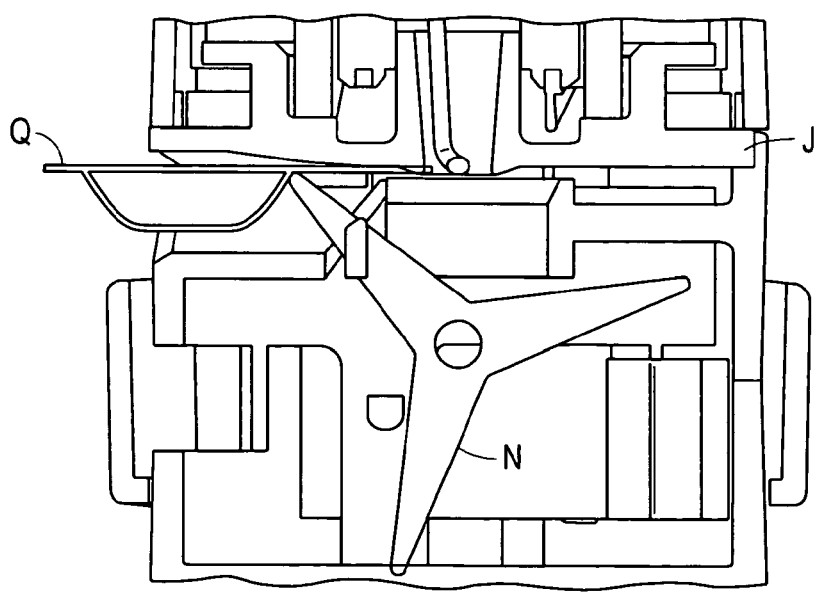
FIG. 105 shows another cut-away view of FIG. 104 and shows an intermediate insertion position of the receptacle into the apparatus. The front curved surface of the tub portion of the receptacle has caused the arm of the receptacle impacting member to move or partially rotate clockwise causing the receptacle impacting member to also move downwards against the biasing force of the torsion spring.
Figure 106:
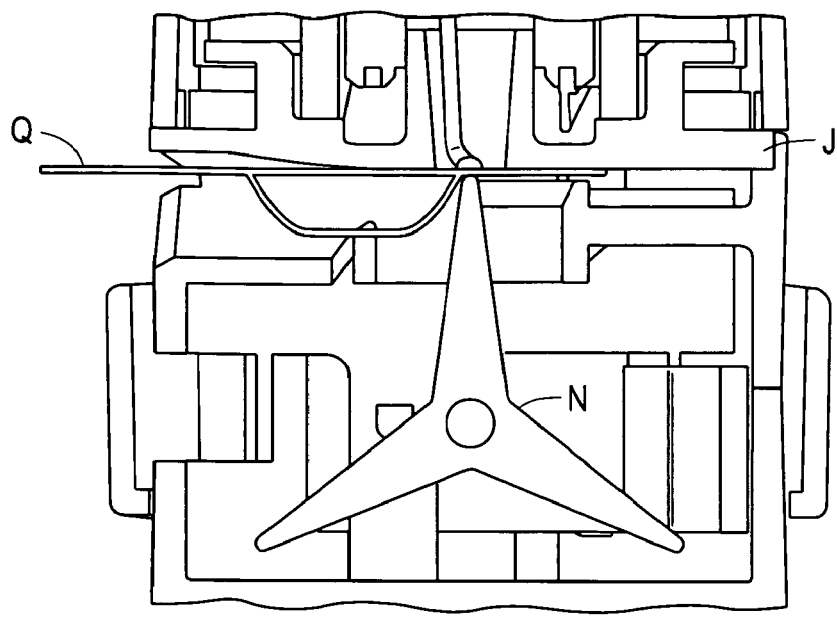
FIG. 106 shows another cut-away view of FIG. 104 and shows another intermediate insertion position of the receptacle into the apparatus. The front curved surface of the tub portion of the receptacle has caused the arm of the receptacle impacting member to move or partially rotate clockwise to about the twelve o'clock position causing the receptacle impacting member to also move downwards to its maximum downward position against the biasing force of the torsion spring.
Figure 107:
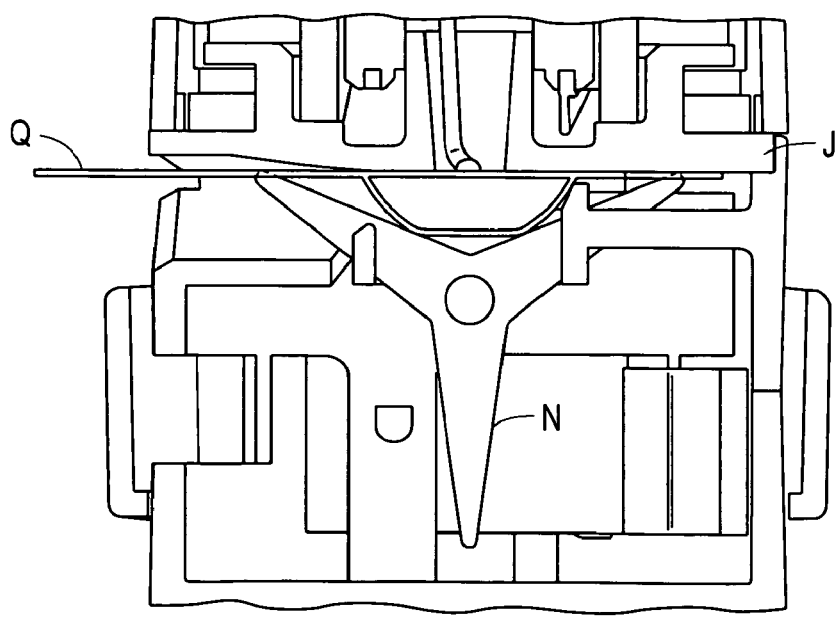
FIG. 107 shows another cut-away view of FIG. 104 and shows the final insertion position of the receptacle into the apparatus. The front curved surface of the tub portion of the receptacle has caused the arm of the receptacle impacting member to rapidly move or partially rotate clockwise to about the two o'clock position causing another arm of the receptacle impacting member to impact the rear curved side of the tub portion of the receptacle and then assume a ten o-clock position. During this insertion movement, the receptacle impacting member moves back upwards to its maximum upward position under the biasing force of the torsion spring.

FIGS. 104-107 shows a cut-away view of the lower portion of another optional apparatus. This apparatus is similar to that on FIGS. 1-2 except that the receptacle impacting member N is replaced with a differently configured receptacle impacting member. Unlike the previous member, this member does not utilize shoulders at the free ends of the lobes. Furthermore, in this embodiment, the lobes or arms are caused to rotate or move by contact with the tub of the receptacle instead of by contact with the leading end of the receptacle. FIG. 104 shows an initial insertion position of the receptacle. FIG. 105 shows how the receptacle starts causing the lobe to move and how this occurs by contact engagement between the tub and the left-side lobe. FIG. 106 shows how the receptacle continues moving the left-side lobe to center or vertical position (i.e., the position which causes maximum compression of the torsion spring O) and how this occurs by contact engagement between the tub and the lobe. FIG. 107 shows the receptacle in the home position. After the receptacle moved the left-side lobe past the center or vertical position, the torsion spring O automatically released its energy causing the left-side lobe of FIG. 106 to rotate rapidly and impact or strike the tub of the receptacle Q with the lobe. This occurred when the receptacle was in a position intermediate of the positions shown in FIGS. 106 and 107.

FIGS. 108-111 show various views of one non-limiting embodiment of a receptacle Q as shown in FIG. 9, and illustrate the various features thereof. As is shown in FIGS. 108-111, the receptacle Q has a generally rectangular configuration and includes a leading end 170*c* having two oppositely arranged tapered or chamfered edges 170*f* which are sized and configured to engage and spread apart the ends 130*a* of the lock member M. Two generally oppositely arranged recesses 170*g* are arranged to receive therein the ends 130*a* of the lock member M after the ends 130*a* slidably engage the side edges 170*b*. Before the ends 130*a* of the lock member M are caused to move away from each other by edges 170*f* and 170*b* and after the ends 130*a* are positioned in the recesses 170*g*, the apparatus is unlocked and the mouthpiece B can be rotated. However, when the ends 130*a* are caused to move away from each other by edges 170*f* and 170*b* and before the ends 130*a* are positioned in the recesses 170*g*, the apparatus is locked and the mouthpiece B cannot be rotated. The receptacle Q additionally also utilizes a generally spherical tub portion 170*h* which have a generally flattened bottom portion 170*i*. The tub portion is sized and configured to contain therein a desired amount of the powder which will be aerosolized by the apparatus. The receptacle Q also utilizes a tab or gripping portion that includes a rear edge 170*d* and oppositely arranged side edges 170*a*. An optional recess 170*e* can be utilized on the read edge 170*d*. The end of the receptacle Q opposite the leading end does not utilize chamfered corners (like the leading end) so as to prevent improper insertion of the receptacle Q into the apparatus (without the chamfered corners, this end of the receptacle Q will not act to spread the arms of the lock member M). The upper surface of the receptacle is heat sealed with a foil lid stock. The receptacle Q can also be made of the same material and have substantially the same width as the conventional Exubera™ receptacle or single-use blister pack. Of course, other configurations and shapes for the receptacle Q are contemplated. For example, the receptacle Q can utilize the leading taper 170*f* and one notch 170*g* on only one side of the receptacle Q. Additionally, the receptacle Q can be made of the materials described above and can even be made transparent or translucent. Finally, the apparatus can also utilize a lockout or receptacle locking feature or system of the type used in one or more of the PDS devices described above.

Considerations which should be taken into account in the design and configuration of the receptacle Q include the following: the tub shape should be a simple shape preferably made up of circular areas and straight lines; regions of re-circulating flow within the tub should be minimized; the design should be such that there is a constant accelerating flow in the tube that this flow should continue up through the feed tube FT; areas of boundary layer separation should also be minimized and/or avoided as regards the air flow within the tub and into and through the feed tube FT; sudden expansions of air flow within the tub which produce eddies that are slower are acceptable as they provide more room for expansion. The receptacle Q can also be pressurized. Additionally, the foil lidstock can be connected to the synthetic resin body portion using e.g., ultrasonic welding or ultrasonic staking.

FIG. 112 shows an air flow path through the blister itself and the apparatus. Air enters the two 120° arc-shaped inlet openings (see FIG. 102) out the center opening and into the feed tube FT (i.e., the centrally disposed tube of member J) drawing with it fluidized powder from the receptacle or blister pack Q. The flow then moves up through the feed tube FT and through the central opening of the orifice member F, through the trigger E, out through the mouthpiece B, and finally into the lungs of the user. As the powder-laden air passes through the orifice member F and the trigger E, larger agglomerated particles of the powder are deagglomerated to create a fine aerosol suitable for deposition in the deep lung.

FIG. 113 shows both an air flow path through the blister itself and a bypass air flow path through the apparatus of the type shown in FIGS. 1 and 2. The bypass air flow is designed to reduce the overall air flow resistance of the apparatus in order to improve patient comfort. The bypass air enters the apparatus through gaps in the components (underneath the skirt L) and then passes up through the six openings 80e in the cutter mechanism H. The bypass air flow also serves to focus the central flow of aerosol. Note that the leak paths shown in FIG. 113 are intended to be minimized. The main contributors to aerosol performance are the ratio of blister flow to total flow (controlled by the size of the bypass holes 80e in the cutter mechanism H), the size of the central opening in orifice member F, and the length of the slits 50c and 50d on the trigger E. By way of non-limiting example, the apparatus shown in FIG. 1 can have a blister flow of about 40%, a trigger slit length of about 0.34 inches and a diameter of about 3.8 mm for the central opening of the orifice member F. The invention contemplates utilizing blister/total ratios of between about 20% and about 70% and orifice member F opening diameters of between about 3 mm and about 13 mm.

FIGS. 114-123 show various cross-section views of one embodiment of the apparatus shown in FIGS. 1 and 2 in different operating positions.

Figure 128:
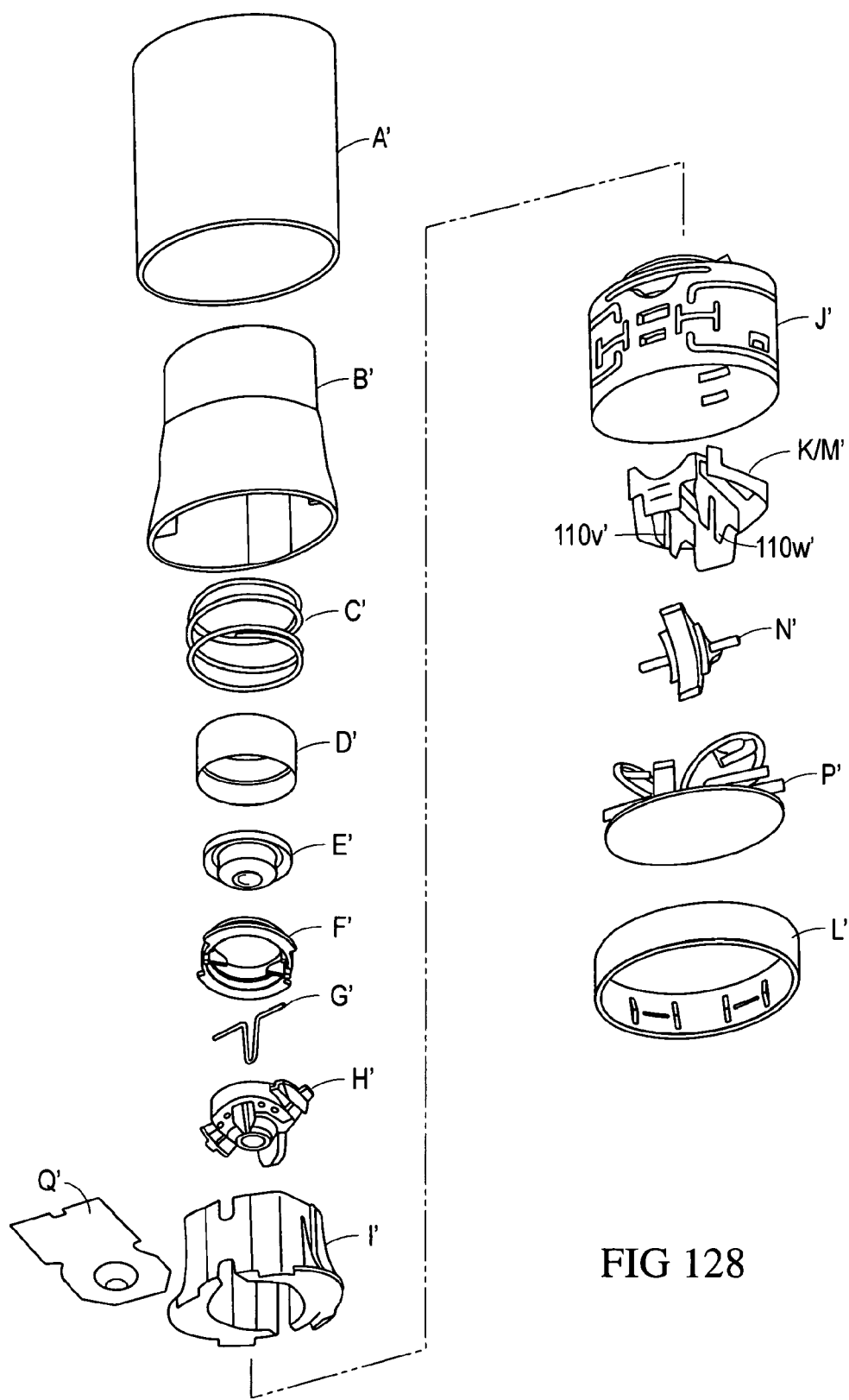
FIG. 128 shows an exploded view of another embodiment of the invention.

FIGS. 128-138 show an alternative embodiment. In this embodiment, the part count of the device is fourteen, including the optional cap. Differences between the embodiments of FIG. 9 and FIG. 128 are discussed below.

Figure 129:
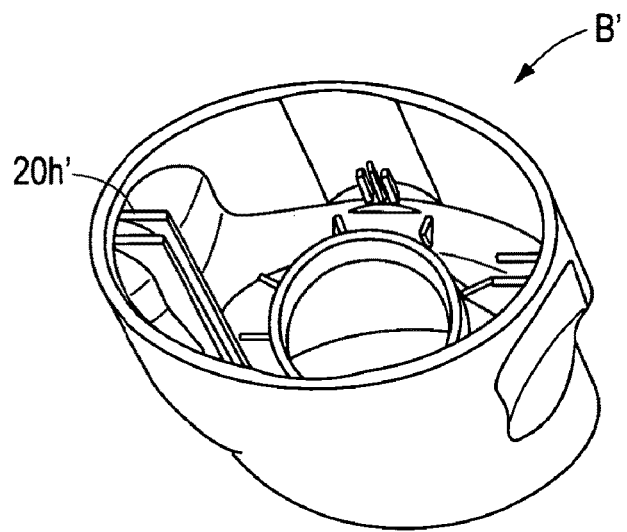

Referring to FIG. 129, the ultrasonic staking of the FIG. 9 embodiment has been replaced by an ultrasonic weld. The cruciform shape of projections 20h of the FIG. 9 embodiment are replaced by four ribs 20h'. A small rib has been lengthened (the central rib of the three in the images above) to provide additional lead-in of the compression spring C' during assembly.

Figure 130:
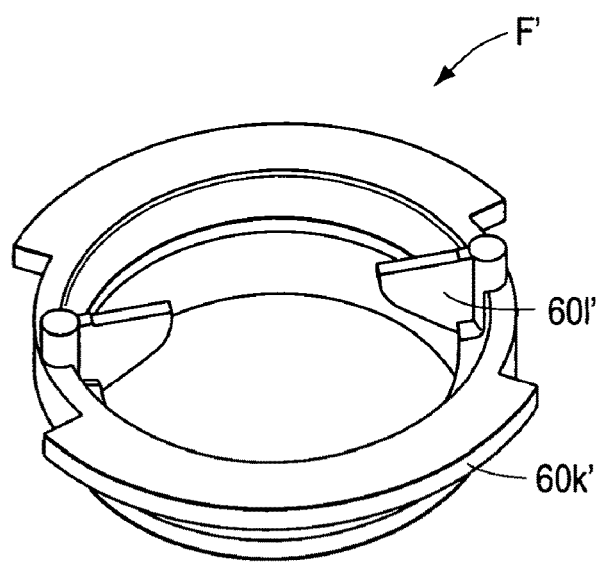

Referring to FIG. 130, an adapter F' snaps to retainer member D' to constrain trigger E'. The adapter F' snaps to cutter member H' to constrain deoccluding device G'. The adapter F' and cutter member H' together form a flange to transmit the force of compression spring C' to aerosol module D'-H'. The snaps hold the aerosol module D'-H' together while minimizing leaks.

The adapter F' has an interrupted flange 60k' added to the outside diameter of the part to allow it to snap to the cutter member H', eliminating the need for glue. Glue is generally not preferred for use in inhalation devices. The adapter F' has two radial ribs 60l' that engage features in the cutter member H' to hold the deoccluding device G' in place, eliminating the need for heat staking. The elimination of heat staking reduces the potential for particulate generation during assembly. The outer circumferential rib 60g of the FIG. 9 embodiment has been eliminated. Eliminating the outer circumferential rib 60g reduces the surface area of the inside of the aerosol module D'-H', with an associated reduction in device deposition.

Figure 131:
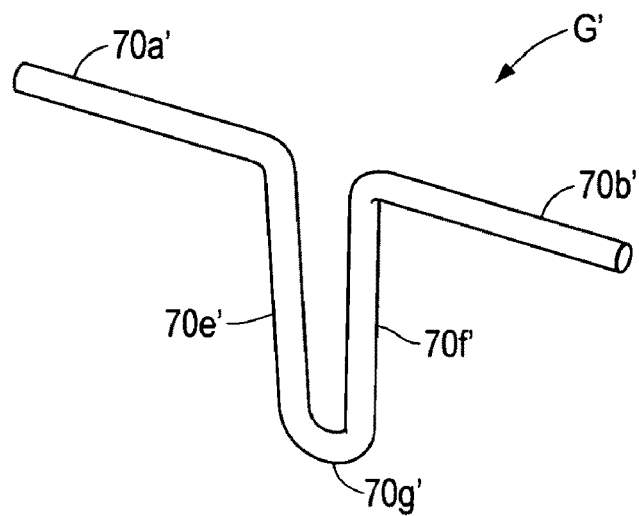

Referring to FIG. 131, relative to the embodiment of FIG. 9, the geometry of a central part 70e' to 70g' of the deoccluding member G' is the same, but the overall span and shape of the free ends 70a' and 70b' is different. The longer free ends 70a', 70b' allow the deoccluding member G' to be held by the adapter F' and the cutter mechanism H', eliminating the need for heat-staking. The lengthened free ends 70a', 70b' also allow the deoccluding member to be retained in the device even if the aerosol module D'-H' snaps fail.

Figure 132:
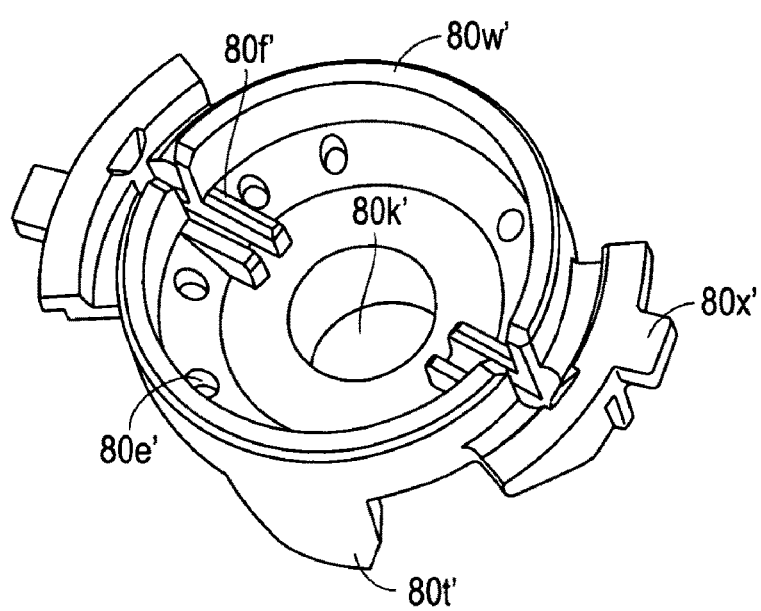

Referring to FIG. 132, snaps hold the aerosol module D'-H' together while minimizing leaks. The vertical wall 80w' around the perimeter of the cutter mechanism H' helps constrain the deoccluding device G' in the device even if the aerosol module D'-H' snaps fail. Tabs 80x' on the edge of the cutter mechanism H' engage vertical channels on the bearing member I' to synchronize the rotation of the aerosol module D'-H' with the rotation of the mouthpiece B'.

Figure 133:
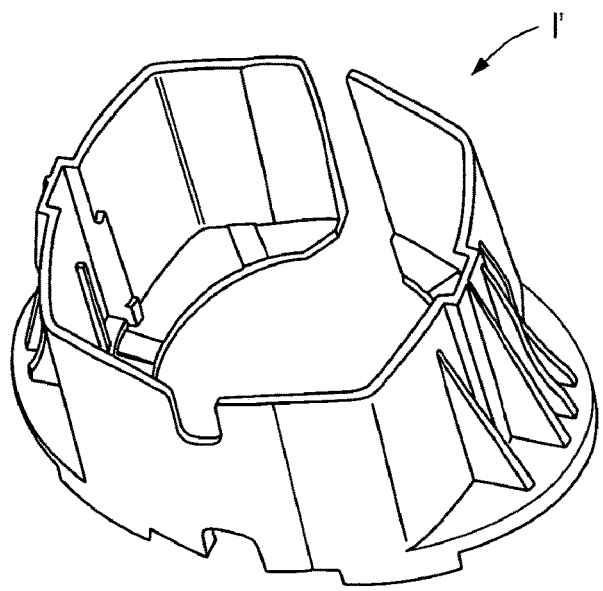

Referring to FIG. 133, the upper bearing member I' spreads open during assembly to envelop the flange on the body J'. Once welded to the mouthpiece B', the upper bearing member I' is unable to spread open again, thus securely retaining the upper half of the device to the lower half. The upper bearing member I' spins freely on the flange of the body J'. Details on the underside of the upper bearing member I' engage the interlock tabs on the tray K/M' to lock rotation of the mouthpiece B' if the receptacle Q' is partially inserted. Details on the underside of the upper bearing member I' constrain the interlock tabs on the tray K/M' during rotation of the mouthpiece B' to prevent receptacle Q' insertion or removal when the mouthpiece B' is not in the home position.

Figure 134:
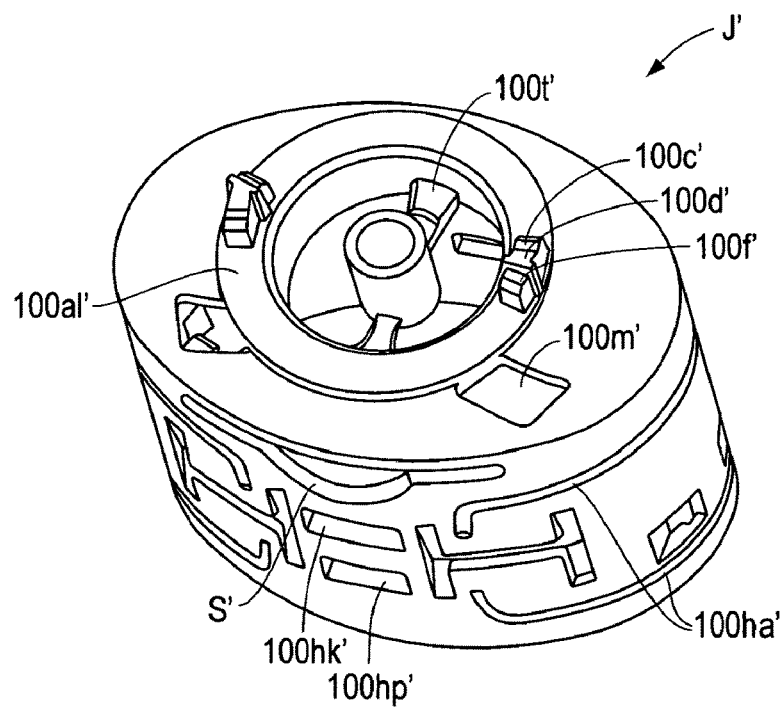

Referring to FIG. 134, the body J' has a receptacle opening S' shaped to discourage upside-down receptacle insertion. The shape also provides side-to-side receptacle location upon insertion. Holes 100hk' and 100hp' in the vertical walls of the body J' provide snap features for the tray K/M' and baseplate P'. H-shaped recesses 100hl' in the vertical walls of the body J' provide snap features for the sleeve L'. Rounded grooves 100ha' in the vertical walls of the body J' provide snap features for the cap A'. The reverse rotation tooth detail 100d' is widened to increase the force required to rotate the device in the wrong direction.

Figure 135:
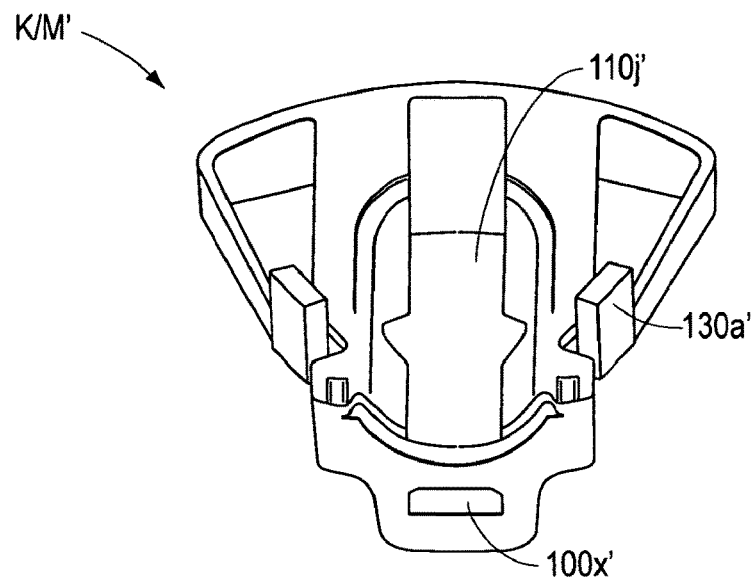

Referring to FIG. 135, tray K/M' includes integral protrusions 130a'. Tray K/M' includes vertical slots 110v' on its underside to constrain motion of the receptacle impacting member N'. Cam surfaces 110w' on the underside of the tray K/M' adjacent to the central rectangular opening 110r engage secondary cams 140g', 140h' on the receptacle impacting member N'. This helps guide the receptacle impacting member N' past the feed tube FT' without stressing the spoke-like members 100t', 100u' on the body J' that hold the feed tube FT' in place. Two small wedge-shaped protrusions 130a' on the top side of the tray K/M' help ensure the leading edge of the receptacle Q' engages a recess 140e' in an arm 140a', 140b', or 140c' of the receptacle impacting member N'. Snap details on the front 110x' and rear (not shown) of the tray K/M' retain the tray K/M' in holes 100hk' provided in the body J'.

Figure 136:
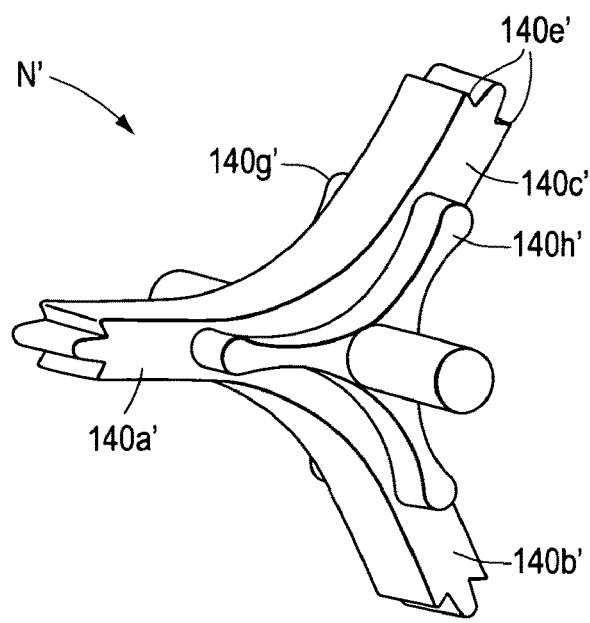

Referring to FIG. 136, an axle 140i', 140j' of the receptacle impacting member N' engages the spring flexures 150a', 150b' in the baseplate P'. Secondary cams 140g', 140h' (smaller lobes on either side of the larger lobes) relieve the stress of the receptacle impacting member N' spring force as the main arm 140a', 140b', or 140c' sweeps past the feed tube FT'. The receptacle impacting member N' is left-right symmetrical, which eliminates potential orientation errors during assembly.

Figure 137:
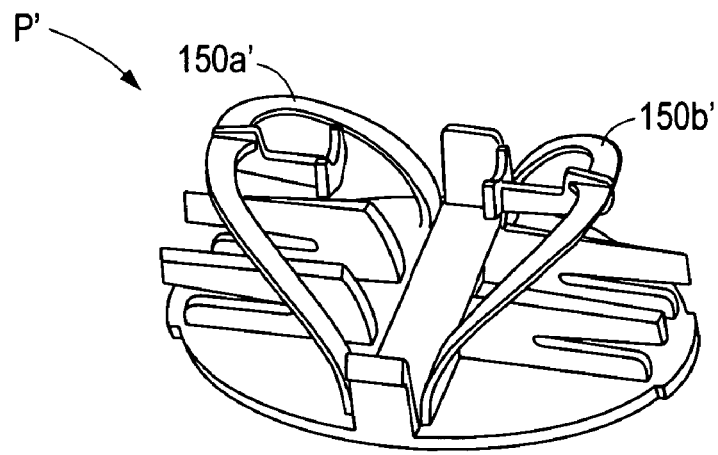

Referring to FIG. 137, arched wings 150a', 150b' of the baseplate P' provide the spring force for the receptacle impacting member N'.

Figure 138:
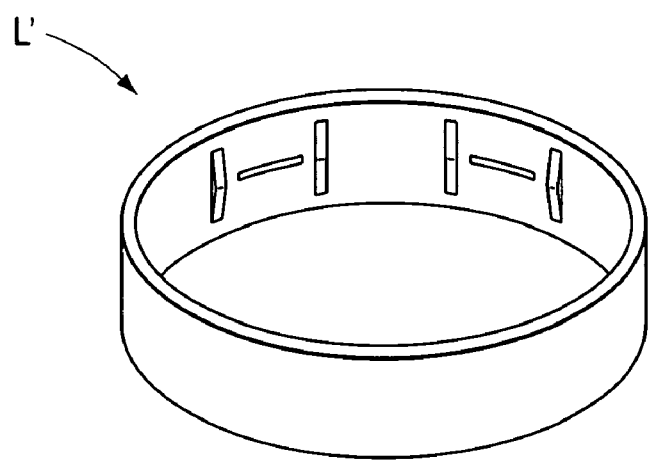

Referring to FIG. 138, the skirt member L' has different features around the internal surfaces to reflect the fact that it is snapped onto the body J', rather than sandwiched between other parts of the assembly. The skirt member L' does not have a central recess (cf., element 120f of skirt member L).

FIGS. 124-127 show a preferred cutter mechanism H configuration as well as details of a preferred tooth configuration. As is illustrated in the teeth cross-section of FIG. 126, the leading end of each tooth is blunt, e.g., rounded, so as not to cut the foil but instead to produce a controlled tear. FIG. 127 shows one of the teeth with non-limiting dimensions in "mm".

Air Flow Characteristics

With reference to FIGS. 139-178, the following description relates to the air flow considerations and characteristics of the apparatus. The following are definitions used in the flow diagram figures:

Inlet: Opening to permit flow of air from environment to internal airflow within device.

TV: Trigger Valve, a mechanism for enforcing threshold pressure differential such that no airflow can occur until pressure drop across Trigger Valve exceeds the threshold pressure differential. Typically, pressure differential is provided by user-imposed inhalation vacuum. Once open, the ideal Trigger Valve remains in the open state, offering air flow resistance below 0.4 sqrt (cm $H_2O$)/(liters/min) and preferably below 0.1 sqrt (cm $H_2O$)/(liters/min) until pressure drop across Trigger Valve drops below 5 cm $H_2O$ and preferably below 1 cm $H_2O$.

MP: Device Mouthpiece.

Exit: Flow exit from device, always assumed hereinafter to be at the downstream orifice of Mouthpiece.

PF: Powder Fluidization apparatus for providing powder medicament fluidization, or entraining powder medicament in air stream, independent of powder medicament agglomeration state.

PD: Powder Deagglomeration apparatus for reducing fluidized powder medicament suspended in air stream to primary particle state or near primary particle state.

FR: Flow Regulator apparatus for providing variable resistance as a function of pressure differential, where the pressure differential is provided by user imposed inhalation vacuum, such that flow through the Flow Regulator apparatus or flow to the user through the mouthpiece is held constant or within a predetermined relationship of flow rate vs. pressure differential.

AB: Airflow Bypass, which may be a conduit having predetermined constant flow resistance or flow resistance vs. pressure differential relationship, typically used in a local parallel flow circuit element.

FIGS. 139 through 161 show passive DPI flow architecture in block diagram form, with arrows showing the direction of airflow from air Inlet to Mouthpiece and Exit. Note that each box represents an element that would offer some airflow resistance similar to flow resistance through an orifice, where flow resistance at flow rate Q and pressure drop ΔP is defined as $$R=(SQRT(\Delta P))/Q$$

and n series flow resistances $R_i$ sum by the mathematical relationship $$R_{1+2+\ldots+n} = \sqrt{\sum_{i=1}^{n} R_i^2}$$

Parallel flow resistances combine by the mathematical relationship $$R_{1+2+\ldots+n} = \frac{1}{\sum_{i=1}^{n} \frac{1}{R_i}}$$

Figure 139:
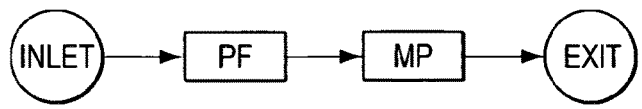

FIG. 139 is a block diagram of the flow architecture of a typical passive DPI, showing simple air Inlet, Powder Fluidization (PF) apparatus, Mouthpiece (MP), and Exit to the mouth of the user.

Figure 140:
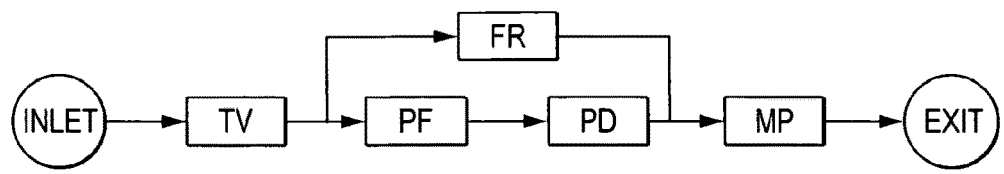

FIG. 140 is a block diagram of the passive DPI having series-parallel flow architecture previously disclosed in U.S. Pat. No. 6,606,992. An advantage of this series-parallel flow architecture is that total flow of air from the device Exit is predetermined to be a known function of the user-applied inhalation vacuum. In some embodiments, the predetermined function may be a simple constant, such that flow of aerosol-laden air from the device Exit is always constant. In other embodiments, the predetermined function may have slight positive slope, such that flow of aerosol-laden air from the device Exit increases slightly with increase in user-applied inhalation vacuum, wherein the slight positive slope may have advantages in perceived user comfort. A disadvantage of the series-parallel flow architecture shown in the block diagram of FIG. 140 is that, because of the variable airflow through the Flow Regulator (FR), airflow through the Powder Fluidization (PR) and Powder Deagglomeration (PD) apparatus is variable and dependent on the user-applied inhalation vacuum.

Figure 141:
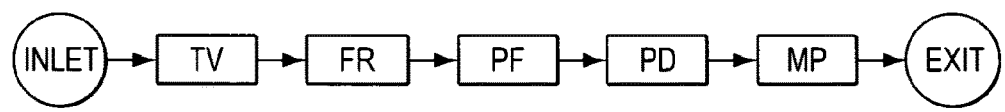
Figure 142:
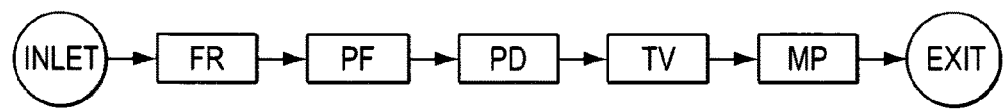
Figure 143:
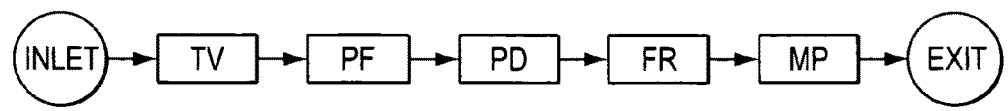
Figure 144:
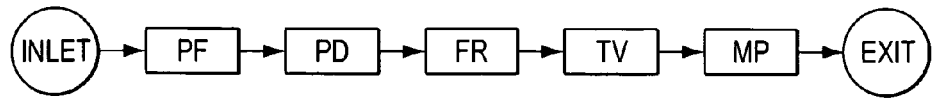
Figure 145:
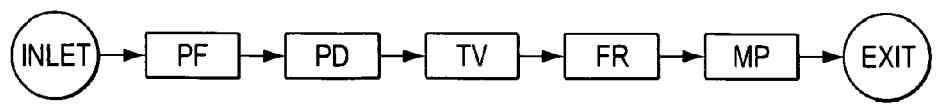

FIG. 141 is a block diagram of a purely series flow architecture such that at any time during actuation the airflow through all elements of the device is the same. The inherent disadvantage of a purely series flow architecture is that flow resistances combine in a manner such that overall device flow resistance can be high and negatively affect user comfort.

FIGS. 142 through 145 are other possible embodiments of purely series passive DPI flow architecture.

Figure 146:
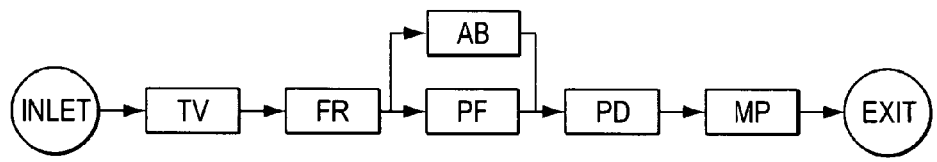
Figure 147:
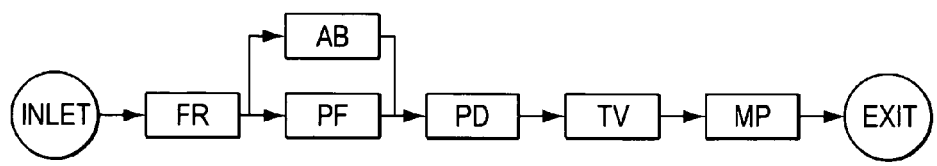
Figure 148:
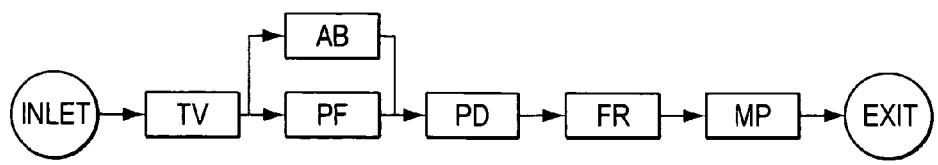
Figure 149:
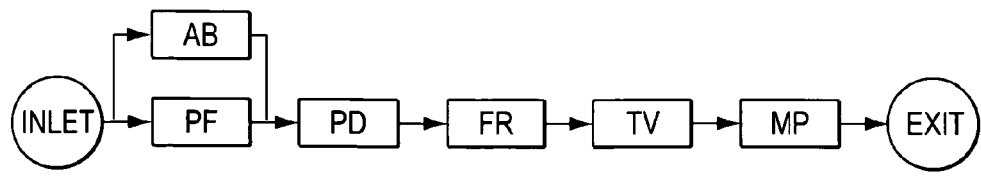
Figure 150:
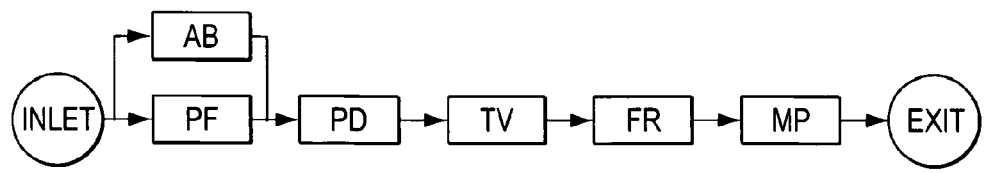

FIG. 146 is a block diagram of a passive DPI having series flow architecture as presented in FIG. 141 with an additional Air Bypass (AB) arranged in parallel to the Powder Fluidization (PR) apparatus, wherein the Air Bypass is intended to lower the flow resistance to the Powder Fluidization (PR) apparatus, thereby lowering the DPI overall flow resistance.

FIGS. 147 through 150 are block diagrams of passive DPI as further embodiments of the principles described in FIG. 146.

Figure 151:
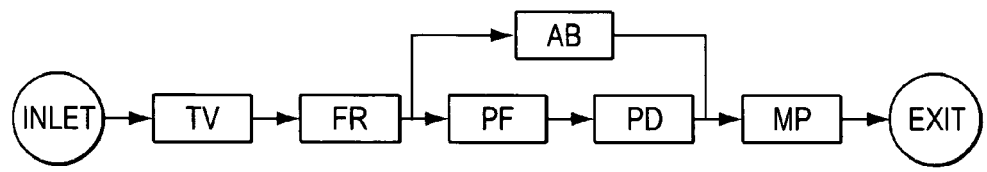
Figure 152:
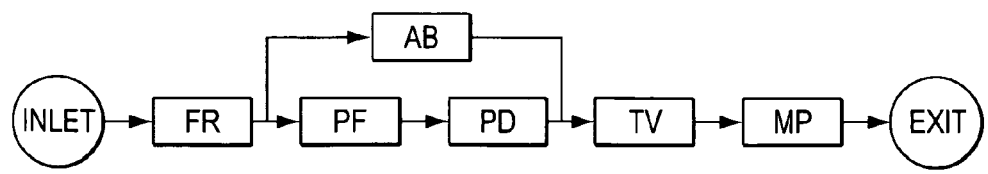
Figure 153:
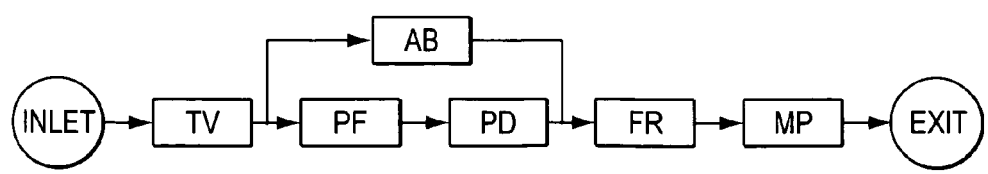
Figure 154:
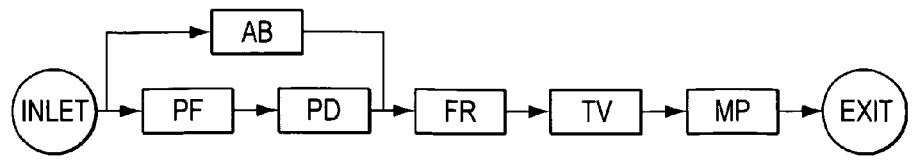
Figure 155:
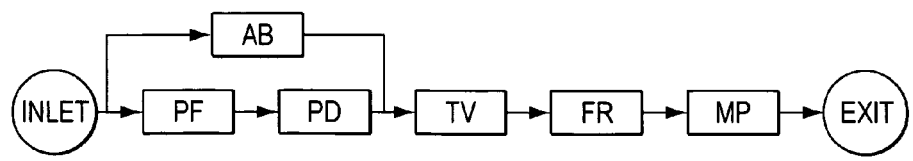

FIG. 151 is a block diagram of a passive DPI having series flow architecture as presented in FIG. 141 with an additional Air Bypass (AB) parallel to the Powder Fluidization (PR) apparatus and Powder Deagglomeration (PD) apparatus, wherein the Air Bypass is intended to lower the flow resistance to the combined PR and PD apparatus, thereby lowering the DPI overall flow resistance.

FIGS. 152 through 155 are block diagrams of passive DPI as further embodiments of the principles described in FIG. 151.

Figure 156:
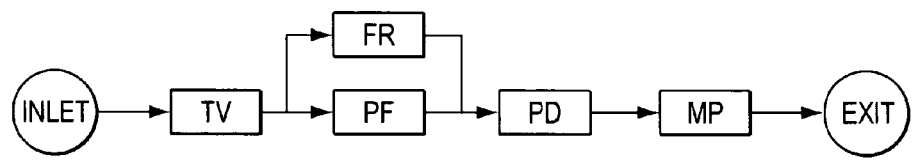
Figure 157:
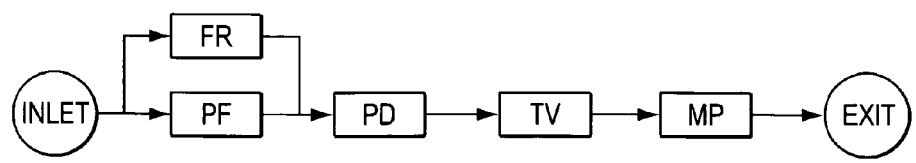

FIGS. 156 and 157 are block diagrams of passive DPI having series-parallel flow architecture as further embodiments of the principles presented in FIG. 140, with the exception that the Flow Regulator (FR) is arranged in series with only the Powder Deagglomerator (PD) apparatus.

Figure 158:
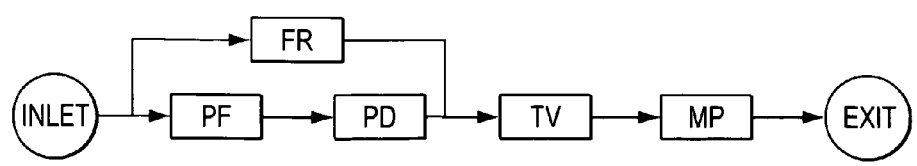

FIG. 158 is a block diagrams of a passive DPI having series-parallel flow architecture as a further embodiment of the principles presented in FIG. 140, with the exception that the Trigger Valve (TV) is arranged downstream of the Powder Deagglomerator (PD) and just upstream of the Mouthpiece (MP).

Figure 159:
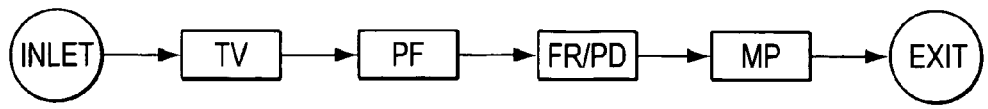
Figure 160:
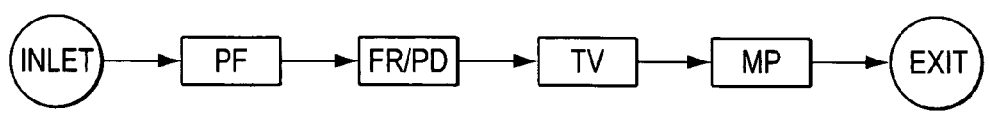

FIGS. 159 and 160 are block diagrams of passive DPI having series flow architecture as further embodiments of the principles presented in FIG. 231, with the exception that the Flow Regulator (FR) is combined with the Powder Deagglomerator (PD) such that the same apparatus performs both functions.

Figure 161:
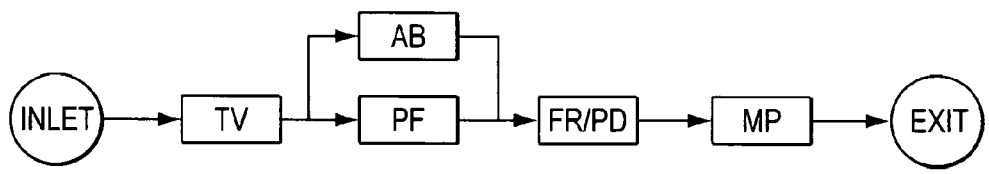
Figure 162:
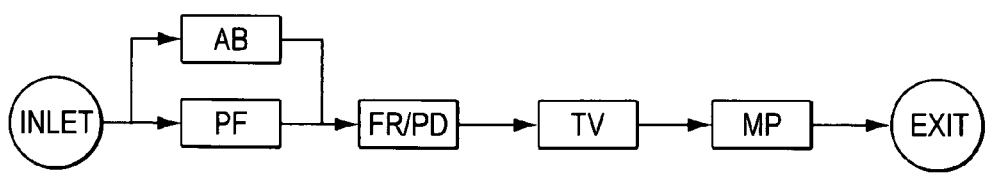
Figure 163:
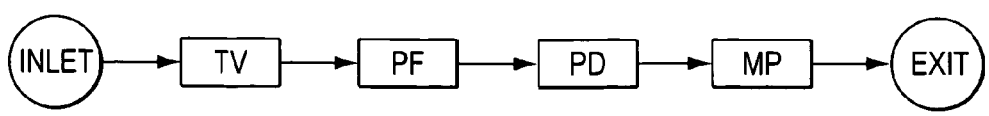
Figure 164:
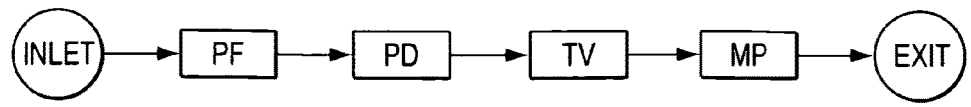

FIGS. 161 and 162 are block diagrams of passive DPI having series-parallel flow architecture as further embodiments of the principles presented in FIGS. 159 and 160, with an additional Air Bypass (AB) arranged in parallel to the Powder Fluidization (PR) apparatus, wherein the Air Bypass is intended to lower the flow resistance to the Powder Fluidization (PR) apparatus, thereby lowering the DPI overall flow resistance.

FIGS. 159 through 162 are arrangements that reflect a preferred embodiment.

FIGS. 163 through 168 are block diagrams of passive DPI having flow architecture as further embodiments of the principles presented in FIGS. 140 through 162 without the inclusion of Flow Regulator (FR).

Figure 169:
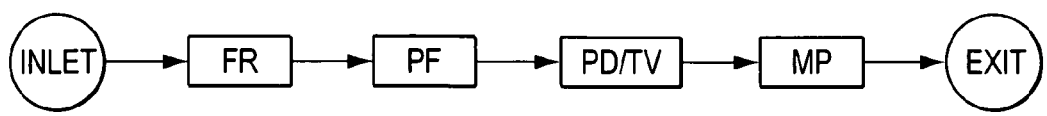
Figure 170:
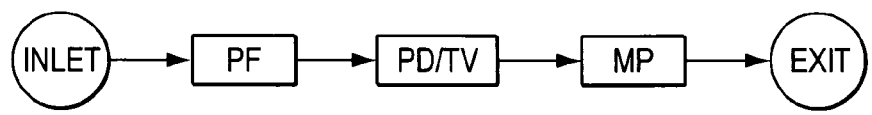
Figure 171:
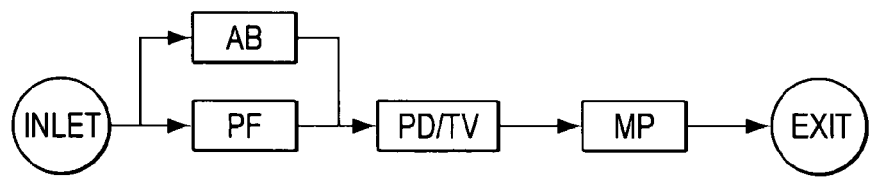

FIGS. 169 through 171 are block diagrams of passive DPI having flow architecture as further embodiments of the principles presented in FIGS. 140 through 162, but modified by combining PD and TV functions into a single apparatus.

It should be noted that the series of elements shown in FIGS. 139-171 are merely presented as examples of possible arrangements. The particular examples presented herein are exemplary only; in the interest of brevity, not all possible arrangements are shown. The elements can be arranged in any desired order, depending on the desired flow characteristics.

Integral to a preferred embodiment is the division of aerosolization into two functional stages, Powder Fluidization (PF) and Powder Deagglomeration (PD), as described above. The PD stage may employ shearing airflows, turbulent airflows, powder particle collision with impaction entities, or accelerating flows. For the primary particle sizes in the approximate range of interest for pulmonary delivery, between 100 nm and 10 μm, and preferably between 500 nm and 3 μm, accelerating flows have been found to be most effective for deagglomeration. Such accelerating flows may be accomplished by applying a pressure drop across a simple orifice through which the aerosol, as fluidized powder, is introduced. See FIG. 172.

In other configurations, the Powder Deagglomerator (PD) is combined with Flow Regulator (FR) such that the same apparatus performs both functions. An illustration of one example of this combined FR/PD embodiment is shown in FIG. 173, as an oblique view with arrow indicating the direction of flow. FIG. 174 is an illustration of the same example of this combined FR/PD embodiment in a view from the inlet side, showing the approximate configuration of the orifice during actuation of the passive DPI. One advantage of this combined FR/PD stage, especially when the materials used are flexible and inert, such as silicone rubber, the orifice will recover to the approximate shape shown in FIG. 173 after actuation of the passive DPI, such that the orifice of the FR/PD will tend to be self-deoccluding.

Figure 175:
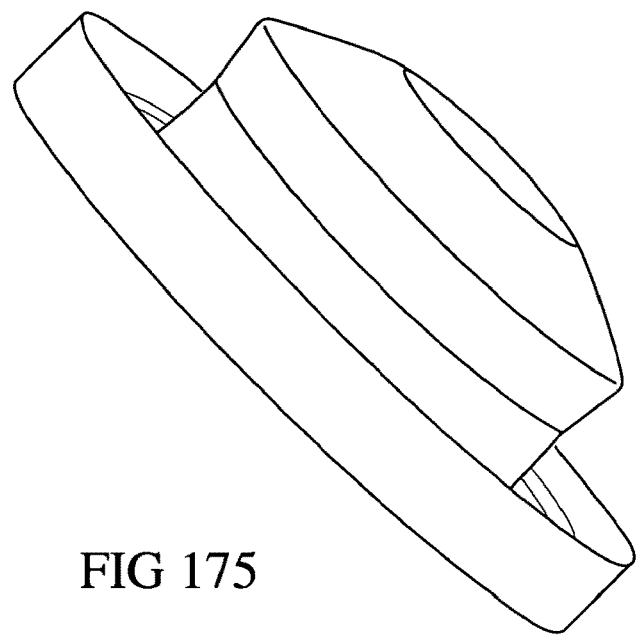
Figure 176:
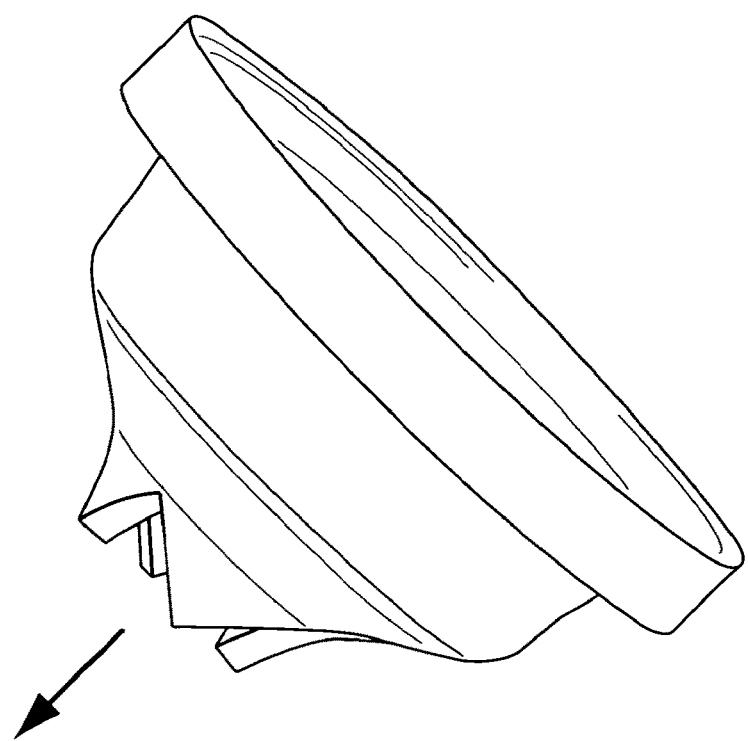

One embodiment of combined PD/TV apparatus is shown as inverting silicone rubber valve in closed position in FIG. 175. FIG. 176 shows said silicone rubber valve in open position, with arrow indicating the direction of the flow of air through the orifice acting as Powder Deagglomeration (PD) apparatus. Recovery of PD/TV apparatus as silicone rubber valve to the shape shown in FIG. 175 when delivery of powder medicament is completed will tend to keep PD/TV apparatus clean.

Figure 177:
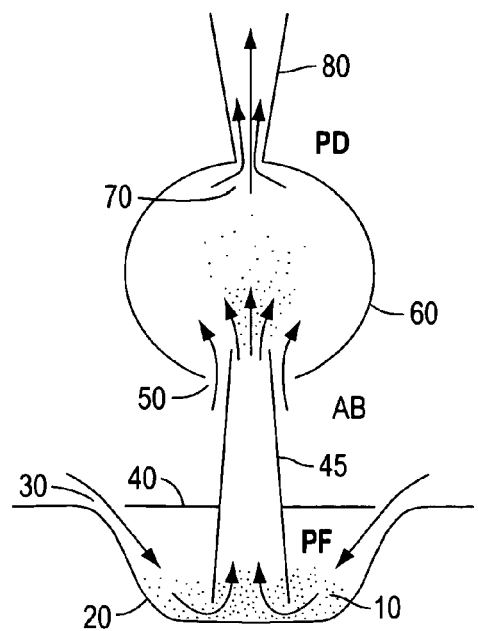

The flow of air through Airflow Bypass (AB) may be used to provide a sheath of clean air around the aerosol flow approaching the PD or FR/PD apparatus, whether simple orifice or variable area orifice, to further help keep the orifice clean and free of powder otherwise subject to sticking to the orifice because of possible impaction with the orifice. One embodiment utilizing clean air from Air Bypass (AB) is shown in FIG. 177, showing one possible arrangement of PF, AB and PD sections of the embodiments shown in FIGS. 165 and 166. FIG. 177 shows PF apparatus consisting of blister pack well 20 containing powder 10 with blister pack lid 40 having cut inlet hole 30 and uptake tube 45, AB apparatus consisting of inlet hole 50 into chamber 60, and PD apparatus consisting of orifice 70 and diffuser 80.

Figure 165:
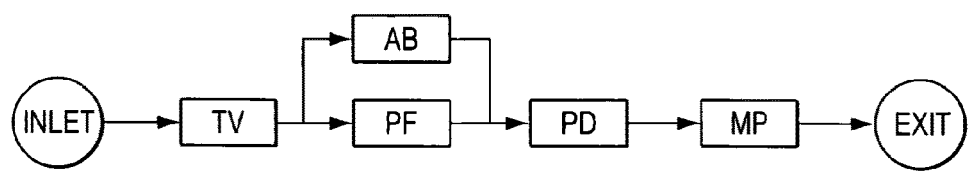
Figure 166:
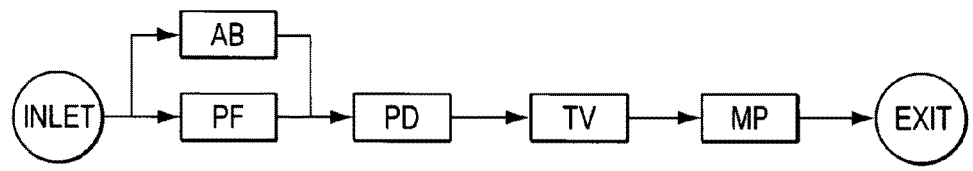
Figure 167:
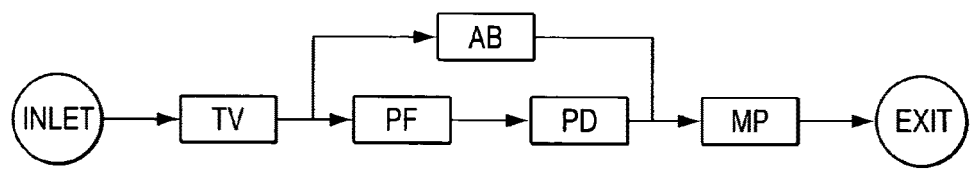
Figure 168:
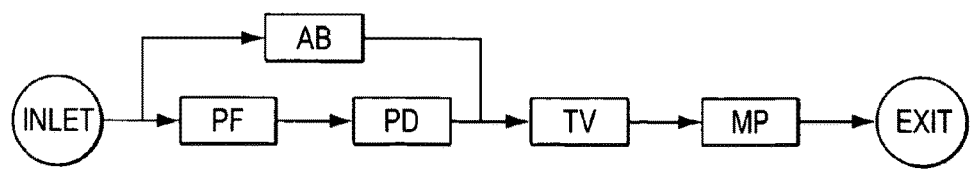
Figure 178:
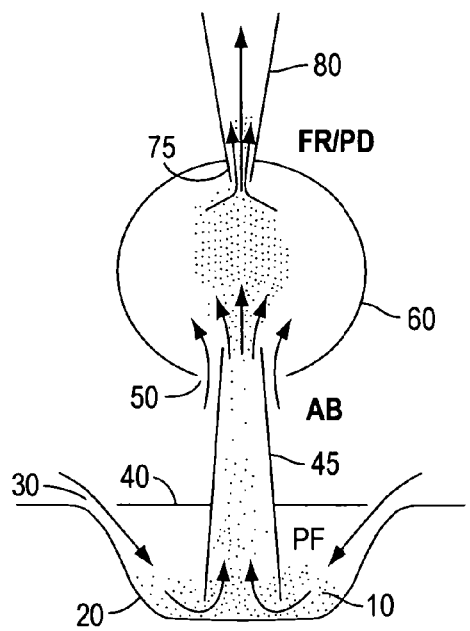

Another embodiment utilizing clean air from Air Bypass (AB) is shown in FIG. 178, showing one possible arrangement of PF, AB and PD sections of the embodiments shown in FIGS. 165 and 166. FIG. 178 shows PF apparatus consisting of blister pack well 20 containing powder 10 with blister pack lid 40 having cut inlet hole 30 and uptake tube 45, AB apparatus consisting of inlet hole 50 into chamber 60, and FR/PD apparatus consisting of Flow Regulator with deagglomerating orifice 75 and diffuser 80. One could see that FR/PD apparatus could be replaced with PD/TV apparatus as shown in flow architecture in FIG. 171.

The invention also provides for any apparatus, such as an inhaler, which includes at least one of the following features: a mechanism configured to create at least one air inlet opening in a wall of a receptacle by puncturing and tearing, whereby the tearing bends torn edges of the at least one air inlet opening inwardly as described herein; a deoccluding device arranged within a feed tube as described herein; a receptacle impacting device as described herein; and a receptacle lock system as described herein.

In some embodiments, the present invention is able to passively administer low doses of powder, such as less than 3 mg, less than 2 mg, or less than 1 mg.

Unless otherwise indicated, illustrated features in the drawings are to relative scale.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

The invention claimed is:

1. A powder dispensing apparatus, comprising:
   a support for supporting a powder-containing blister, the blister having at least one wall;
   an outlet for communicating a flow of powder to a user of the apparatus;
   a feed tube communicating with the outlet, the feed tube structured and arranged to deliver powder from the blister to the outlet;
   a deoccluding device arranged within the feed tube, the deoccluding device comprising a bent wire for puncturing the wall of the blister so as to allow an air flow from the blister and into the feed tube, and for deoccluding;
   a blister impacting device comprising at least one arm that impacts the blister; and a cutting mechanism configured to create at least one air inlet opening in the wall of the blister, whereby air may be drawn into the blister to aerosolize the powder therein.

2. The apparatus of claim 1, wherein the bent wire is a generally V-shaped wire, configured to puncture the wall of the blister so as to allow an air flow from the blister and into the feed tube.

* * * * *